(12) United States Patent
Hannah et al.

(10) Patent No.: US 8,362,321 B2
(45) Date of Patent: Jan. 29, 2013

(54) METHODS AND MATERIALS FOR INCREASING STARCH BIOSYNTHESIS IN PLANTS

(75) Inventors: L. Curtis Hannah, Gainesville, FL (US); Nikolaos Georgelis, Lesvos (GR)

(73) Assignee: University of Florida Research Foundation, Inc., Gainesville, FL (US)

( * ) Notice: Subject to any disclaimer, the term of this patent is extended or adjusted under 35 U.S.C. 154(b) by 693 days.

(21) Appl. No.: 12/322,467

(22) Filed: Feb. 2, 2009

(65) Prior Publication Data
US 2010/0199385 A1 Aug. 5, 2010

(51) Int. Cl.
*A01H 5/00* (2006.01)
*A01H 5/10* (2006.01)
*C12N 15/11* (2006.01)
*C12N 15/82* (2006.01)

(52) U.S. Cl. ....... 800/284; 800/298; 536/23.2; 435/468; 435/91.1

(58) Field of Classification Search ........... 800/205, 800/208; 435/172.1, 172.3
See application file for complete search history.

(56) References Cited

U.S. PATENT DOCUMENTS

| | | | |
|---|---|---|---|
| 5,034,322 A | 7/1991 | Rogers et al. | |
| 5,106,739 A | 4/1992 | Comai et al. | |
| 5,589,610 A | 12/1996 | DeBeuckeleer et al. | |
| 5,589,618 A | 12/1996 | Hannah et al. | |
| 5,625,136 A | 4/1997 | Koziel et al. | |
| 5,639,948 A | 6/1997 | Michiels et al. | |
| 5,650,557 A | 7/1997 | Hannah et al. | |
| 5,661,017 A | 8/1997 | Dunahay et al. | |
| 5,872,216 A | 2/1999 | Hannah et al. | |
| 6,069,300 A | 5/2000 | Hannah et al. | |
| 6,184,438 B1 | 2/2001 | Hannah | |
| 6,403,863 B1 | 6/2002 | Hannah et al. | |
| 6,455,760 B1 | 9/2002 | Zhao et al. | |
| 6,462,185 B1 | 10/2002 | Takakura et al. | |
| 6,696,623 B1 | 2/2004 | Doerner et al. | |
| 6,809,235 B2 * | 10/2004 | Hannah et al. | 800/298 |
| 6,969,783 B2 | 11/2005 | Hannah et al. | |
| 7,173,165 B2 | 2/2007 | Hannah et al. | |
| 7,312,378 B2 * | 12/2007 | Hannah et al. | 800/298 |
| 2003/0084486 A1 | 5/2003 | Bruce et al. | |
| 2003/0177536 A1 | 9/2003 | Grundler et al. | |
| 2004/0019934 A1 | 1/2004 | Ekramoddoullah et al. | |
| 2004/0067506 A1 | 4/2004 | Scheres et al. | |
| 2004/0078841 A1 | 4/2004 | Atkinson et al. | |
| 2004/0123349 A1 | 6/2004 | Xie et al. | |

FOREIGN PATENT DOCUMENTS

| EP | 1528104 | 4/2005 |
|---|---|---|
| WO | WO 2005/019425 | 3/2005 |

OTHER PUBLICATIONS

Chen et al, Heat Shock Proteins of Higher Plants, Jun. 1981, Proc. Natl. Acad. Sci. USA, 78:6, pp. 3526-3530.*
Manicacci et al., Maize Sh2 gene is constrained by natural selection but escaped domestication, 2007, Jour. Evol. Biol. 20:503-516.*
Kavakli et al (JBC 2001 vol. 276, p. 40834-40840).*
Shaw et al Plant Physiol. vol. 98, 1992.*
Akihiro, T et al. "Gene expression of ADP-glucose pyrophosphorylase and starch contents in rice cultured cells are cooperatively regulated by sucrose and ABA" *Plant Cell Physiol*, 2005, pp. 937-946, vol. 46.
Arnold, K. et al. "The Swiss-Model Workspace: a web-based environment for protein structure homology modeling" *Bioinformatics*, 2006, pp. 195-201, vol. 22.
Ballicora, M.A. et al. "Resurrecting the ancestral enzymatic role of a modulatory subunit" *J Biol Chem*, 2005, pp. 10189-10195, vol. 280.
Ballicora, M.A. et al. "Identification of regions critically affecting kinetics and allosteric regulation of the *Escherichia coli* ADP-glucose pyrophosphorylase by modeling and pentapeptide-scanning mutagenesis" *J Bacteriol*, 2007, pp. 5325-5333, vol. 189.
Ballicora, M.A. et al. "ADP-Glc pyrophosphorylase from potato tubers. Site-directed mutagenesis studies of the regulatory sites" *Plant Physiol*, 1998, pp. 265-274, vol. 118.
Bejar, C.M. et al. "Molecular architecture of the glucose 1-phosphate site in ADP-glucose pyrophosphorylases" *J Biol Chem*, 2006, pp. 40473-40484, vol. 281.
Beltz, G. A. et al. "Isolation of multigene families and determination of homologies by filter hybridization methods" *Methods of Enzymology*, R. Wu, L. Grossman and K. Moldave [eds.] Academic Press, New York, 1983, pp. 266-285, vol. 100.
Bishop, J.G. "Directed mutagenesis confirms the functional importance of positively selected sites in polygalacturonase inhibitor protein" *Mol Biol Evol*, 2005, pp. 1531-1534, vol. 22.

(Continued)

*Primary Examiner* — Brent T Page
*Assistant Examiner* — Lee A Visone
(74) *Attorney, Agent, or Firm* — Saliwanchik, Lloyd & Eisenschenk; Doran R. Pace

(57) ABSTRACT

The subject invention concerns materials and methods for providing plants or plant tissue with increased starch biosynthesis. Increased starch biosynthesis provides for increased yield. One aspect of the invention concerns polynucleotides that encode a mutant plant large subunit of AGPase. In one embodiment, a polynucleotide of the invention encodes a plant AGPase large subunit having an amino acid mutation wherein the cysteine amino acid corresponding to amino acid position 424 of wild type maize AGPase large subunit is substituted with an amino acid that results in increased AGPase activity when provided in an AGPase enzyme. In a specific embodiment, the cysteine corresponding to amino acid position 424 of wild type maize AGPase large subunit is substituted with a valine amino acid. The subject invention also comprises a mutant plant large subunit of AGPase encoded by a polynucleotide of the invention. Characterization of kinetic and allosteric properties indicates increased starch yield is provided when the polynucleotides of the invention are expressed in plants such as monocot endosperms.

23 Claims, 6 Drawing Sheets
(4 of 6 Drawing Sheet(s) Filed in Color)

OTHER PUBLICATIONS

Boehlein, S.K. et al. "Purification and characterization of adenosine diphosphate glucose pyrophosphorylase from maize/potato mosaics" *Plant Physiol.*, 2005, pp. 1552-1562, vol. 138.

Boehlein, S.K. et al. "Heat stability and allosteric properties of the maize endosperm ADP-glucose pyrophosphorylase are intimately intertwined" *Plant Physiol*, 2008, pp. 289-299, vol. 146.

Boehlein, S.K. et al. "Characterization of an autonomously activated plant adenosine diphosphate glucose pyrophosphorylase" *Plant Physiol.*, 2009, pp. 318-326, vol. 149.

Burger, B.T. et al. "Relative turnover numbers of maize endosperm and potato tuber ADP-glucose pyrophosphorylases in the absence and presence of 3-PGA" *Planta*, 2003, pp. 449-456, vol. 217.

Cavatorta, J.R. "Positive Darwinian selection at single amino acid sites conferring plant virus resistance" *J Mol Evol*, 2008, pp. 551-557, vol. 67.

Clancy, M. and Hannah, L.C. "Splicing of the maize Sh1 first intron is essential for enhancement of gene expression, and a T-rich motif increases expression without affecting splicing" *Plant Physiol.*, 2002, pp. 918-929, vol. 130, No. 2.

Courville, P. et al. "Solute carrier 11 cation symport requires distinct residues in transmembrane helices 1 and 6" *J Biol Chem*, 2008, pp. 9651-9658, vol. 283.

Crevillen, P. et al. "The different large subunit isoforms of *Arabidopsis thaliana* ADP-glucose pyrophosphorylase confer distinct kinetic and regulatory properties to the heterotetrameric enzyme" *J Biol Chem*, 2003, pp. 28508-28515, vol. 278.

Crevillen, P. et al. "Differential pattern of expression and sugar regulation of *Arabidopsis thaliana* ADP-glucose pyrophosphorylase-encoding genes" *J Biol Chem*, 2005, pp. 8143-8149, vol. 280.

Cross, J.M. et al. "Both subunits of ADP-glucose pyrophosphorylase are regulatory" *Plant Physiol.*, 2004, pp. 137-140, vol. 135.

Cross, J.M. et al. "A polymorphic motif in the small subunit of ADP-glucose pyrophosphorylase modulates interactions between the small and large subunits" *Plant J*, 2005, pp. 501-511, vol. 41.

Frueauf, J.B. et al. "Aspartate residue 142 is important for catalysis by ADP-Glc pyrophosphorylase from *Escherichia coli*" *J Biol Chem*, 2001, pp. 46319-46325, vol. 276.

Frueauf, J.B. et al. "ADP-Glc pyrophosphorylase from potato tuber: site-directed mutagenesis of homologous aspartic acid residues in the small and large subunits" *Plant J*, 2003, pp. 503-511, vol. 33.

Fu, Y. et al. "Mutagenesis of the Glc-1-phosphate-binding site of potato tuber ADP-Glc pyrophosphorylase" *Plant Physiol*, 1998, pp. 989-996, vol. 117.

Furtado, A. et al. "Tools for Use in the Genetic Engineering of Barley" *Proceedings of the 10th Australian Barley technical Symposium*, Canberra, ACT, Australia, 2002.

Georgelis, N. et al. "Duplications and functional divergence of ADP-glucose pyrophosphorylase genes in plants" *BMC Evol Biol*, 2008, pp. 232, vol. 8.

Georgelis, N. et al. "The two AGPase subunits evolve at different rates in angiosperms, yet they are equally sensitive to activity-altering amino acid changes when expressed in bacteria" *Plant Cell*, 2007, pp. 1458-1472, vol. 19.

Georgelis, N. and Hannah L.C. "Isolation of a heat-stable maize endosperm ADP-glucose pyrophosphorylase variant" *Plant Sci*, 2008, pp. 247-254, vol. 175.

Giroux, M.J., et al., "A single mutation that increases maize seed weight" *Proc. Natl. Acad. Sci. USA*, 1996, pp. 5824-5829, vol. 93.

Good, X. et al. "Reduced ethylene synthesis by transgenic tomatoes expressing S-adenosylmethionine hydrolase" *Plant Molec. Biol.*, 1994, pp. 781-790, vol. 26, No. 3.

Greene, T.W., et al., "Enhanced stability of maize endosperm ADP-glucose pyrophosphorylase is gained through mutants that alter subunit interactions" *Proc. Nett Acad. Sci. USA*, 1998, pp. 13342-13347, vol. 95.

Greene, T.W., et al., "Generation of up-regulated allosteric variants of potato ADP-glucose pyrophosphorylase by reversion genetics" *Proc. Natl. Acad. Sci. USA*, 1998, pp. 10322-10327, vol. 95, No. 17.

Greene, T.W. et al. "Mutagenesis of the potato ADPglucose pyrophosphorylase and characterization of an allosteric mutant defective in 3-phosphoglycerate activation" *Proc Natl Acad Sci USA*, 1996, pp. 1509-1513, vol. 93.

Greene, T.W. et al. "Aspartic acid 413 is important for the normal allosteric functioning of ADP-glucose pyrophosphorylase" *Plant Physiol*, 1996, pp. 1315-1320, vol. 112.

Gribaldo, S. et al. "Functional divergence prediction from evolutionary analysis: a case study of vertebrate hemoglobin" *Mol Biol Evol*, 2003, pp. 1754-1759, vol. 20.

Gu, X. "Statistical methods for testing functional divergence after gene duplication" *Mol Biol Evol*, 1999, pp. 1664-1674, vol. 16.

Gu, X. "A simple statistical method for estimating type-II (cluster-specific) functional divergence of protein sequences" *Mol Biol Evol*, 2006, pp. 1937-1945, vol. 23.

Hannah, L.C., et al., "Maize Genes Encoding the Small Subunit of ADP-Glucose Pyrophosphorylase" *Plant Physiol.*, 2001, pp. 173-183, vol. 127.

Hannah, L.C., and Nelson, O.E., Jr. "Characterization of ADP-glucose pyrophosphorylase from shrunken-2 and brittle-2 mutants of maize" *Biochem. Genet.*, 1976, pp. 547-560, vol. 14, abstract only.

Hannah, L.C. "Starch synthesis in the maize endosperm" *Maydica*, 2005, pp. 497-506, vol. 50.

Hwang, Y-S. et al. "Analysis of the Rice Endosperm-Specific Globulin Promoter in Transformed Rice Cells" *Plant Cell Rep.*, 2002, pp. 842-847, vol. 20. No. 9.

Hwang, S.K. et al. "ATP binding site in the plant ADP-glucose pyrophosphorylase large subunit" *FEBS Lett*, 2006, pp. 6741-6748, vol. 580.

Hwang, S.K. et al. "Catalytic implications of the higher plant ADP-glucose pyrophosphorylase large subunit" *Phytochemistry*, 2007, pp. 464-477, vol. 68.

Hwang, S.K. et al. "Direct appraisal of the potato tuber ADP-glucose pyrophosphorylase large subunit in enzyme function by study of a novel mutant form" *J Biol Chem*, 2008, pp. 6640-6647, vol. 283.

Hwang, S.K. et al. "Allosteric regulation of the higher plant ADP-glucose pyrophosphorylase is a product of synergy between the two subunits" *FEBS Lett*, 2005, pp. 983-990, vol. 579.

Iglesias, A. et al. "Expression of the potato tuber ADP-glucose pyrophosphorylase in *Escherichia coli*" *J Biol Chem*, 1993, pp. 1081-1086, vol. 268.

Jin X. et al. "Crystal structure of potato tuber ADP-Glc pyrophosphorylase" *EMBO J*, 2005, pp. 694-704, vol. 24.

Karlin, S. and Altschul, S. F. "Methods for Assessing the Statistical Significance of Molecular Sequence Features by Using General Scoring Schemes" *Proc. Natl. Acad. Sol. USA*, 1990, pp. 2264-2268, vol. 87.

Karlin, S. and Altschul, S. F. "Applications and Statistics for Multiple High-Scoring Segments in Molecular Sequences" *Proc. Natl. Acad. Sci. USA*, 1993, pp. 5873-5877, vol. 90.

Kavakli, I.H. et al. "Investigation of subunit function in ADP-glucose pyrophosphorylase" *Biochem Biophys Res Commun*, 2001, pp. 783-787, vol. 281.

Kavakli, I.H. et al. "Analysis of allosteric effector binding sites of potato ADP-glucose pyrophosphorylase through reverse genetics" *J Biol Chem*, 2001, pp. 40834-40840, vol. 276.

Kim, D. et al. "Subunit interactions specify the allosteric regulatory properties of the potato tuber ADP-glucose pyrophosphorylase" *Biochem Biophys Res Commun*, 2007, pp. 301-306, vol. 362.

Kumar, S. et al. (2004) "MEGA3: Integrated software for Molecular Evolutionary Genetics Analysis and sequence alignment" *Brief Bioinform*, pp. 150-163, vol. 5.

Laughlin, M.J. et al. "Substrate binding mutants of the higher plant ADP-glucose pyrophosphorylase" *Phytochemistry*, 1998, pp. 621-629, vol. 47.

Luthy, R. et al. "Assessment of protein models with 3-dimensional profiles" *Nature*, 1992, pp. 83-85, vol. 356.

Norrgärd, M.A. et al. "Alternative mutations of a positively selected residue elicit gain or loss of functionalities in enzyme evolution" *Proc Natl Acad Sci USA*, 2006, pp. 4876-4881, vol. 103.

Obana, Y. et al. "Enhanced turnover of transitory starch by expression of up-regulated ADP-glucose pyrophosphorylase in *Arabidopsis thaliana*" *Plant Sci.*, 2006, pp. 1-11, vol. 170.

Ohdan, T. et al. "Expression profiling of genes involved in starch synthesis in sink and source organs of rice" *J Exp Bot*, 2005, pp. 3229-3244, vol. 56.

Pettersen, E.F. et al. "UCSF Chimera—A Visualization System for Exploratory Research and Analysis" *J Comput Chem*, 2004, pp. 1605-1612, vol. 25.

Philippe, H. et al. "Heterotachy and functional shift in protein evolution" *IUBMB Life*, 2003, pp. 257-265, vol. 55.

Schwede, T. et al. "Swiss-Model: an automated protein homology-modeling server" *Nucleic Acids Res*, 2003, pp. 3381-3385, vol. 31.

Sakulsingharoja, C., et al., "Engineering starch biosynthesis for increasing rice seed weight: the role of the cytoplasmic ADP-glucose pyrophosphorylase" *Plant Sci.*, 2004, pp. 1323-1333, vol. 167.

Smidansky, E.D., et al., "Enhanced ADP-glucose pyrophosphorylase activity in wheat endosperm increases seed yield" *Proc. Natl. Acad. Sci.*, 2002, pp. 1724-1729, vol. 99, No. 3.

Smidansky, E.D., et al., "Seed yield and plant biomass increases in rice are conferred by deregulation of endosperm ADP-glucose pyrophosphorylase" *Planta*, 2003, pp. 656-664, vol. 216, No. 4.

Stark, D.M., et al., "Regulation of the amount of starch in plant tissues by ADP-glucose pyrophosphorylase" *Science*, 1992, pp. 287-292, vol. 258, No. 5080.

Tsai, C.Y. and Nelson, O.E. "Starch deficient maize mutants lacking adenosine diphosphate glucose pyrophosphorylase activity" *Science*, 1966, pp. 341-343, vol. 151.

Tuncel, A. et al. "Insights into subunit interactions in the heterotetrameric structure of potato ADP-glucose pyrophosphorylase" *Biophys J*, 2008, pp. 3628-3639, vol. 95.

Ventriglia, T. et al. "Two Arabidopsis ADP-Glucose Pyrophosphorylase Large Subunits (APL1 and APL2) Are Catalytic" *Plant Physiol*, 2008, pp. 65-76, vol. 148.

Vriend, G. "What If—a molecular modeling and drug design program" *J Mol Graph*, 1990, pp. 52-56, vol. 8, abstract only.

Wang, Z. et al., "Increasing maize seed weight by enhancing the cytoplasmic ADP-glucose pyrophosphorylase activity in transgenic plants" *Plant Cell Tiss. Organ Cult.*, 2007, pp. 83-92, vol. 88, No. 1.

Wu, C-L. et al. "Promoters of Rice Seed Storage Protein Genes Direct Endosperm-Specific Gene Expression in Transgenic Rice" *Plant and Cell Physiology*, 1998, pp. 885-889, vol. 39, No. 8.

Xu, D. et al., "Systemic induction of a potato pin2 promoter by wounding, methyl jasmonate, and abscisic acid in transgenic rice plants" *Plant Molecular Biology*, 1993, pp. 573-588, vol. 22.

* cited by examiner

FIG. 2

SEQUENCE LISTING

```
<160> NUMBER OF SEQ ID NOS: 50

<210> SEQ ID NO 1
<211> LENGTH: 1551
<212> TYPE: DNA
<213> ORGANISM: Zea mays
<220> FEATURE:
```

```
<221> NAME/KEY: exon
<222> LOCATION: (1)..(1551)
<220> FEATURE:
<221> NAME/KEY: misc_feature
<222> LOCATION: (489)..(489)
<223> OTHER INFORMATION: y = t or c
<220> FEATURE:
<221> NAME/KEY: misc_feature
<222> LOCATION: (1272)..(1272)
<223> OTHER INFORMATION: n is a, c, g, or t
<220> FEATURE:
<221> NAME/KEY: misc_feature
<222> LOCATION: (1308)..(1308)
<223> OTHER INFORMATION: h = a, c, or t
<220> FEATURE:
<221> NAME/KEY: misc_feature
<222> LOCATION: (1362)..(1362)
<223> OTHER INFORMATION: h = a, c, or t

<400> SEQUENCE: 1 atg cag ttt gca ctt gca ttg gac acg aac tca ggt cct cac cag ata      48
Met Gln Phe Ala Leu Ala Leu Asp Thr Asn Ser Gly Pro His Gln Ile
1               5                   10                  15 aga tct tgt gag ggt gat ggg att gac agg ttg gaa aaa tta agt att      96
Arg Ser Cys Glu Gly Asp Gly Ile Asp Arg Leu Glu Lys Leu Ser Ile
            20                  25                  30 ggg ggc aga aag cag gag aaa gct ttg aga aat agg tgc ttt ggt ggt     144
Gly Gly Arg Lys Gln Glu Lys Ala Leu Arg Asn Arg Cys Phe Gly Gly
        35                  40                  45 aga gtt gct gca act aca caa tgt att ctt acc tca gat gct tgt cct     192
Arg Val Ala Ala Thr Thr Gln Cys Ile Leu Thr Ser Asp Ala Cys Pro
    50                  55                  60 gaa act ctt cat tct caa aca cag tcc tct agg aaa aat tat gct gat     240
Glu Thr Leu His Ser Gln Thr Gln Ser Ser Arg Lys Asn Tyr Ala Asp
65                  70                  75                  80 gca aac cgt gta tct gct atc att ttg ggc gga ggc act gga tct cag     288
Ala Asn Arg Val Ser Ala Ile Ile Leu Gly Gly Gly Thr Gly Ser Gln
                85                  90                  95 ctc ttt cct ctg aca agc aca aga gct acg cct gct gta cct gtt gga     336
Leu Phe Pro Leu Thr Ser Thr Arg Ala Thr Pro Ala Val Pro Val Gly
            100                 105                 110 gga tgt tac agg ctt att gat atc cct atg agt aac tgc ttc aac agt     384
Gly Cys Tyr Arg Leu Ile Asp Ile Pro Met Ser Asn Cys Phe Asn Ser
        115                 120                 125 ggt ata aat aag ata ttt gtg atg agt cag ttc aat tct act tcg ctt     432
Gly Ile Asn Lys Ile Phe Val Met Ser Gln Phe Asn Ser Thr Ser Leu
    130                 135                 140 aac cgc cat att cat cgt aca tac ctt gaa ggc ggg atc aac ttt gct     480
Asn Arg His Ile His Arg Thr Tyr Leu Glu Gly Gly Ile Asn Phe Ala
145                 150                 155                 160 gat gga tct gta cag gta tta gcg gct aca caa atg cct gaa gag cca     528
Asp Gly Ser Val Gln Val Leu Ala Ala Thr Gln Met Pro Glu Glu Pro
                165                 170                 175 gct gga tgg ttc cag ggt aca gca gac tct atc aga aaa ttt atc tgg     576
Ala Gly Trp Phe Gln Gly Thr Ala Asp Ser Ile Arg Lys Phe Ile Trp
            180                 185                 190 gta ctc gag gat tat tac agt cac aaa tcc att gac aac att gta atc     624
Val Leu Glu Asp Tyr Tyr Ser His Lys Ser Ile Asp Asn Ile Val Ile
        195                 200                 205 ttg agt ggc gat cag ctt tat cgg atg aat tac atg gaa ctt gtg cag     672
Leu Ser Gly Asp Gln Leu Tyr Arg Met Asn Tyr Met Glu Leu Val Gln
    210                 215                 220 aaa cat gtc gag gac gat gct gat atc act ata tca tgt gct cct gtt     720
Lys His Val Glu Asp Asp Ala Asp Ile Thr Ile Ser Cys Ala Pro Val
225                 230                 235                 240
```

| | | | | | | | | | | | | | | | | |
|---|---|---|---|---|---|---|---|---|---|---|---|---|---|---|---|---|
| gat | gag | agc | cga | gct | tct | aaa | aat | ggg | cta | gtg | aag | att | gat | cat | act | 768 |
| Asp | Glu | Ser | Arg | Ala | Ser | Lys | Asn | Gly | Leu | Val | Lys | Ile | Asp | His | Thr | |
| | | | 245 | | | | | 250 | | | | | 255 | | | |
| gga | cgt | gta | ctt | caa | ttc | ttt | gaa | aaa | cca | aag | ggt | gct | gat | ttg | aat | 816 |
| Gly | Arg | Val | Leu | Gln | Phe | Phe | Glu | Lys | Pro | Lys | Gly | Ala | Asp | Leu | Asn | |
| | | 260 | | | | | 265 | | | | | 270 | | | | |
| tct | atg | aga | gtt | gag | acc | aac | ttc | ctg | agc | tat | gct | ata | gat | gat | gca | 864 |
| Ser | Met | Arg | Val | Glu | Thr | Asn | Phe | Leu | Ser | Tyr | Ala | Ile | Asp | Asp | Ala | |
| | 275 | | | | | 280 | | | | | 285 | | | | | |
| cag | aaa | tat | cca | tac | ctt | gca | tca | atg | ggc | att | tat | gtc | ttc | aag | aaa | 912 |
| Gln | Lys | Tyr | Pro | Tyr | Leu | Ala | Ser | Met | Gly | Ile | Tyr | Val | Phe | Lys | Lys | |
| 290 | | | | | 295 | | | | | 300 | | | | | | |
| gat | gca | ctt | tta | gac | ctt | ctc | aag | tca | aaa | tat | act | caa | tta | cat | gac | 960 |
| Asp | Ala | Leu | Leu | Asp | Leu | Leu | Lys | Ser | Lys | Tyr | Thr | Gln | Leu | His | Asp | |
| 305 | | | | | 310 | | | | | 315 | | | | | 320 | |
| ttt | gga | tct | gaa | atc | ctc | cca | aga | gct | gta | cta | gat | cat | agt | gtg | cag | 1008 |
| Phe | Gly | Ser | Glu | Ile | Leu | Pro | Arg | Ala | Val | Leu | Asp | His | Ser | Val | Gln | |
| | | | 325 | | | | | 330 | | | | | 335 | | | |
| gca | tgc | att | ttt | acg | ggc | tat | tgg | gag | gat | gtt | gga | aca | atc | aaa | tca | 1056 |
| Ala | Cys | Ile | Phe | Thr | Gly | Tyr | Trp | Glu | Asp | Val | Gly | Thr | Ile | Lys | Ser | |
| | | 340 | | | | | 345 | | | | | 350 | | | | |
| ttc | ttt | gat | gca | aac | ttg | gcc | ctc | act | gag | cag | cct | tcc | aag | ttt | gat | 1104 |
| Phe | Phe | Asp | Ala | Asn | Leu | Ala | Leu | Thr | Glu | Gln | Pro | Ser | Lys | Phe | Asp | |
| | 355 | | | | | 360 | | | | | 365 | | | | | |
| ttt | tac | gat | cca | aaa | aca | cct | ttc | ttc | act | gca | ccc | cga | tgc | ttg | cct | 1152 |
| Phe | Tyr | Asp | Pro | Lys | Thr | Pro | Phe | Phe | Thr | Ala | Pro | Arg | Cys | Leu | Pro | |
| 370 | | | | | 375 | | | | | 380 | | | | | | |
| ccg | acg | caa | ttg | gac | aag | tgc | aag | atg | aaa | tat | gca | ttt | atc | tca | gat | 1200 |
| Pro | Thr | Gln | Leu | Asp | Lys | Cys | Lys | Met | Lys | Tyr | Ala | Phe | Ile | Ser | Asp | |
| 385 | | | | | 390 | | | | | 395 | | | | | 400 | |
| ggt | tgc | tta | ctg | aga | gaa | tgc | aac | atc | gag | cat | tct | gtg | att | gga | gtc | 1248 |
| Gly | Cys | Leu | Leu | Arg | Glu | Cys | Asn | Ile | Glu | His | Ser | Val | Ile | Gly | Val | |
| | | | 405 | | | | | 410 | | | | | 415 | | | |
| tgc | tca | cgt | gtc | agc | tct | gga | gtn | gaa | ctc | aag | gac | tcc | gtg | atg | atg | 1296 |
| Cys | Ser | Arg | Val | Ser | Ser | Gly | Val | Glu | Leu | Lys | Asp | Ser | Val | Met | Met | |
| | | | 420 | | | | | 425 | | | | | 430 | | | |
| gga | gcg | gac | ath | tat | gaa | act | gaa | gaa | gaa | gct | tca | aag | cta | ctg | tta | 1344 |
| Gly | Ala | Asp | Ile | Tyr | Glu | Thr | Glu | Glu | Glu | Ala | Ser | Lys | Leu | Leu | Leu | |
| | | 435 | | | | | 440 | | | | | 445 | | | | |
| gct | ggg | aag | gtc | cca | ath | gga | ata | gga | agg | aac | aca | aag | ata | agg | aac | 1392 |
| Ala | Gly | Lys | Val | Pro | Ile | Gly | Ile | Gly | Arg | Asn | Thr | Lys | Ile | Arg | Asn | |
| | 450 | | | | | 455 | | | | | 460 | | | | | |
| tgt | atc | att | gac | atg | aat | gct | agg | att | ggg | aag | aac | gtg | gtg | atc | aca | 1440 |
| Cys | Ile | Ile | Asp | Met | Asn | Ala | Arg | Ile | Gly | Lys | Asn | Val | Val | Ile | Thr | |
| 465 | | | | | 470 | | | | | 475 | | | | | 480 | |
| aac | agt | aag | ggc | atc | caa | gag | gct | gat | cac | ccg | gaa | gaa | ggg | tac | tac | 1488 |
| Asn | Ser | Lys | Gly | Ile | Gln | Glu | Ala | Asp | His | Pro | Glu | Glu | Gly | Tyr | Tyr | |
| | | | 485 | | | | | 490 | | | | | 495 | | | |
| ata | agg | tct | gga | atc | gtg | gtg | atc | ttg | aag | aat | gca | acc | atc | aac | gat | 1536 |
| Ile | Arg | Ser | Gly | Ile | Val | Val | Ile | Leu | Lys | Asn | Ala | Thr | Ile | Asn | Asp | |
| | | | 500 | | | | | 505 | | | | | 510 | | | |
| ggg | tct | gtc | ata | tag | | | | | | | | | | | | 1551 |
| Gly | Ser | Val | Ile | | | | | | | | | | | | | |
| | | | 515 | | | | | | | | | | | | | |

<210> SEQ ID NO 2
<211> LENGTH: 516
<212> TYPE: PRT
<213> ORGANISM: Zea mays

<400> SEQUENCE: 2

-continued

```
Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
                85                  90                  95

Leu Phe Pro Leu Thr Ser Thr Arg Ala Thr Pro Ala Val Pro Val Gly
                100                 105                 110

Gly Cys Tyr Arg Leu Ile Asp Ile Pro Met Ser Asn Cys Phe Asn Ser
            115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Ile Asn Phe Ala
145                 150                 155                 160

Asp Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
        195                 200                 205

Leu Ser Gly Asp Gln Leu Tyr Arg Met Asn Tyr Met Glu Leu Val Gln
    210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270

Ser Met Arg Val Glu Thr Asn Phe Leu Ser Tyr Ala Ile Asp Asp Ala
        275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp His Ser Val Gln
                325                 330                 335

Ala Cys Ile Phe Thr Gly Tyr Trp Glu Asp Val Gly Thr Ile Lys Ser
            340                 345                 350

Phe Phe Asp Ala Asn Leu Ala Leu Thr Glu Gln Pro Ser Lys Phe Asp
        355                 360                 365

Phe Tyr Asp Pro Lys Thr Pro Phe Phe Thr Ala Pro Arg Cys Leu Pro
    370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Val Glu Leu Lys Asp Ser Val Met Met
```

```
                      420               425               430
Gly Ala Asp Ile Tyr Glu Thr Glu Glu Ala Ser Lys Leu Leu Leu
        435                 440                 445

Ala Gly Lys Val Pro Ile Gly Ile Gly Arg Asn Thr Lys Ile Arg Asn
        450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
                500                 505                 510

Gly Ser Val Ile
        515

<210> SEQ ID NO 3
<211> LENGTH: 1425
<212> TYPE: DNA
<213> ORGANISM: Zea mays

<400> SEQUENCE: 3
atggacatgg ctttggcgtc taaagcctcc cctccgccat ggaatgccac cgccgccgag      60
cagccaattc caaagcgtga caaagccgct gcaaatgatt caacatgyct caatcctcaa     120
gctcatgata gtgttcttgg aatcattctg ggaggtggtg ctgggactag attgtacccc     180
ttgacaaaga agcgtgccaa gcctgcagtg ccattgggtg ccaactatag actgattgat     240
attcctgtca gcaattgtct caacagcaac atatccaaga tctatgtgct aacgcaattt     300
aactctgctt ccctcaaccg tcacctctca agagcctacg ggagcaacat tggagggtac     360
aagaatgaag ggtttgttga agtcttagct gcacagcaga gcccagataa tccaaactgg     420
tttcagggta ctgcagatgc tgtaaggcag tacttgtggt tgtttgagga gcataatgtg     480
atggaatttc taattcttgc tggcgatcac ctgtaccgga tggactatga aaagttcatt     540
caggcacaca gagaaacaaa tgctgatatt accgttgctg ccctaccgat ggatgagaaa     600
cgtgcaactg catttggcct catgaaaatt gatgaagaag gaggatcat tgagtttgct      660 gagaaaccga aggagagca gttgaaagca atgatggttg acaccaccat acttggcctt     720
gatgacgtga gggcaaagga aatgccttat attgctagca tgggtatcta tgttttcagc     780
aaagatgtaa tgcttcagct cctccgtgaa caatttcctg aagccaatga ctttggaagt     840
gaggttattc aggtgcaac cagcattgga aagagggttc aggcttatct gtatgatggt      900
tactgggaag atatcggtac cattgcggca tttatataatg caaacttggg aataaccaag     960
aagccaatac cagatttcag cttctatgac cgttttgctc aatttatac acaacctcga    1020 cacctgccac cttcaaaggt tcttgatgct gatgtgacag acagtgttat tggtgaagga    1080
tgtgttatta aaactgcaa gataaaccat tctgtagttg gactccgatc ttgcatatct    1140
gaaggtgcta tcatagagga cagtttacta atgggtgcgg actactatga cacagaagct    1200
gataaaaaac tccttgccga aaaggtggc attcctattg gtattgggaa aaattcatgc    1260
atcaggagag caatcattga caagaatgct cgaattggag acaatgttaa gatactcaat    1320
gctgacaatg ttcaagaagc tgcaatggag acagacgggt acttcatcaa aggtggaatt    1380
gtcacagtga tcaaggatgc tttactccct agtggaacag ttata             1425

<210> SEQ ID NO 4
<211> LENGTH: 1428
<212> TYPE: DNA
```

<213> ORGANISM: Zea mays

<400> SEQUENCE: 4

```
atggacatgg ctttggcgtc taaagcctcc cctccgccat ggaatgccac cgccgccgag      60
cagccaattc caaagcgtga caaagccgct gcaaatgatt caacarcatg yctcaatcct     120
caagctcatg atagtgttct tggaatcatt ctgggaggtg gtgctgggac tagattgtac     180
cccttgacaa agaagcgtgc caagcctgca gtgccattgg gtgccaacta tagactgatt     240
gatattcctg tcagcaattg tctcaacagc aacatatcca agatctatgt gctaacgcaa     300
tttaactctg cttccctcaa ccgtcacctc tcaagagcct acgggagcaa cattggaggg     360
tacaagaatg aagggtttgt tgaagtctta gctgcacagc agagcccaga taatccaaac     420
tggtttcagg gtactgcaga tgctgtaagg cagtacttgt ggttgtttga ggagcataat     480
gtgatggaat ttctaattct tgctggcgat cacctgtacc ggatggacta tgaaaagttc     540
attcaggcac acagagaaac aaatgctgat attaccgttg ctgccctacc gatggatgag     600
aaacgtgcaa ctgcatttgg cctcatgaaa attgatgaag aagggaggat cattgagttt     660
gctgagaaac cgaaggaga gcagttgaaa gcaatgatgg ttgacaccac catacttggc     720
cttgatgacg tgagggcaaa ggaaatgcct tatattgcta gcatgggtat ctatgttttc     780
agcaaagatg taatgcttca gctcctccgt gaacaatttc ctgaagccaa tgactttgga     840
agtgaggtta ttccaggtgc aaccagcatt ggaaagaggg ttcaggctta tctgtatgat     900
ggttactggg aagatatcgg taccattgcg gcatttttata atgcaaactt gggaataacc     960
aagaagccaa taccagattt cagcttctat gaccgttttg ctccaattta tacacaacct    1020
cgacacctgc caccttcaaa ggttcttgat gctgatgtga cagacagtgt tattggtgaa    1080
ggatgtgtta ttaaaaactg caagataaac cattctgtag ttggactccg atcttgcata    1140
tctgaaggtg ctatcataga ggacagttta ctaatgggtg cggactacta tgagacagaa    1200
gctgataaaa aactccttgc cgaaaaaggt ggcattccta ttggtattgg gaaaaattca    1260
tgcatcagga gagcaatcat tgacaagaat gctcgaattg gagacaatgt taagatactc    1320
aatgctgaca atgttcaaga agctgcaatg gagacagacg ggtacttcat caaaggtgga    1380
attgtcacag tgatcaagga tgctttactc cctagtggaa cagttata                 1428
```

<210> SEQ ID NO 5  
<211> LENGTH: 1428  
<212> TYPE: DNA  
<213> ORGANISM: Zea mays

<400> SEQUENCE: 5

```
atggacatgg ctttggcgtc taaagcctcc cctccgccat ggaatgccac cgccgccgag      60
cagccaattc caaagcgtga caaagccgct gcaaatgatt caagarcatg yctcaatcct     120
caagctcatg atagtgttct tggaatcatt ctgggaggtg gtgctgggac tagattgtac     180
cccttgacaa agaagcgtgc caagcctgca gtgccattgg gtgccaacta tagactgatt     240
gatattcctg tcagcaattg tctcaacagc aacatatcca agatctatgt gctaacgcaa     300
tttaactctg cttccctcaa ccgtcacctc tcaagagcct acgggagcaa cattggaggg     360
tacaagaatg aagggtttgt tgaagtctta gctgcacagc agagcccaga taatccaaac     420
tggtttcagg gtactgcaga tgctgtaagg cagtacttgt ggttgtttga ggagcataat     480
gtgatggaat ttctaattct tgctggcgat cacctgtacc ggatggacta tgaaaagttc     540
attcaggcac acagagaaac aaatgctgat attaccgttg ctgccctacc gatggatgag     600
```

```
aaacgtgcaa ctgcatttgg cctcatgaaa attgatgaag aagggaggat cattgagttt      660
gctgagaaac cgaaaggaga gcagttgaaa gcaatgatgg ttgacaccac catacttggc      720
cttgatgacg tgagggcaaa ggaaatgcct tatattgcta gcatgggtat ctatgttttc      780
agcaaagatg taatgcttca gctcctccgt gaacaatttc ctgaagccaa tgactttgga      840
agtgaggtta ttccaggtgc aaccagcatt ggaaagaggg ttcaggctta tctgtatgat      900
ggttactggg aagatatcgg taccattgcg gcatttttata atgcaaactt gggaataacc      960
aagaagccaa taccagattt cagcttctat gaccgttttg ctccaattta tacacaacct     1020
cgacacctgc caccttcaaa ggttcttgat gctgatgtga cagacagtgt tattggtgaa     1080
ggatgtgtta ttaaaaactg caagataaac cattctgtag ttggactccg atcttgcata     1140
tctgaaggtg ctatcataga ggacagttta ctaatgggtg cggactacta tgagacagaa     1200
gctgataaaa aactccttgc cgaaaaaggt ggcattccta ttggtattgg gaaaaattca     1260
tgcatcagga gagcaatcat tgacaagaat gctcgaattg gagacaatgt taagatactc     1320
aatgctgaca atgttcaaga agctgcaatg gagacagacg ggtacttcat caaaggtgga     1380
attgtcacag tgatcaagga tgctttactc cctagtggaa cagttata                  1428
```

<210> SEQ ID NO 6
<211> LENGTH: 475
<212> TYPE: PRT
<213> ORGANISM: Zea mays

<400> SEQUENCE: 6

```
Met Asp Met Ala Leu Ala Ser Lys Ala Ser Pro Pro Trp Asn Ala
1               5                   10                  15

Thr Ala Glu Gln Pro Ile Pro Lys Arg Asp Lys Ala Ala Asn
            20                  25                  30

Asp Ser Thr Cys Leu Asn Pro Gln Ala His Asp Ser Val Leu Gly Ile
            35                  40                  45

Ile Leu Gly Gly Gly Ala Gly Thr Arg Leu Tyr Pro Leu Thr Lys Lys
    50                  55                  60

Arg Ala Lys Pro Ala Val Pro Leu Gly Ala Asn Tyr Arg Leu Ile Asp
65                  70                  75                  80

Ile Pro Val Ser Asn Cys Leu Asn Ser Asn Ile Ser Lys Ile Tyr Val
                85                  90                  95

Leu Thr Gln Phe Asn Ser Ala Ser Leu Asn Arg His Leu Ser Arg Ala
            100                 105                 110

Tyr Gly Ser Asn Ile Gly Gly Tyr Lys Asn Glu Gly Phe Val Glu Val
            115                 120                 125

Leu Ala Ala Gln Gln Ser Pro Asp Asn Pro Asn Trp Phe Gln Gly Thr
    130                 135                 140

Ala Asp Ala Val Arg Gln Tyr Leu Trp Leu Phe Glu Glu His Asn Val
145                 150                 155                 160

Met Glu Phe Leu Ile Leu Ala Gly Asp His Leu Tyr Arg Met Asp Tyr
                165                 170                 175

Glu Lys Phe Ile Gln Ala His Arg Glu Thr Asn Ala Asp Ile Thr Val
            180                 185                 190

Ala Ala Leu Pro Met Asp Glu Lys Arg Ala Thr Ala Phe Gly Leu Met
            195                 200                 205

Lys Ile Asp Glu Glu Gly Arg Ile Ile Glu Phe Ala Glu Lys Pro Lys
    210                 215                 220

Gly Glu Gln Leu Lys Ala Met Met Val Asp Thr Thr Ile Leu Gly Leu
225                 230                 235                 240
```

```
Asp Asp Val Arg Ala Lys Glu Met Pro Tyr Ile Ala Ser Met Gly Ile
                245                 250                 255

Tyr Val Phe Ser Lys Asp Val Met Leu Gln Leu Leu Arg Glu Gln Phe
            260                 265                 270

Pro Glu Ala Asn Asp Phe Gly Ser Glu Val Ile Pro Gly Ala Thr Ser
        275                 280                 285

Ile Gly Lys Arg Val Gln Ala Tyr Leu Tyr Asp Gly Tyr Trp Glu Asp
    290                 295                 300

Ile Gly Thr Ile Ala Ala Phe Tyr Asn Ala Asn Leu Gly Ile Thr Lys
305                 310                 315                 320

Lys Pro Ile Pro Asp Phe Ser Phe Tyr Asp Arg Phe Ala Pro Ile Tyr
                325                 330                 335

Thr Gln Pro Arg His Leu Pro Pro Ser Lys Val Leu Asp Ala Asp Val
            340                 345                 350

Thr Asp Ser Val Ile Gly Glu Gly Cys Val Ile Lys Asn Cys Lys Ile
        355                 360                 365

Asn His Ser Val Val Gly Leu Arg Ser Cys Ile Ser Glu Gly Ala Ile
    370                 375                 380

Ile Glu Asp Ser Leu Leu Met Gly Ala Asp Tyr Tyr Glu Thr Glu Ala
385                 390                 395                 400

Asp Lys Lys Leu Leu Ala Glu Lys Gly Gly Ile Pro Ile Gly Ile Gly
                405                 410                 415

Lys Asn Ser Cys Ile Arg Arg Ala Ile Ile Asp Lys Asn Ala Arg Ile
            420                 425                 430

Gly Asp Asn Val Lys Ile Leu Asn Ala Asp Asn Val Gln Glu Ala Ala
        435                 440                 445

Met Glu Thr Asp Gly Tyr Phe Ile Lys Gly Gly Ile Val Thr Val Ile
    450                 455                 460

Lys Asp Ala Leu Leu Pro Ser Gly Thr Val Ile
465                 470                 475

<210> SEQ ID NO 7
<211> LENGTH: 476
<212> TYPE: PRT
<213> ORGANISM: Zea mays

<400> SEQUENCE: 7

Met Asp Met Ala Leu Ala Ser Lys Ala Ser Pro Pro Trp Asn Ala
1               5                   10                  15

Thr Ala Ala Glu Gln Pro Ile Pro Lys Arg Asp Lys Ala Ala Asn
                20                  25                  30

Asp Ser Gln Thr Cys Leu Asn Pro Gln Ala His Asp Ser Val Leu Gly
            35                  40                  45

Ile Ile Leu Gly Gly Gly Ala Gly Thr Arg Leu Tyr Pro Leu Thr Lys
50                  55                  60

Lys Arg Ala Lys Pro Ala Val Pro Leu Gly Ala Asn Tyr Arg Leu Ile
65                  70                  75                  80

Asp Ile Pro Val Ser Asn Cys Leu Asn Ser Asn Ile Ser Lys Ile Tyr
                85                  90                  95

Val Leu Thr Gln Phe Asn Ser Ala Ser Leu Asn Arg His Leu Ser Arg
            100                 105                 110

Ala Tyr Gly Ser Asn Ile Gly Gly Tyr Lys Asn Glu Gly Phe Val Glu
        115                 120                 125

Val Leu Ala Ala Gln Gln Ser Pro Asp Asn Pro Asn Trp Phe Gln Gly
    130                 135                 140
```

Thr Ala Asp Ala Val Arg Gln Tyr Leu Trp Leu Phe Glu Glu His Asn
145                 150                 155                 160

Val Met Glu Phe Leu Ile Leu Ala Gly Asp His Leu Tyr Arg Met Asp
            165                 170                 175

Tyr Glu Lys Phe Ile Gln Ala His Arg Glu Thr Asn Ala Asp Ile Thr
        180                 185                 190

Val Ala Ala Leu Pro Met Asp Glu Lys Arg Ala Thr Ala Phe Gly Leu
    195                 200                 205

Met Lys Ile Asp Glu Glu Gly Arg Ile Ile Glu Phe Ala Glu Lys Pro
210                 215                 220

Lys Gly Glu Gln Leu Lys Ala Met Met Val Asp Thr Thr Ile Leu Gly
225                 230                 235                 240

Leu Asp Asp Val Arg Ala Lys Glu Met Pro Tyr Ile Ala Ser Met Gly
                245                 250                 255

Ile Tyr Val Phe Ser Lys Asp Val Met Leu Gln Leu Leu Arg Glu Gln
            260                 265                 270

Phe Pro Glu Ala Asn Asp Phe Gly Ser Glu Val Ile Pro Gly Ala Thr
        275                 280                 285

Ser Ile Gly Lys Arg Val Gln Ala Tyr Leu Tyr Asp Gly Tyr Trp Glu
290                 295                 300

Asp Ile Gly Thr Ile Ala Ala Phe Tyr Asn Ala Asn Leu Gly Ile Thr
305                 310                 315                 320

Lys Lys Pro Ile Pro Asp Phe Ser Phe Tyr Asp Arg Phe Ala Pro Ile
                325                 330                 335

Tyr Thr Gln Pro Arg His Leu Pro Pro Ser Lys Val Leu Asp Ala Asp
            340                 345                 350

Val Thr Asp Ser Val Ile Gly Glu Gly Cys Val Ile Lys Asn Cys Lys
        355                 360                 365

Ile Asn His Ser Val Val Gly Leu Arg Ser Cys Ile Ser Glu Gly Ala
370                 375                 380

Ile Ile Glu Asp Ser Leu Leu Met Gly Ala Asp Tyr Tyr Glu Thr Glu
385                 390                 395                 400

Ala Asp Lys Lys Leu Leu Ala Glu Lys Gly Gly Ile Pro Ile Gly Ile
                405                 410                 415

Gly Lys Asn Ser Cys Ile Arg Arg Ala Ile Ile Asp Lys Asn Ala Arg
            420                 425                 430

Ile Gly Asp Asn Val Lys Ile Leu Asn Ala Asp Asn Val Gln Glu Ala
        435                 440                 445

Ala Met Glu Thr Asp Gly Tyr Phe Ile Lys Gly Ile Val Thr Val
    450                 455                 460

Ile Lys Asp Ala Leu Leu Pro Ser Gly Thr Val Ile
465                 470                 475

<210> SEQ ID NO 8
<211> LENGTH: 476
<212> TYPE: PRT
<213> ORGANISM: Zea mays

<400> SEQUENCE: 8

Met Asp Met Ala Leu Ala Ser Lys Ala Ser Pro Pro Trp Asn Ala
1               5                   10                  15

Thr Ala Ala Glu Gln Pro Ile Pro Lys Arg Asp Lys Ala Ala Ala Asn
            20                  25                  30

Asp Ser Glu Thr Cys Leu Asn Pro Gln Ala His Asp Ser Val Leu Gly
        35                  40                  45

```
Ile Ile Leu Gly Gly Gly Ala Gly Thr Arg Leu Tyr Pro Leu Thr Lys
         50                  55                  60

Lys Arg Ala Lys Pro Ala Val Pro Leu Gly Ala Asn Tyr Arg Leu Ile
 65              70                  75                  80

Asp Ile Pro Val Ser Asn Cys Leu Asn Ser Asn Ile Ser Lys Ile Tyr
                 85                  90                  95

Val Leu Thr Gln Phe Asn Ser Ala Ser Leu Asn Arg His Leu Ser Arg
            100                 105                 110

Ala Tyr Gly Ser Asn Ile Gly Gly Tyr Lys Asn Glu Gly Phe Val Glu
            115                 120                 125

Val Leu Ala Ala Gln Gln Ser Pro Asp Asn Pro Asn Trp Phe Gln Gly
            130                 135                 140

Thr Ala Asp Ala Val Arg Gln Tyr Leu Trp Leu Phe Glu Glu His Asn
145                 150                 155                 160

Val Met Glu Phe Leu Ile Leu Ala Gly Asp His Leu Tyr Arg Met Asp
                165                 170                 175

Tyr Glu Lys Phe Ile Gln Ala His Arg Glu Thr Asn Ala Asp Ile Thr
            180                 185                 190

Val Ala Ala Leu Pro Met Asp Glu Lys Arg Ala Thr Ala Phe Gly Leu
            195                 200                 205

Met Lys Ile Asp Glu Glu Gly Arg Ile Ile Glu Phe Ala Glu Lys Pro
210                 215                 220

Lys Gly Glu Gln Leu Lys Ala Met Met Val Asp Thr Thr Ile Leu Gly
225                 230                 235                 240

Leu Asp Asp Val Arg Ala Lys Glu Met Pro Tyr Ile Ala Ser Met Gly
                245                 250                 255

Ile Tyr Val Phe Ser Lys Asp Val Met Leu Gln Leu Leu Arg Glu Gln
            260                 265                 270

Phe Pro Glu Ala Asn Asp Phe Gly Ser Glu Val Ile Pro Gly Ala Thr
            275                 280                 285

Ser Ile Gly Lys Arg Val Gln Ala Tyr Leu Tyr Asp Gly Tyr Trp Glu
            290                 295                 300

Asp Ile Gly Thr Ile Ala Ala Phe Tyr Asn Ala Asn Leu Gly Ile Thr
305                 310                 315                 320

Lys Lys Pro Ile Pro Asp Phe Ser Phe Tyr Asp Arg Phe Ala Pro Ile
                325                 330                 335

Tyr Thr Gln Pro Arg His Leu Pro Pro Ser Lys Val Leu Asp Ala Asp
            340                 345                 350

Val Thr Asp Ser Val Ile Gly Glu Gly Cys Val Ile Lys Asn Cys Lys
            355                 360                 365

Ile Asn His Ser Val Val Gly Leu Arg Ser Cys Ile Ser Glu Gly Ala
            370                 375                 380

Ile Ile Glu Asp Ser Leu Leu Met Gly Ala Asp Tyr Tyr Glu Thr Glu
385                 390                 395                 400

Ala Asp Lys Lys Leu Leu Ala Glu Lys Gly Gly Ile Pro Ile Gly Ile
                405                 410                 415

Gly Lys Asn Ser Cys Ile Arg Arg Ala Ile Ile Asp Lys Asn Ala Arg
            420                 425                 430

Ile Gly Asp Asn Val Lys Ile Leu Asn Ala Asp Asn Val Gln Glu Ala
            435                 440                 445

Ala Met Glu Thr Asp Gly Tyr Phe Ile Lys Gly Gly Ile Val Thr Val
450                 455                 460

Ile Lys Asp Ala Leu Leu Pro Ser Gly Thr Val Ile
```

465          470          475

<210> SEQ ID NO 9
<211> LENGTH: 1428
<212> TYPE: DNA
<213> ORGANISM: Artificial Sequence
<220> FEATURE:
<223> OTHER INFORMATION: Nucleotide sequence encoding a chimeric AGP
      small subunit protein having the amino acid sequence shown in SEQ
      ID NO. 10

<400> SEQUENCE: 9

| | | | | | |
|---|---|---|---|---|---|
| atggacatgg | ctttggcgtc | taaagcctcc | cctccgccat | ggaatgccac | cgccgccgag | 60 |
| cagccaattc | caaagcgtga | caaagccgct | gcaaatgatt | caacatacct | caatcctcaa | 120 |
| gctcatgata | gtgttcttgg | aatcattctg | ggaggtggtg | ctgggactag | attgtacccc | 180 |
| ttgacaaaga | agcgtgccaa | gcctgcagtg | ccattgggtg | ccaactatag | actgattgat | 240 |
| attcctgtca | gcaattgtct | caacagcaac | atatccaaga | tctatgtgct | aacgcaattt | 300 |
| aactctcctt | ccctcaaccg | tcacctctca | agagcctacg | ggagcaacat | tggagggtac | 360 |
| aagaatgaag | ggtttgttga | agtcttagct | gcacagcaga | gcccagataa | tccaaactgg | 420 |
| tttcagggta | ctgcagatgc | tgtaaggcag | tacttgtggt | tgtttgagga | gcataatgtg | 480 |
| atggaatttc | taattcttgc | tggcgatcac | ctgtaccgga | tggactatga | aaagttcatt | 540 |
| caggcacaca | gagaaacaaa | tgctgatatt | accgttgctg | ccctaccgat | ggatgagaag | 600 |
| cgtgccactg | catttggtct | catgaagatt | gacgaagaag | gacgcattat | tgaatttgca | 660 |
| gagaaaccgc | aaggagagca | attgcaagca | atgaaagtgg | atactaccat | tttaggtctt | 720 |
| gatgacaaga | gagctaaaga | aatgccttc | attgccagta | tgggtatata | tgtcattagc | 780 |
| aaagacgtga | tgttaaacct | acttcgtgac | aagttccctg | gggccaatga | ttttggtagt | 840 |
| gaagttattc | ctggtgcaac | ttcacttggg | atgagagtgc | aagcttattt | atatgatggg | 900 |
| tactgggaag | atattggtac | cattgaagct | ttctacaatg | ccaatttggg | cattacaaaa | 960 |
| aagccggtgc | agattttag | cttttacgac | cgatcagccc | caatctacac | ccaacctcga | 1020 |
| tatctaccac | catcaaaaat | gcttgatgct | gatgtcacag | tagtgtcat | ggtgaaggt | 1080 |
| tgtgtgatca | gaactgtaa | gattcatcat | ccgtggttg | gactcagatc | atgcatatca | 1140 |
| gagggagcaa | ttatagaaga | ctcacttttg | atggggcag | attactatga | gactgatgct | 1200 |
| gacaggaagt | tgctggctgc | aaagggcagt | gtcccaattg | gcatcggcaa | gaattgtcac | 1260 |
| attaaaagag | ccattatcga | caagaatgcc | cgtatagggg | acaatgtgaa | gatcattaac | 1320 |
| aaagacaacg | ttcaagaagc | ggctagggaa | acagatggat | acttcatcaa | gagtgggatt | 1380 |
| gtcaccgtca | tcaaggatgc | tttgattcca | agtggaatca | tcatctga | | 1428 |

<210> SEQ ID NO 10
<211> LENGTH: 475
<212> TYPE: PRT
<213> ORGANISM: Artificial Sequence
<220> FEATURE:
<223> OTHER INFORMATION: Amino acid sequence of a chimeric AGP small
      subunit protein

<400> SEQUENCE: 10

Met Asp Met Ala Leu Ala Ser Lys Ala Ser Pro Pro Pro Trp Asn Ala
1               5                   10                  15

Thr Ala Ala Glu Gln Pro Ile Pro Lys Arg Asp Lys Ala Ala Ala Asn
            20                  25                  30

Asp Ser Thr Tyr Leu Asn Pro Gln Ala His Asp Ser Val Leu Gly Ile

-continued

```
                    35                  40                  45
Ile Leu Gly Gly Gly Ala Gly Thr Arg Leu Tyr Pro Leu Thr Lys Lys
 50                  55                  60

Arg Ala Lys Pro Ala Val Pro Leu Gly Ala Asn Tyr Arg Leu Ile Asp
 65                  70                  75                  80

Ile Pro Val Ser Asn Cys Leu Asn Ser Asn Ile Ser Lys Ile Tyr Val
                 85                  90                  95

Leu Thr Gln Phe Asn Ser Pro Ser Leu Asn Arg His Leu Ser Arg Ala
            100                 105                 110

Tyr Gly Ser Asn Ile Gly Gly Tyr Lys Asn Glu Gly Phe Val Glu Val
        115                 120                 125

Leu Ala Ala Gln Gln Ser Pro Asp Asn Pro Asn Trp Phe Gln Gly Thr
130                 135                 140

Ala Asp Ala Val Arg Gln Tyr Leu Trp Leu Phe Glu Glu His Asn Val
145                 150                 155                 160

Met Glu Phe Leu Ile Leu Ala Gly Asp His Leu Tyr Arg Met Asp Tyr
                165                 170                 175

Glu Lys Phe Ile Gln Ala His Arg Glu Thr Asn Ala Asp Ile Thr Val
            180                 185                 190

Ala Ala Leu Pro Met Asp Glu Lys Arg Ala Thr Ala Phe Gly Leu Met
        195                 200                 205

Lys Ile Asp Glu Glu Gly Arg Ile Ile Glu Phe Ala Glu Lys Pro Gln
210                 215                 220

Gly Glu Gln Leu Gln Ala Met Lys Val Asp Thr Thr Ile Leu Gly Leu
225                 230                 235                 240

Asp Asp Lys Arg Ala Lys Glu Met Pro Phe Ile Ala Ser Met Gly Ile
                245                 250                 255

Tyr Val Ile Ser Lys Asp Val Met Leu Asn Leu Leu Arg Asp Lys Phe
            260                 265                 270

Pro Gly Ala Asn Asp Phe Gly Ser Glu Val Ile Pro Gly Ala Thr Ser
        275                 280                 285

Leu Gly Met Arg Val Gln Ala Tyr Leu Tyr Asp Gly Tyr Trp Glu Asp
290                 295                 300

Ile Gly Thr Ile Glu Ala Phe Tyr Asn Ala Asn Leu Gly Ile Thr Lys
305                 310                 315                 320

Lys Pro Val Pro Asp Phe Ser Phe Tyr Asp Arg Ser Ala Pro Ile Tyr
                325                 330                 335

Thr Gln Pro Arg Tyr Leu Pro Pro Ser Lys Met Leu Asp Ala Asp Val
            340                 345                 350

Thr Asp Ser Val Ile Gly Glu Gly Cys Val Ile Lys Asn Cys Lys Ile
        355                 360                 365

His His Ser Val Val Gly Leu Arg Ser Cys Ile Ser Glu Gly Ala Ile
370                 375                 380

Ile Glu Asp Ser Leu Leu Met Gly Ala Asp Tyr Tyr Glu Thr Asp Ala
385                 390                 395                 400

Asp Arg Lys Leu Leu Ala Ala Lys Gly Ser Val Pro Ile Gly Ile Gly
                405                 410                 415

Lys Asn Cys His Ile Lys Arg Ala Ile Ile Asp Lys Asn Ala Arg Ile
            420                 425                 430

Gly Asp Asn Val Lys Ile Ile Asn Lys Asp Asn Val Gln Glu Ala Ala
        435                 440                 445

Arg Glu Thr Asp Gly Tyr Phe Ile Lys Ser Gly Ile Val Thr Val Ile
450                 455                 460
```

Lys Asp Ala Leu Ile Pro Ser Gly Ile Ile Ile
465                 470                 475

<210> SEQ ID NO 11
<211> LENGTH: 475
<212> TYPE: PRT
<213> ORGANISM: Artificial Sequence
<220> FEATURE:
<223> OTHER INFORMATION: Amino acid sequence of a chimeric AGP small
      subunit protein

<400> SEQUENCE: 11

Met Asp Met Ala Leu Ala Ser Lys Ala Ser Pro Pro Trp Asn Ala
1               5                   10                  15

Thr Ala Ala Glu Gln Pro Ile Pro Lys Arg Asp Lys Ala Ala Asn
                20                  25                  30

Asp Ser Thr Tyr Leu Asn Pro Gln Ala His Asp Ser Val Leu Gly Ile
                35                  40                  45

Ile Leu Gly Gly Gly Ala Gly Thr Arg Leu Tyr Pro Leu Thr Lys Lys
50                  55                  60

Arg Ala Lys Pro Ala Val Pro Leu Gly Ala Asn Tyr Arg Leu Ile Asp
65                  70                  75                  80

Ile Pro Val Ser Asn Cys Leu Asn Ser Asn Ile Ser Lys Ile Tyr Val
                85                  90                  95

Leu Thr Gln Phe Asn Ser Ala Ser Leu Asn Arg His Leu Ser Arg Ala
                100                 105                 110

Tyr Gly Ser Asn Ile Gly Gly Tyr Lys Asn Glu Gly Phe Val Glu Val
                115                 120                 125

Leu Ala Ala Gln Gln Ser Pro Asp Asn Pro Asn Trp Phe Gln Gly Thr
130                 135                 140

Ala Asp Ala Val Arg Gln Tyr Leu Trp Leu Phe Glu Glu His Asn Val
145                 150                 155                 160

Met Glu Phe Leu Ile Leu Ala Gly Asp His Leu Tyr Arg Met Asp Tyr
                165                 170                 175

Glu Lys Phe Ile Gln Ala His Arg Glu Thr Asn Ala Asp Ile Thr Val
                180                 185                 190

Ala Ala Leu Pro Met Asp Glu Lys Arg Ala Thr Ala Phe Gly Leu Met
                195                 200                 205

Lys Ile Asp Glu Glu Gly Arg Ile Ile Glu Phe Ala Glu Lys Pro Gln
210                 215                 220

Gly Glu Gln Leu Gln Ala Met Lys Val Asp Thr Thr Ile Leu Gly Leu
225                 230                 235                 240

Asp Asp Lys Arg Ala Lys Glu Met Pro Phe Ile Ala Ser Met Gly Ile
                245                 250                 255

Tyr Val Ile Ser Lys Asp Val Met Leu Asn Leu Leu Arg Asp Lys Phe
                260                 265                 270

Pro Gly Ala Asn Asp Phe Gly Ser Glu Val Ile Pro Gly Ala Thr Ser
                275                 280                 285

Leu Gly Met Arg Val Gln Ala Tyr Leu Tyr Asp Gly Tyr Trp Glu Asp
                290                 295                 300

Ile Gly Thr Ile Glu Ala Phe Tyr Asn Ala Asn Leu Gly Ile Thr Lys
305                 310                 315                 320

Lys Pro Val Pro Asp Phe Ser Phe Tyr Asp Arg Ser Ala Pro Ile Tyr
                325                 330                 335

Thr Gln Pro Arg Tyr Leu Pro Pro Ser Lys Met Leu Asp Ala Asp Val
                340                 345                 350

```
Thr Asp Ser Val Ile Gly Glu Gly Cys Val Ile Lys Asn Cys Lys Ile
        355                 360                 365

His His Ser Val Val Gly Leu Arg Ser Cys Ile Ser Glu Gly Ala Ile
        370                 375                 380

Ile Glu Asp Ser Leu Leu Met Gly Ala Asp Tyr Tyr Glu Thr Asp Ala
385                 390                 395                 400

Asp Arg Lys Leu Leu Ala Ala Lys Gly Ser Val Pro Ile Gly Ile Gly
                405                 410                 415

Lys Asn Cys His Ile Lys Arg Ala Ile Ile Asp Lys Asn Ala Arg Ile
                420                 425                 430

Gly Asp Asn Val Lys Ile Ile Asn Lys Asp Asn Val Gln Glu Ala Ala
                435                 440                 445

Arg Glu Thr Asp Gly Tyr Phe Ile Lys Ser Gly Ile Val Thr Val Ile
        450                 455                 460

Lys Asp Ala Leu Ile Pro Ser Gly Ile Ile Ile
465                 470                 475

<210> SEQ ID NO 12
<211> LENGTH: 1425
<212> TYPE: DNA
<213> ORGANISM: Artificial Sequence
<220> FEATURE:
<223> OTHER INFORMATION: zea mays Bt2 gene
<220> FEATURE:
<221> NAME/KEY: misc_feature
<222> LOCATION: (1386)..(1386)
<223> OTHER INFORMATION: h = a or c or t

<400> SEQUENCE: 12
atggacatgg ctttggcgtc taaagcctcc cctccgccat ggaatgccac cgccgccgag      60
cagccaattc caaagcgtga caaagccgct gcaaatgatt caacatacct caatcctcaa     120
gctcatgata gtgttcttgg aatcattctg ggaggtggtg ctgggactag attgtacccc     180
ttgacaaaga agcgtgccaa gcctgcagtg ccattgggtg ccaactatag actgattgat     240
attcctgtca gcaattgtct caacagcaac atatccaaga tctatgtgct aacgcaattt     300
aactctgctt ccctcaaccg tcacctctca agagcctacg ggagcaacat ggagggtac      360 aagaatgaag ggtttgttga agtcttagct gcacagcaga gcccagataa tccaaactgg     420 tttcaggta ctgcagatgc tgtaaggcag tacttgtggt tgtttgagga gcataatgtg      480
atggaatttc taattcttgc tggcgatcac ctgtaccgga tggactatga aaagttcatt     540
caggcacaca gagaaacaaa tgctgatatt accgttgctg ccctaccgat ggatgagaaa     600
cgtgcaactg catttggcct catgaaaatt gatgaagaag ggaggatcat tgagtttgct     660
gagaaaccga aggagagca gttgaaagca atgatggttg acaccaccat acttggcctt     720
gatgacgtga gggcaaagga atgccttat attgctagca tgggtatcta tgttttcagc     780
aaagatgtaa tgcttcagct cctccgtgaa caatttcctg aagccaatga ctttggaagt     840
gaggttattc aggtgcaac cagcattgga aagagggttc aggcttatct gtatgatggt     900
tactgggaag atatcggtac cattgcggca ttttataatg caaacttggg aataaccaag     960
aagccaatac cagatttcag cttctatgac cgttttgctc caatttatac acaacctcga    1020
cacctgccac cttcaaaggt tcttgatgct gatgtgacag acagtgttat tggtgaagga    1080
tgtgttatta aaactgcaa gataaaccat tctgtagttg gactccgatc ttgcatatct    1140
gaaggtgcta tcatagagga cagtttacta atgggtgcgg actactatga gacagaagct    1200
gataaaaaac tccttgccga aaaggtggc attcctattg gtattgggaa aaattcatgc    1260
```

```
atcaggagag caatcattga caagaatgct cgaattggag acaatgttaa gatactcaat    1320
gctgacaatg ttcaagaagc tgcaatggag acagacgggt acttcatcaa aggtggaatt    1380
gtcathgtga tcaaggatgc tttactccct agtggaacag ttata                     1425
```

<210> SEQ ID NO 13
<211> LENGTH: 475
<212> TYPE: PRT
<213> ORGANISM: Artificial Sequence
<220> FEATURE:
<223> OTHER INFORMATION: zea mays BT2 protein

<400> SEQUENCE: 13

```
Met Asp Met Ala Leu Ala Ser Lys Ala Ser Pro Pro Trp Asn Ala
1               5                   10                  15

Thr Ala Glu Gln Pro Ile Pro Lys Arg Asp Lys Ala Ala Asn
            20                  25                  30

Asp Ser Thr Tyr Leu Asn Pro Gln Ala His Asp Ser Val Leu Gly Ile
        35                  40                  45

Ile Leu Gly Gly Gly Ala Gly Thr Arg Leu Tyr Pro Leu Thr Lys Lys
    50                  55                  60

Arg Ala Lys Pro Ala Val Pro Leu Gly Ala Asn Tyr Arg Leu Ile Asp
65                  70                  75                  80

Ile Pro Val Ser Asn Cys Leu Asn Ser Asn Ile Ser Lys Ile Tyr Val
                85                  90                  95

Leu Thr Gln Phe Asn Ser Ala Ser Leu Asn Arg His Leu Ser Arg Ala
            100                 105                 110

Tyr Gly Ser Asn Ile Gly Gly Tyr Lys Asn Glu Gly Phe Val Glu Val
        115                 120                 125

Leu Ala Ala Gln Gln Ser Pro Asp Asn Pro Asn Trp Phe Gln Gly Thr
    130                 135                 140

Ala Asp Ala Val Arg Gln Tyr Leu Trp Leu Phe Glu Glu His Asn Val
145                 150                 155                 160

Met Glu Phe Leu Ile Leu Ala Gly Asp His Leu Tyr Arg Met Asp Tyr
                165                 170                 175

Glu Lys Phe Ile Gln Ala His Arg Glu Thr Asn Ala Asp Ile Thr Val
            180                 185                 190

Ala Ala Leu Pro Met Asp Glu Lys Arg Ala Thr Ala Phe Gly Leu Met
        195                 200                 205

Lys Ile Asp Glu Glu Gly Arg Ile Ile Glu Phe Ala Glu Lys Pro Lys
    210                 215                 220

Gly Glu Gln Leu Lys Ala Met Met Val Asp Thr Thr Ile Leu Gly Leu
225                 230                 235                 240

Asp Asp Val Arg Ala Lys Glu Met Pro Tyr Ile Ala Ser Met Gly Ile
                245                 250                 255

Tyr Val Phe Ser Lys Asp Val Met Leu Gln Leu Leu Arg Glu Gln Phe
            260                 265                 270

Pro Glu Ala Asn Asp Phe Gly Ser Glu Val Ile Pro Gly Ala Thr Ser
        275                 280                 285

Ile Gly Lys Arg Val Gln Ala Tyr Leu Tyr Asp Gly Tyr Trp Glu Asp
    290                 295                 300

Ile Gly Thr Ile Ala Ala Phe Tyr Asn Ala Asn Leu Gly Ile Thr Lys
305                 310                 315                 320

Lys Pro Ile Pro Asp Phe Ser Phe Tyr Asp Arg Phe Ala Pro Ile Tyr
                325                 330                 335

Thr Gln Pro Arg His Leu Pro Pro Ser Lys Val Leu Asp Ala Asp Val
```

```
                340                 345                 350
Thr Asp Ser Val Ile Gly Glu Gly Cys Val Ile Lys Asn Cys Lys Ile
            355                 360                 365

Asn His Ser Val Val Gly Leu Arg Ser Cys Ile Ser Glu Gly Ala Ile
            370                 375                 380

Ile Glu Asp Ser Leu Leu Met Gly Ala Asp Tyr Tyr Glu Thr Glu Ala
385                 390                 395                 400

Asp Lys Lys Leu Leu Ala Glu Lys Gly Ile Pro Ile Gly Ile Gly
                405                 410                 415

Lys Asn Ser Cys Ile Arg Arg Ala Ile Ile Asp Lys Asn Ala Arg Ile
                420                 425                 430

Gly Asp Asn Val Lys Ile Leu Asn Ala Asp Asn Val Gln Glu Ala Ala
                435                 440                 445

Met Glu Thr Asp Gly Tyr Phe Ile Lys Gly Gly Ile Val Ile Val Ile
                450                 455                 460

Lys Asp Ala Leu Leu Pro Ser Gly Thr Val Ile
465                 470                 475

<210> SEQ ID NO 14
<211> LENGTH: 518
<212> TYPE: PRT
<213> ORGANISM: Zea mays

<400> SEQUENCE: 14

Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
                20                  25                  30

Gly Gly Arg Lys Gln Glu Lys Ala Leu Arg Asn Arg Cys Phe Gly Gly
            35                  40                  45

Arg Val Ala Ala Thr Thr Gln Cys Ile Leu Thr Ser Asp Ala Cys Pro
        50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
                85                  90                  95

Leu Phe Pro Leu Thr Ser Thr Arg Ala Thr Pro Ala Val Pro Val Gly
                100                 105                 110

Gly Cys Tyr Arg Leu Ile Asp Ile Pro Met Ser Asn Cys Phe Asn Ser
            115                 120                 125

Gly Ile Asn Lys Ile Phe Val Met Ser Gln Phe Asn Ser Thr Ser Leu
        130                 135                 140

Asn Arg His Ile His Arg Thr Tyr Leu Glu Gly Gly Ile Asn Phe Ala
145                 150                 155                 160

Asp Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
                180                 185                 190

Val Leu Glu Asp Tyr Tyr Ser His Lys Ser Ile Asp Asn Ile Val Ile
            195                 200                 205

Leu Ser Gly Asp Gln Leu Tyr Arg Met Asn Tyr Met Glu Leu Val Gln
        210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
```

```
                        245                 250                 255
Gly Arg Val Leu Gln Phe Phe Glu Lys Pro Lys Gly Ala Asp Leu Asn
                260                 265                 270

Ser Met Arg Val Glu Thr Asn Phe Leu Ser Tyr Ala Ile Asp Asp Ala
            275                 280                 285

Gln Lys Tyr Pro Tyr Leu Ala Ser Met Gly Ile Tyr Val Phe Lys Lys
        290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp His Ser Val Gln
                325                 330                 335

Ala Cys Ile Phe Thr Gly Tyr Trp Glu Asp Val Gly Thr Ile Lys Ser
            340                 345                 350

Phe Phe Asp Ala Asn Leu Ala Leu Thr Glu Gln Pro Ser Lys Phe Asp
        355                 360                 365

Phe Tyr Asp Pro Lys Thr Pro Phe Phe Thr Ala Pro Arg Cys Leu Pro
    370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Val Glu Leu Lys Asp Ser Val Met Met
            420                 425                 430

Gly Ala Asp Ile Tyr Glu Thr Glu Glu Ala Ser Lys Leu Leu Leu
        435                 440                 445

Ala Gly Lys Val Pro Ile Gly Ile Gly Arg Asn Thr Lys Ile Arg Asn
    450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Ser
                485                 490                 495

Tyr Tyr Ile Arg Ser Gly Ile Val Val Ile Leu Lys Asn Ala Thr Ile
            500                 505                 510

Asn Asp Gly Ser Val Ile
        515

<210> SEQ ID NO 15
<211> LENGTH: 516
<212> TYPE: PRT
<213> ORGANISM: Zea mays

<400> SEQUENCE: 15

Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Gly Thr Gly Ser Gln
                85                  90                  95

Leu Phe Pro Leu Thr Ser Thr Arg Ala Thr Pro Ala Val Pro Val Gly
```

```
                100             105             110
Gly Cys Tyr Arg Leu Ile Asp Ile Pro Met Ser Asn Cys Phe Asn Ser
        115                 120                 125
Gly Ile Asn Lys Ile Phe Val Met Ser Gln Phe Asn Ser Thr Ser Leu
        130                 135                 140
Asn Arg His Ile His Arg Thr Tyr Leu Glu Gly Ile Asn Phe Ala
145                 150                 155                 160
Asp Gly Ser Val Gln Val Leu Ala Ala Thr Gln Met Pro Glu Glu Pro
                165                 170                 175
Ala Gly Trp Phe Gln Gly Thr Ala Asp Ser Ile Arg Lys Phe Ile Trp
        180                 185                 190
Val Leu Glu Asp Tyr Tyr Ser His Lys Ser Ile Asp Asn Ile Val Ile
        195                 200                 205
Leu Ser Gly Asp Gln Leu Tyr Arg Met Asn Tyr Met Glu Leu Val Gln
        210                 215                 220
Lys His Val Glu Asp Ala Asp Ile Thr Ile Ser Cys Ala Pro Val
225                 230                 235                 240
Asp Glu Ser Arg Ala Ser Lys Asn Gly Leu Val Lys Ile Asp His Thr
                245                 250                 255
Gly Arg Val Leu Gln Phe Phe Glu Lys Pro Lys Gly Ala Asp Leu Asn
            260                 265                 270
Ser Met Arg Val Glu Thr Asn Phe Leu Ser Tyr Ala Ile Asp Ala
                275                 280                 285
Gln Lys Tyr Pro Tyr Leu Ala Ser Met Gly Ile Tyr Val Phe Lys Lys
        290                 295                 300
Asp Ala Leu Leu Asp Leu Leu Lys Ser Lys Tyr Thr Gln Leu His Asp
305                 310                 315                 320
Phe Gly Ser Glu Ile Leu Pro Arg Ala Val Leu Asp Tyr Ser Val Gln
                325                 330                 335
Ala Cys Ile Phe Thr Gly Tyr Trp Glu Asp Val Gly Thr Ile Lys Ser
                340                 345                 350
Phe Phe Asp Ala Asn Leu Ala Leu Thr Glu Gln Pro Ser Lys Phe Asp
        355                 360                 365
Phe Tyr Asp Pro Lys Thr Pro Phe Phe Thr Ala Pro Arg Cys Leu Pro
370                 375                 380
Pro Thr Gln Leu Asp Lys Cys Lys Met Lys Tyr Ala Phe Ile Ser Asp
385                 390                 395                 400
Gly Cys Leu Leu Arg Glu Cys Asn Ile Glu His Ser Val Ile Gly Val
                405                 410                 415
Cys Ser Arg Val Ser Ser Gly Val Glu Leu Lys Asp Ser Val Met Met
                420                 425                 430
Gly Ala Asp Ile Tyr Glu Thr Glu Glu Ala Ser Lys Leu Leu Leu
        435                 440                 445
Ala Gly Lys Val Pro Ile Gly Ile Gly Arg Asn Thr Lys Ile Arg Asn
        450                 455                 460
Cys Ile Ile Asp Met Asn Ala Arg Ile Gly Lys Asn Val Val Ile Thr
465                 470                 475                 480
Asn Ser Lys Gly Ile Gln Glu Ala Asp His Pro Glu Glu Gly Tyr Tyr
                485                 490                 495
Ile Arg Ser Gly Ile Val Val Ile Leu Lys Asn Ala Thr Ile Asn Asp
                500                 505                 510
Gly Ser Val Ile
        515
```

<210> SEQ ID NO 16
<211> LENGTH: 518
<212> TYPE: PRT
<213> ORGANISM: Zea mays

<400> SEQUENCE: 16

```
Met Gln Phe Ala Leu Ala Leu Asp Thr Asn Ser Gly Pro His Gln Ile
 1               5                  10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
                85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Gly Ile Asn Phe Ala
145                 150                 155                 160

Asp Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
        195                 200                 205

Leu Ser Gly Asp Gln Leu Tyr Arg Met Asn Tyr Met Glu Leu Val Gln
    210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270

Ser Met Arg Val Glu Thr Asn Phe Leu Ser Tyr Ala Ile Asp Asp Ala
        275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp Tyr Ser Val Gln
                325                 330                 335

Ala Cys Ile Phe Thr Gly Tyr Trp Glu Asp Val Gly Thr Ile Lys Ser
            340                 345                 350

Phe Phe Asp Ala Asn Leu Ala Leu Thr Glu Gln Pro Ser Lys Phe Asp
        355                 360                 365

Phe Tyr Asp Pro Lys Thr Pro Phe Phe Thr Ala Pro Arg Cys Leu Pro
    370                 375                 380
```

```
Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Val Glu Leu Lys Asp Ser Val Met Met
            420                 425                 430

Gly Ala Asp Ile Tyr Glu Thr Glu Glu Ala Ser Lys Leu Leu Leu
        435                 440                 445

Ala Gly Lys Val Pro Ile Gly Ile Gly Arg Asn Thr Lys Ile Arg Asn
450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Ser
                485                 490                 495

Tyr Tyr Ile Arg Ser Gly Ile Val Val Ile Leu Lys Asn Ala Thr Ile
            500                 505                 510

Asn Asp Gly Ser Val Ile
            515

<210> SEQ ID NO 17
<211> LENGTH: 1551
<212> TYPE: DNA
<213> ORGANISM: Zea mays
<220> FEATURE:
<221> NAME/KEY: exon
<222> LOCATION: (1)..(1551)
<220> FEATURE:
<221> NAME/KEY: misc_feature
<222> LOCATION: (489)..(489)
<223> OTHER INFORMATION: y = t or c
<220> FEATURE:
<221> NAME/KEY: misc_feature
<222> LOCATION: (1308)..(1308)
<223> OTHER INFORMATION: h = a, c, or t
<220> FEATURE:
<221> NAME/KEY: misc_feature
<222> LOCATION: (1362)..(1362)
<223> OTHER INFORMATION: h = a, c, or t

<400> SEQUENCE: 17 atg cag ttt gca ctt gca ttg gac acg aac tca ggt cct cac cag ata      48
Met Gln Phe Ala Leu Ala Leu Asp Thr Asn Ser Gly Pro His Gln Ile
1               5                   10                  15 aga tct tgt gag ggt gat ggg att gac agg ttg gaa aaa tta agt att      96
Arg Ser Cys Glu Gly Asp Gly Ile Asp Arg Leu Glu Lys Leu Ser Ile
            20                  25                  30 ggg ggc aga aag cag gag aaa gct ttg aga aat agg tgc ttt ggt ggt     144
Gly Gly Arg Lys Gln Glu Lys Ala Leu Arg Asn Arg Cys Phe Gly Gly
        35                  40                  45 aga gtt gct gca act aca caa tgt att ctt acc tca gat gct tgt cct     192
Arg Val Ala Ala Thr Thr Gln Cys Ile Leu Thr Ser Asp Ala Cys Pro
    50                  55                  60 gaa act ctt cat tct caa aca cag tcc tct agg aaa aat tat gct gat     240
Glu Thr Leu His Ser Gln Thr Gln Ser Ser Arg Lys Asn Tyr Ala Asp
65                  70                  75                  80 gca aac cgt gta tct gct atc att ttg ggc gga ggc act gga tct cag     288
Ala Asn Arg Val Ser Ala Ile Ile Leu Gly Gly Gly Thr Gly Ser Gln
                85                  90                  95 ctc ttt cct ctg aca agc aca aga gct acg cct gct gta cct gtt gga     336
Leu Phe Pro Leu Thr Ser Thr Arg Ala Thr Pro Ala Val Pro Val Gly
            100                 105                 110 gga tgt tac agg ctt att gat atc cct atg agt aac tgc ttc aac agt     384
Gly Cys Tyr Arg Leu Ile Asp Ile Pro Met Ser Asn Cys Phe Asn Ser
```

|     |     |     |     | 115 |     |     |     | 120 |     |     |     | 125 |     |     |      |
|-----|-----|-----|-----|-----|-----|-----|-----|-----|-----|-----|-----|-----|-----|-----|------|
| ggt | ata | aat | aag | ata | ttt | gtg | atg | agt | cag | ttc | aat | tct | act | tcg | ctt  | 432
| Gly | Ile | Asn | Lys | Ile | Phe | Val | Met | Ser | Gln | Phe | Asn | Ser | Thr | Ser | Leu  |
|     | 130 |     |     |     | 135 |     |     |     | 140 |     |     |     |     |     |      |

```
aac cgc cat att cat cgt aca tac ctt gaa ggc ggg atc aac ttt gct       480
Asn Arg His Ile His Arg Thr Tyr Leu Glu Gly Gly Ile Asn Phe Ala
145             150                 155                 160 gat gga tty gta cag gta tta gcg gct aca caa atg cct gaa gag cca       528
Asp Gly Phe Val Gln Val Leu Ala Ala Thr Gln Met Pro Glu Glu Pro
                165                 170                 175 gct gga tgg ttc cag ggt aca gca gac tct atc aga aaa ttt atc tgg       576
Ala Gly Trp Phe Gln Gly Thr Ala Asp Ser Ile Arg Lys Phe Ile Trp
            180                 185                 190 gta ctc gag gat tat tac agt cac aaa tcc att gac aac att gta atc       624
Val Leu Glu Asp Tyr Tyr Ser His Lys Ser Ile Asp Asn Ile Val Ile
        195                 200                 205 ttg agt ggc gat cag ctt tat cgg atg aat tac atg gaa ctt gtg cag       672
Leu Ser Gly Asp Gln Leu Tyr Arg Met Asn Tyr Met Glu Leu Val Gln
    210                 215                 220 aaa cat gtc gag gac gat gct gat atc act ata tca tgt gct cct gtt       720
Lys His Val Glu Asp Asp Ala Asp Ile Thr Ile Ser Cys Ala Pro Val
225                 230                 235                 240 gat gag agc cga gct tct aaa aat ggg cta gtg aag att gat cat act       768
Asp Glu Ser Arg Ala Ser Lys Asn Gly Leu Val Lys Ile Asp His Thr
                245                 250                 255 gga cgt gta ctt caa ttc ttt gaa aaa cca aag ggt gct gat ttg aat       816
Gly Arg Val Leu Gln Phe Phe Glu Lys Pro Lys Gly Ala Asp Leu Asn
                260                 265                 270 tct atg aga gtt gag acc aac ttc ctg agc tat gct ata gat gat gca       864
Ser Met Arg Val Glu Thr Asn Phe Leu Ser Tyr Ala Ile Asp Asp Ala
            275                 280                 285 cag aaa tat cca tac ctt gca tca atg ggc att tat gtc ttc aag aaa       912
Gln Lys Tyr Pro Tyr Leu Ala Ser Met Gly Ile Tyr Val Phe Lys Lys
        290                 295                 300 gat gca ctt tta gac ctt ctc aag tca aaa tat act caa tta cat gac       960
Asp Ala Leu Leu Asp Leu Leu Lys Ser Lys Tyr Thr Gln Leu His Asp
305                 310                 315                 320 ttt gga tct gaa atc ctc cca aga gct gta cta gat cat agt gtg cag      1008
Phe Gly Ser Glu Ile Leu Pro Arg Ala Val Leu Asp His Ser Val Gln
                325                 330                 335 gca tgc att ttt acg ggc tat tgg gag gat gtt gga aca atc aaa tca      1056
Ala Cys Ile Phe Thr Gly Tyr Trp Glu Asp Val Gly Thr Ile Lys Ser
                340                 345                 350 ttc ttt gat gca aac ttg gcc ctc act gag cag cct tcc aag ttt gat      1104
Phe Phe Asp Ala Asn Leu Ala Leu Thr Glu Gln Pro Ser Lys Phe Asp
            355                 360                 365 ttt tac gat cca aaa aca cct ttc ttc act gca ccc cga tgc ttg cct      1152
Phe Tyr Asp Pro Lys Thr Pro Phe Phe Thr Ala Pro Arg Cys Leu Pro
        370                 375                 380 ccg acg caa ttg gac aag tgc aag atg aaa tat gca ttt atc tca gat      1200
Pro Thr Gln Leu Asp Lys Cys Lys Met Lys Tyr Ala Phe Ile Ser Asp
385                 390                 395                 400 ggt tgc tta ctg aga gaa tgc aac atc gag cat tct gtg att gga gtc      1248
Gly Cys Leu Leu Arg Glu Cys Asn Ile Glu His Ser Val Ile Gly Val
                405                 410                 415 tgc tca cgt gtc agc tct gga tgt gaa ctc aag gac tcc gtg atg atg      1296
Cys Ser Arg Val Ser Ser Gly Cys Glu Leu Lys Asp Ser Val Met Met
                420                 425                 430 gga gcg gac ath tat gaa act gaa gaa gaa gct tca aag cta ctg tta      1344
Gly Ala Asp Ile Tyr Glu Thr Glu Glu Glu Ala Ser Lys Leu Leu Leu
```

```
                        435                 440                 445
gct  ggg  aag  gtc  cca  ath  gga  ata  gga  agg  aac  aca  aag  ata  agg  aac       1392
Ala  Gly  Lys  Val  Pro  Ile  Gly  Ile  Gly  Arg  Asn  Thr  Lys  Ile  Arg  Asn
          450                      455                      460 tgt  atc  att  gac  atg  aat  gct  agg  att  ggg  aag  aac  gtg  gtg  atc  aca       1440
Cys  Ile  Ile  Asp  Met  Asn  Ala  Arg  Ile  Gly  Lys  Asn  Val  Val  Ile  Thr
465                      470                      475                      480 aac  agt  aag  ggc  atc  caa  gag  gct  gat  cac  ccg  gaa  gaa  ggg  tac  tac       1488
Asn  Ser  Lys  Gly  Ile  Gln  Glu  Ala  Asp  His  Pro  Glu  Glu  Gly  Tyr  Tyr
               485                      490                      495 ata  agg  tct  gga  atc  gtg  gtg  atc  ttg  aag  aat  gca  acc  atc  aac  gat       1536
Ile  Arg  Ser  Gly  Ile  Val  Val  Ile  Leu  Lys  Asn  Ala  Thr  Ile  Asn  Asp
          500                      505                      510 ggg  tct  gtc  ata  tag                                                              1551
Gly  Ser  Val  Ile
          515

<210> SEQ ID NO 18
<211> LENGTH: 516
<212> TYPE: PRT
<213> ORGANISM: Zea mays

<400> SEQUENCE: 18

Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
                85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Gly Ile Asn Phe Ala
145                 150                 155                 160

Asp Gly Phe Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
        195                 200                 205

Leu Ser Gly Asp Gln Leu Tyr Arg Met Asn Tyr Met Glu Leu Val Gln
    210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270
```

```
Ser Met Arg Val Glu Thr Asn Phe Leu Ser Tyr Ala Ile Asp Asp Ala
    275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp His Ser Val Gln
                325                 330                 335

Ala Cys Ile Phe Thr Gly Tyr Trp Glu Asp Val Gly Thr Ile Lys Ser
                340                 345                 350

Phe Phe Asp Ala Asn Leu Ala Leu Thr Glu Gln Pro Ser Lys Phe Asp
                355                 360                 365

Phe Tyr Asp Pro Lys Thr Pro Phe Phe Thr Ala Pro Arg Cys Leu Pro
                370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
                420                 425                 430

Gly Ala Asp Ile Tyr Glu Thr Glu Glu Ala Ser Lys Leu Leu Leu
                435                 440                 445

Ala Gly Lys Val Pro Ile Gly Ile Gly Arg Asn Thr Lys Ile Arg Asn
                450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
                500                 505                 510

Gly Ser Val Ile
        515

<210> SEQ ID NO 19
<211> LENGTH: 28
<212> TYPE: DNA
<213> ORGANISM: Artificial Sequence
<220> FEATURE:
<223> OTHER INFORMATION: oligonucleotide

<400> SEQUENCE: 19
cctgttggag gagcatacag gcttattg                                         28

<210> SEQ ID NO 20
<211> LENGTH: 28
<212> TYPE: DNA
<213> ORGANISM: Artificial Sequence
<220> FEATURE:
<223> OTHER INFORMATION: oligonucleotide

<400> SEQUENCE: 20
caataagcct gtatgctcct ccaacagg                                         28

<210> SEQ ID NO 21
<211> LENGTH: 31
<212> TYPE: DNA
<213> ORGANISM: Artificial Sequence
<220> FEATURE:
<223> OTHER INFORMATION: oligonucleotide
```

```
<400> SEQUENCE: 21
cttaaccgcc atatttctcg tacatacctt g                              31

<210> SEQ ID NO 22
<211> LENGTH: 31
<212> TYPE: DNA
<213> ORGANISM: Artificial Sequence
<220> FEATURE:
<223> OTHER INFORMATION: oligonucleotide

<400> SEQUENCE: 22
caaggtatgt acgagaaata tggcggttaa g                              31

<210> SEQ ID NO 23
<211> LENGTH: 33
<212> TYPE: DNA
<213> ORGANISM: Artificial Sequence
<220> FEATURE:
<223> OTHER INFORMATION: oligonucleotide

<400> SEQUENCE: 23
caactttgct gatggatttg tacaggtatt agc                            33

<210> SEQ ID NO 24
<211> LENGTH: 33
<212> TYPE: DNA
<213> ORGANISM: Artificial Sequence
<220> FEATURE:
<223> OTHER INFORMATION: oligonucleotide

<400> SEQUENCE: 24
gctaatacct gtacaaatcc atcagcaaag ttg                            33

<210> SEQ ID NO 25
<211> LENGTH: 28
<212> TYPE: DNA
<213> ORGANISM: Artificial Sequence
<220> FEATURE:
<223> OTHER INFORMATION: oligonucleotide

<400> SEQUENCE: 25
gcggctacac aaacgcctga agagccag                                  28

<210> SEQ ID NO 26
<211> LENGTH: 28
<212> TYPE: DNA
<213> ORGANISM: Artificial Sequence
<220> FEATURE:
<223> OTHER INFORMATION: oligonucleotide

<400> SEQUENCE: 26
ctggctcttc aggcgtttgt gtagccgc                                  28

<210> SEQ ID NO 27
<211> LENGTH: 28
<212> TYPE: DNA
<213> ORGANISM: Artificial Sequence
<220> FEATURE:
<223> OTHER INFORMATION: oligonucleotide

<400> SEQUENCE: 27
cttgagtggc gatcatcttt atcggatg                                  28

<210> SEQ ID NO 28
<211> LENGTH: 28
```

```
<212> TYPE: DNA
<213> ORGANISM: Artificial Sequence
<220> FEATURE:
<223> OTHER INFORMATION: oligonucleotide

<400> SEQUENCE: 28
catccgataa agatgatcgc cactcaag                                          28

<210> SEQ ID NO 29
<211> LENGTH: 31
<212> TYPE: DNA
<213> ORGANISM: Artificial Sequence
<220> FEATURE:
<223> OTHER INFORMATION: oligonucleotide

<400> SEQUENCE: 29
cttgtgcaga aacatcgaga ggacgatgct g                                      31

<210> SEQ ID NO 30
<211> LENGTH: 31
<212> TYPE: DNA
<213> ORGANISM: Artificial Sequence
<220> FEATURE:
<223> OTHER INFORMATION: oligonucleotide

<400> SEQUENCE: 30
cagcatcgtc ctctcgatgt ttctgcacaa g                                      31

<210> SEQ ID NO 31
<211> LENGTH: 30
<212> TYPE: DNA
<213> ORGANISM: Artificial Sequence
<220> FEATURE:
<223> OTHER INFORMATION: oligonucleotide

<400> SEQUENCE: 31
gcaaacttgg ccctctgtga gcagccttcc                                        30

<210> SEQ ID NO 32
<211> LENGTH: 30
<212> TYPE: DNA
<213> ORGANISM: Artificial Sequence
<220> FEATURE:
<223> OTHER INFORMATION: oligonucleotide

<400> SEQUENCE: 32
ggaaggctgc tcacagaggg ccaagtttgc                                        30

<210> SEQ ID NO 33
<211> LENGTH: 39
<212> TYPE: DNA
<213> ORGANISM: Artificial Sequence
<220> FEATURE:
<223> OTHER INFORMATION: oligonucleotide

<400> SEQUENCE: 33
gcagccttcc aagttttcat tttacgatcc aaaaacacc                              39

<210> SEQ ID NO 34
<211> LENGTH: 39
<212> TYPE: DNA
<213> ORGANISM: Artificial Sequence
<220> FEATURE:
<223> OTHER INFORMATION: oligonucleotide

<400> SEQUENCE: 34 ggtgttttg gatcgtaaaa tgaaaacttg gaaggctgc                               39
```

<210> SEQ ID NO 35
<211> LENGTH: 34
<212> TYPE: DNA
<213> ORGANISM: Artificial Sequence
<220> FEATURE:
<223> OTHER INFORMATION: oligonucleotide

<400> SEQUENCE: 35
gtttgatttt tacgatgcga aaacaccttt cttc                                34

<210> SEQ ID NO 36
<211> LENGTH: 34
<212> TYPE: DNA
<213> ORGANISM: Artificial Sequence
<220> FEATURE:
<223> OTHER INFORMATION: oligonucleotide

<400> SEQUENCE: 36
gaagaaaggt gttttcgcat cgtaaaaatc aaac                                34

<210> SEQ ID NO 37
<211> LENGTH: 32
<212> TYPE: DNA
<213> ORGANISM: Artificial Sequence
<220> FEATURE:
<223> OTHER INFORMATION: oligonucleotide

<400> SEQUENCE: 37
cttcactgca ccccgattct tgcctccgac gc                                  32

<210> SEQ ID NO 38
<211> LENGTH: 32
<212> TYPE: DNA
<213> ORGANISM: Artificial Sequence
<220> FEATURE:
<223> OTHER INFORMATION: oligonucleotide

<400> SEQUENCE: 38
gcgtcggagg caagaatcgg ggtgcagtga ag                                  32

<210> SEQ ID NO 39
<211> LENGTH: 32
<212> TYPE: DNA
<213> ORGANISM: Artificial Sequence
<220> FEATURE:
<223> OTHER INFORMATION: oligonucleotide

<400> SEQUENCE: 39
cgtgtcagct ctggagttga actcaaggac tc                                  32

<210> SEQ ID NO 40
<211> LENGTH: 32
<212> TYPE: DNA
<213> ORGANISM: Artificial Sequence
<220> FEATURE:
<223> OTHER INFORMATION: oligonucleotide

<400> SEQUENCE: 40
gagtccttga gttcaactcc agagctgaca cg                                  32

<210> SEQ ID NO 41
<211> LENGTH: 28
<212> TYPE: DNA
<213> ORGANISM: Artificial Sequence
<220> FEATURE:
<223> OTHER INFORMATION: oligonucleotide

<400> SEQUENCE: 41
gcggacatct atcaaactga agaagaag                28

<210> SEQ ID NO 42
<211> LENGTH: 28
<212> TYPE: DNA
<213> ORGANISM: Artificial Sequence
<220> FEATURE:
<223> OTHER INFORMATION: oligonucleotide

<400> SEQUENCE: 42
cttcttcttc agtttgatag atgtccgc                28

<210> SEQ ID NO 43
<211> LENGTH: 26
<212> TYPE: DNA
<213> ORGANISM: Artificial Sequence
<220> FEATURE:
<223> OTHER INFORMATION: oligonucleotide

<400> SEQUENCE: 43
ggtctggaat cacggtgatc ctgaag                  26

<210> SEQ ID NO 44
<211> LENGTH: 26
<212> TYPE: DNA
<213> ORGANISM: Artificial Sequence
<220> FEATURE:
<223> OTHER INFORMATION: oligonucleotide

<400> SEQUENCE: 44
cttcaggatc accgtgattc cagacc                  26

<210> SEQ ID NO 45
<211> LENGTH: 29
<212> TYPE: DNA
<213> ORGANISM: Artificial Sequence
<220> FEATURE:
<223> OTHER INFORMATION: oligonucleotide

<400> SEQUENCE: 45
gatcctgaag aattcaacca tcaacgatg               29

<210> SEQ ID NO 46
<211> LENGTH: 29
<212> TYPE: DNA
<213> ORGANISM: Artificial Sequence
<220> FEATURE:
<223> OTHER INFORMATION: oligonucleotide

<400> SEQUENCE: 46
catcgttgat ggttgaattc ttcaggatc               29

<210> SEQ ID NO 47
<211> LENGTH: 1551
<212> TYPE: DNA
<213> ORGANISM: Zea mays
<220> FEATURE:
<221> NAME/KEY: exon
<222> LOCATION: (1)..(1551)
<220> FEATURE:
<221> NAME/KEY: misc_feature
<222> LOCATION: (489)..(489)
<223> OTHER INFORMATION: y = t or c
<220> FEATURE:
<221> NAME/KEY: misc_feature
<222> LOCATION: (1272)..(1272)

```
<223> OTHER INFORMATION: n is a, c, g, or t
<220> FEATURE:
<221> NAME/KEY: misc_feature
<222> LOCATION: (1308)..(1308)
<223> OTHER INFORMATION: h = a, c, or t
<220> FEATURE:
<221> NAME/KEY: misc_feature
<222> LOCATION: (1362)..(1362)
<223> OTHER INFORMATION: h = a, c, or t

<400> SEQUENCE: 47
```

| | | | | | | | | | | | | | | | | |
|---|---|---|---|---|---|---|---|---|---|---|---|---|---|---|---|---|
| atg | cag | ttt | gca | ctt | gca | ttg | gac | acg | aac | tca | ggt | cct | cac | cag | ata | 48 |
| Met | Gln | Phe | Ala | Leu | Ala | Leu | Asp | Thr | Asn | Ser | Gly | Pro | His | Gln | Ile | |
| 1 | | | | 5 | | | | | 10 | | | | | 15 | | |
| aga | tct | tgt | gag | ggt | gat | ggg | att | gac | agg | ttg | gaa | aaa | tta | agt | att | 96 |
| Arg | Ser | Cys | Glu | Gly | Asp | Gly | Ile | Asp | Arg | Leu | Glu | Lys | Leu | Ser | Ile | |
| | | 20 | | | | | 25 | | | | | 30 | | | | |
| ggg | ggc | aga | aag | cag | gag | aaa | gct | ttg | aga | aat | agg | tgc | ttt | ggt | ggt | 144 |
| Gly | Gly | Arg | Lys | Gln | Glu | Lys | Ala | Leu | Arg | Asn | Arg | Cys | Phe | Gly | Gly | |
| | 35 | | | | | 40 | | | | | 45 | | | | | |
| aga | gtt | gct | gca | act | aca | caa | tgt | att | ctt | acc | tca | gat | gct | tgt | cct | 192 |
| Arg | Val | Ala | Ala | Thr | Thr | Gln | Cys | Ile | Leu | Thr | Ser | Asp | Ala | Cys | Pro | |
| | 50 | | | | | 55 | | | | | 60 | | | | | |
| gaa | act | ctt | cat | tct | caa | aca | cag | tcc | tct | agg | aaa | aat | tat | gct | gat | 240 |
| Glu | Thr | Leu | His | Ser | Gln | Thr | Gln | Ser | Ser | Arg | Lys | Asn | Tyr | Ala | Asp | |
| 65 | | | | | 70 | | | | | 75 | | | | | 80 | |
| gca | aac | cgt | gta | tct | gct | atc | att | ttg | ggc | gga | ggc | act | gga | tct | cag | 288 |
| Ala | Asn | Arg | Val | Ser | Ala | Ile | Ile | Leu | Gly | Gly | Gly | Thr | Gly | Ser | Gln | |
| | | | | 85 | | | | | 90 | | | | | 95 | | |
| ctc | ttt | cct | ctg | aca | agc | aca | aga | gct | acg | cct | gct | gta | cct | gtt | gga | 336 |
| Leu | Phe | Pro | Leu | Thr | Ser | Thr | Arg | Ala | Thr | Pro | Ala | Val | Pro | Val | Gly | |
| | | | 100 | | | | | 105 | | | | | 110 | | | |
| gga | tgt | tac | agg | ctt | att | gat | atc | cct | atg | agt | aac | tgc | ttc | aac | agt | 384 |
| Gly | Cys | Tyr | Arg | Leu | Ile | Asp | Ile | Pro | Met | Ser | Asn | Cys | Phe | Asn | Ser | |
| | | | 115 | | | | | 120 | | | | | 125 | | | |
| ggt | ata | aat | aag | ata | ttt | gtg | atg | agt | cag | ttc | aat | tct | act | tcg | ctt | 432 |
| Gly | Ile | Asn | Lys | Ile | Phe | Val | Met | Ser | Gln | Phe | Asn | Ser | Thr | Ser | Leu | |
| | 130 | | | | | 135 | | | | | 140 | | | | | |
| aac | cgc | cat | att | cat | cgt | aca | tac | ctt | gaa | ggc | ggg | atc | aac | ttt | gct | 480 |
| Asn | Arg | His | Ile | His | Arg | Thr | Tyr | Leu | Glu | Gly | Gly | Ile | Asn | Phe | Ala | |
| 145 | | | | | 150 | | | | | 155 | | | | | 160 | |
| gat | gga | tty | gta | cag | gta | tta | gcg | gct | aca | caa | atg | cct | gaa | gag | cca | 528 |
| Asp | Gly | Phe | Val | Gln | Val | Leu | Ala | Ala | Thr | Gln | Met | Pro | Glu | Glu | Pro | |
| | | | | 165 | | | | | 170 | | | | | 175 | | |
| gct | gga | tgg | ttc | cag | ggt | aca | gca | gac | tct | atc | aga | aaa | ttt | atc | tgg | 576 |
| Ala | Gly | Trp | Phe | Gln | Gly | Thr | Ala | Asp | Ser | Ile | Arg | Lys | Phe | Ile | Trp | |
| | | | 180 | | | | | 185 | | | | | 190 | | | |
| gta | ctc | gag | gat | tat | tac | agt | cac | aaa | tcc | att | gac | aac | att | gta | atc | 624 |
| Val | Leu | Glu | Asp | Tyr | Tyr | Ser | His | Lys | Ser | Ile | Asp | Asn | Ile | Val | Ile | |
| | | | 195 | | | | | 200 | | | | | 205 | | | |
| ttg | agt | ggc | gat | cag | ctt | tat | cgg | atg | aat | tac | atg | gaa | ctt | gtg | cag | 672 |
| Leu | Ser | Gly | Asp | Gln | Leu | Tyr | Arg | Met | Asn | Tyr | Met | Glu | Leu | Val | Gln | |
| | 210 | | | | | 215 | | | | | 220 | | | | | |
| aaa | cat | gtc | gag | gac | gat | gct | gat | atc | act | ata | tca | tgt | gct | cct | gtt | 720 |
| Lys | His | Val | Glu | Asp | Asp | Ala | Asp | Ile | Thr | Ile | Ser | Cys | Ala | Pro | Val | |
| 225 | | | | | 230 | | | | | 235 | | | | | 240 | |
| gat | gag | agc | cga | gct | tct | aaa | aat | ggg | cta | gtg | aag | att | gat | cat | act | 768 |
| Asp | Glu | Ser | Arg | Ala | Ser | Lys | Asn | Gly | Leu | Val | Lys | Ile | Asp | His | Thr | |
| | | | 245 | | | | | 250 | | | | | 255 | | | |
| gga | cgt | gta | ctt | caa | ttc | ttt | gaa | aaa | cca | aag | ggt | gct | gat | ttg | aat | 816 |
| Gly | Arg | Val | Leu | Gln | Phe | Phe | Glu | Lys | Pro | Lys | Gly | Ala | Asp | Leu | Asn | |
| | 260 | | | | | 265 | | | | | 270 | | | | | |

```
tct atg aga gtt gag acc aac ttc ctg agc tat gct ata gat gat gca    864
Ser Met Arg Val Glu Thr Asn Phe Leu Ser Tyr Ala Ile Asp Asp Ala
    275                 280                 285 cag aaa tat cca tac ctt gca tca atg ggc att tat gtc ttc aag aaa    912
Gln Lys Tyr Pro Tyr Leu Ala Ser Met Gly Ile Tyr Val Phe Lys Lys
290                 295                 300 gat gca ctt tta gac ctt ctc aag tca aaa tat act caa tta cat gac    960
Asp Ala Leu Leu Asp Leu Leu Lys Ser Lys Tyr Thr Gln Leu His Asp
305                 310                 315                 320 ttt gga tct gaa atc ctc cca aga gct gta cta gat cat agt gtg cag   1008
Phe Gly Ser Glu Ile Leu Pro Arg Ala Val Leu Asp His Ser Val Gln
                325                 330                 335 gca tgc att ttt acg ggc tat tgg gag gat gtt gga aca atc aaa tca   1056
Ala Cys Ile Phe Thr Gly Tyr Trp Glu Asp Val Gly Thr Ile Lys Ser
            340                 345                 350 ttc ttt gat gca aac ttg gcc ctc act gag cag cct tcc aag ttt gat   1104
Phe Phe Asp Ala Asn Leu Ala Leu Thr Glu Gln Pro Ser Lys Phe Asp
        355                 360                 365 ttt tac gat cca aaa aca cct ttc ttc act gca ccc cga tgc ttg cct   1152
Phe Tyr Asp Pro Lys Thr Pro Phe Phe Thr Ala Pro Arg Cys Leu Pro
370                 375                 380 ccg acg caa ttg gac aag tgc aag atg aaa tat gca ttt atc tca gat   1200
Pro Thr Gln Leu Asp Lys Cys Lys Met Lys Tyr Ala Phe Ile Ser Asp
385                 390                 395                 400 ggt tgc tta ctg aga gaa tgc aac atc gag cat tct gtg att gga gtc   1248
Gly Cys Leu Leu Arg Glu Cys Asn Ile Glu His Ser Val Ile Gly Val
                405                 410                 415 tgc tca cgt gtc agc tct gga gtn gaa ctc aag gac tcc gtg atg atg   1296
Cys Ser Arg Val Ser Ser Gly Val Glu Leu Lys Asp Ser Val Met Met
            420                 425                 430 gga gcg gac ath tat gaa act gaa gaa gaa gct tca aag cta ctg tta   1344
Gly Ala Asp Ile Tyr Glu Thr Glu Glu Glu Ala Ser Lys Leu Leu Leu
        435                 440                 445 gct ggg aag gtc cca ath gga ata gga agg aac aca aag ata agg aac   1392
Ala Gly Lys Val Pro Ile Gly Ile Gly Arg Asn Thr Lys Ile Arg Asn
450                 455                 460 tgt atc att gac atg aat gct agg att ggg aag aac gtg gtg atc aca   1440
Cys Ile Ile Asp Met Asn Ala Arg Ile Gly Lys Asn Val Val Ile Thr
465                 470                 475                 480 aac agt aag ggc atc caa gag gct gat cac ccg gaa gaa ggg tac tac   1488
Asn Ser Lys Gly Ile Gln Glu Ala Asp His Pro Glu Glu Gly Tyr Tyr
                485                 490                 495 ata agg tct gga atc gtg gtg atc ttg aag aat gca acc atc aac gat   1536
Ile Arg Ser Gly Ile Val Val Ile Leu Lys Asn Ala Thr Ile Asn Asp
            500                 505                 510 ggg tct gtc ata tag                                                1551
Gly Ser Val Ile
        515

<210> SEQ ID NO 48
<211> LENGTH: 1551
<212> TYPE: DNA
<213> ORGANISM: Zea mays
<220> FEATURE:
<221> NAME/KEY: exon
<222> LOCATION: (1)..(1551)
<220> FEATURE:
<221> NAME/KEY: misc_feature
<222> LOCATION: (1308)..(1308)
<223> OTHER INFORMATION: h = a, c, or t
<220> FEATURE:
<221> NAME/KEY: misc_feature
<222> LOCATION: (1362)..(1362)
<223> OTHER INFORMATION: h = a, c, or t
```

<400> SEQUENCE: 48

| | | |
|---|---|---|
| atg cag ttt gca ctt gca ttg gac acg aac tca ggt cct cac cag ata<br>Met Gln Phe Ala Leu Ala Leu Asp Thr Asn Ser Gly Pro His Gln Ile<br>1                        5                        10                       15 | | 48 |
| aga tct tgt gag ggt gat ggg att gac agg ttg gaa aaa tta agt att<br>Arg Ser Cys Glu Gly Asp Gly Ile Asp Arg Leu Glu Lys Leu Ser Ile<br>                    20                       25                       30 | | 96 |
| ggg ggc aga aag cag gag aaa gct ttg aga aat agg tgc ttt ggt ggt<br>Gly Gly Arg Lys Gln Glu Lys Ala Leu Arg Asn Arg Cys Phe Gly Gly<br>35                        40                        45 | | 144 |
| aga gtt gct gca act aca caa tgt att ctt acc tca gat gct tgt cct<br>Arg Val Ala Ala Thr Thr Gln Cys Ile Leu Thr Ser Asp Ala Cys Pro<br>    50                        55                       60 | | 192 |
| gaa act ctt cat tct caa aca cag tcc tct agg aaa aat tat gct gat<br>Glu Thr Leu His Ser Gln Thr Gln Ser Ser Arg Lys Asn Tyr Ala Asp<br>65                        70                        75                       80 | | 240 |
| gca aac cgt gta tct gct atc att ttg ggc gga ggc act gga tct cag<br>Ala Asn Arg Val Ser Ala Ile Ile Leu Gly Gly Gly Thr Gly Ser Gln<br>                    85                       90                       95 | | 288 |
| ctc ttt cct ctg aca agc aca aga gct acg cct gct gta cct gtt gga<br>Leu Phe Pro Leu Thr Ser Thr Arg Ala Thr Pro Ala Val Pro Val Gly<br>                  100                     105                   110 | | 336 |
| gga tgt tac agg ctt att gat atc cct atg agt aac tgc ttc aac agt<br>Gly Cys Tyr Arg Leu Ile Asp Ile Pro Met Ser Asn Cys Phe Asn Ser<br>115                     120                     125 | | 384 |
| ggt ata aat aag ata ttt gtg atg agt cag ttc aat tct act tcg ctt<br>Gly Ile Asn Lys Ile Phe Val Met Ser Gln Phe Asn Ser Thr Ser Leu<br>      130                   135                     140 | | 432 |
| aac cgc cat att cat cgt aca tac ctt gaa ggc ggg atc aac ttt gct<br>Asn Arg His Ile His Arg Thr Tyr Leu Glu Gly Gly Ile Asn Phe Ala<br>145                     150                     155                     160 | | 480 |
| gat gga tct gta cag gta tta gcg gct aca caa atg cct gaa gag cca<br>Asp Gly Ser Val Gln Val Leu Ala Ala Thr Gln Met Pro Glu Glu Pro<br>                  165                     170                   175 | | 528 |
| gct gga tgg ttc cag ggt aca gca gac tct atc aga aaa ttt atc tgg<br>Ala Gly Trp Phe Gln Gly Thr Ala Asp Ser Ile Arg Lys Phe Ile Trp<br>                180                     185                   190 | | 576 |
| gta ctc gag gat tat tac agt cac aaa tcc att gac aac att gta atc<br>Val Leu Glu Asp Tyr Tyr Ser His Lys Ser Ile Asp Asn Ile Val Ile<br>     195                   200                     205 | | 624 |
| ttg agt ggc gat cag ctt tat cgg atg aat tac atg gaa ctt gtg cag<br>Leu Ser Gly Asp Gln Leu Tyr Arg Met Asn Tyr Met Glu Leu Val Gln<br>210                     215                     220 | | 672 |
| aaa cat gtc gag gac gat gct gat atc act ata tca tgt gct cct gtt<br>Lys His Val Glu Asp Asp Ala Asp Ile Thr Ile Ser Cys Ala Pro Val<br>225                     230                     235                    240 | | 720 |
| gat gag agc cga gct tct aaa aat ggg cta gtg aag att gat cat act<br>Asp Glu Ser Arg Ala Ser Lys Asn Gly Leu Val Lys Ile Asp His Thr<br>                  245                     250                   255 | | 768 |
| gga cgt gta ctt caa ttc ttt gaa aaa cca aag ggt gct gat ttg aat<br>Gly Arg Val Leu Gln Phe Phe Glu Lys Pro Lys Gly Ala Asp Leu Asn<br>                260                     265                   270 | | 816 |
| tct atg aga gtt gag acc aac ttc ctg agc tat gct ata gat gat gca<br>Ser Met Arg Val Glu Thr Asn Phe Leu Ser Tyr Ala Ile Asp Asp Ala<br>     275                   280                     285 | | 864 |
| cag aaa tat cca tac ctt gca tca atg ggc att tat gtc ttc aag aaa<br>Gln Lys Tyr Pro Tyr Leu Ala Ser Met Gly Ile Tyr Val Phe Lys Lys<br>290                     295                     300 | | 912 |
| gat gca ctt tta gac ctt ctc aag tca aaa tat act caa tta cat gac | | 960 |

```
Asp Ala Leu Leu Asp Leu Leu Lys Ser Lys Tyr Thr Gln Leu His Asp
305                 310                 315                 320 ttt gga tct gaa atc ctc cca aga gct gta cta gat cat agt gtg cag      1008
Phe Gly Ser Glu Ile Leu Pro Arg Ala Val Leu Asp His Ser Val Gln
                325                 330                 335 gca tgc att ttt acg ggc tat tgg gag gat gtt gga aca atc aaa tca      1056
Ala Cys Ile Phe Thr Gly Tyr Trp Glu Asp Val Gly Thr Ile Lys Ser
            340                 345                 350 ttc ttt gat gca aac ttg gcc ctc act gag cag cct tcc aag ttt gat      1104
Phe Phe Asp Ala Asn Leu Ala Leu Thr Glu Gln Pro Ser Lys Phe Asp
        355                 360                 365 ttt tac gat cca aaa aca cct ttc ttc act gca ccc cga tgc ttg cct      1152
Phe Tyr Asp Pro Lys Thr Pro Phe Phe Thr Ala Pro Arg Cys Leu Pro
    370                 375                 380 ccg acg caa ttg gac aag tgc aag atg aaa tat gca ttt atc tca gat      1200
Pro Thr Gln Leu Asp Lys Cys Lys Met Lys Tyr Ala Phe Ile Ser Asp
385                 390                 395                 400 ggt tgc tta ctg aga gaa tgc aac atc gag cat tct gtg att gga gtc      1248
Gly Cys Leu Leu Arg Glu Cys Asn Ile Glu His Ser Val Ile Gly Val
                405                 410                 415 tgc tca cgt gtc agc tct gga tgt gaa ctc aag gac tcc gtg atg atg      1296
Cys Ser Arg Val Ser Ser Gly Cys Glu Leu Lys Asp Ser Val Met Met
            420                 425                 430 gga gcg gac ath tat gaa act gaa gaa gaa gct tca aag cta ctg tta      1344
Gly Ala Asp Ile Tyr Glu Thr Glu Glu Glu Ala Ser Lys Leu Leu Leu
        435                 440                 445 gct ggg aag gtc cca ath gga ata gga agg aac aca aag ata agg aac      1392
Ala Gly Lys Val Pro Ile Gly Ile Gly Arg Asn Thr Lys Ile Arg Asn
    450                 455                 460 tgt atc att gac atg aat gct agg att ggg aag aac gtg gtg atc aca      1440
Cys Ile Ile Asp Met Asn Ala Arg Ile Gly Lys Asn Val Val Ile Thr
465                 470                 475                 480 aac agt aag ggc atc caa gag gct gat cac ccg gaa gaa ggg tac tac      1488
Asn Ser Lys Gly Ile Gln Glu Ala Asp His Pro Glu Glu Gly Tyr Tyr
                485                 490                 495 ata agg tct gga atc gtg gtg atc ttg aag aat gca acc atc aac gat      1536
Ile Arg Ser Gly Ile Val Val Ile Leu Lys Asn Ala Thr Ile Asn Asp
            500                 505                 510 ggg tct gtc ata tag                                                   1551
Gly Ser Val Ile
        515

<210> SEQ ID NO 49
<211> LENGTH: 516
<212> TYPE: PRT
<213> ORGANISM: Zea mays

<400> SEQUENCE: 49

Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Gly Thr Gly Ser Gln
                85                  90                  95
```

```
Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
            115                 120                 125

Gly Ile Asn Lys Ile Phe Val Met Ser Gln Phe Asn Ser Thr Ser Leu
            130                 135                 140

Asn Arg His Ile His Arg Thr Tyr Leu Glu Gly Gly Ile Asn Phe Ala
145                 150                 155                 160

Asp Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
            195                 200                 205

Leu Ser Gly Asp Gln Leu Tyr Arg Met Asn Tyr Met Glu Leu Val Gln
            210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270

Ser Met Arg Val Glu Thr Asn Phe Leu Ser Tyr Ala Ile Asp Asp Ala
            275                 280                 285

Gln Lys Tyr Pro Tyr Leu Ala Ser Met Gly Ile Tyr Val Phe Lys Lys
            290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp His Ser Val Gln
                325                 330                 335

Ala Cys Ile Phe Thr Gly Tyr Trp Glu Asp Val Gly Thr Ile Lys Ser
            340                 345                 350

Phe Phe Asp Ala Asn Leu Ala Leu Thr Glu Gln Pro Ser Lys Phe Asp
            355                 360                 365

Phe Tyr Asp Pro Lys Thr Pro Phe Phe Thr Ala Pro Arg Cys Leu Pro
            370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
            420                 425                 430

Gly Ala Asp Ile Tyr Glu Thr Glu Glu Ala Ser Lys Leu Leu Leu
            435                 440                 445

Ala Gly Lys Val Pro Ile Gly Ile Gly Arg Asn Thr Lys Ile Arg Asn
            450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
            500                 505                 510

Gly Ser Val Ile
```

<210> SEQ ID NO 50
<211> LENGTH: 470
<212> TYPE: PRT
<213> ORGANISM: Solanum tuberosum

<400> SEQUENCE: 50

Asn Lys Ile Lys Pro Gly Val Ala Tyr Ser Val Ile Thr Thr Glu Asn
1               5                   10                  15

Asp Thr Gln Thr Val Phe Val Asp Met Pro Arg Leu Glu Arg Arg Arg
                20                  25                  30

Ala Asn Pro Lys Asp Val Ala Ala Val Ile Leu Gly Gly Gly Glu Gly
                35                  40                  45

Thr Lys Leu Phe Pro Leu Thr Ser Arg Thr Ala Thr Pro Ala Val Pro
50                  55                  60

Val Gly Gly Cys Tyr Arg Leu Ile Asp Ile Pro Met Ser Asn Cys Ile
65                  70                  75                  80

Asn Ser Ala Ile Asn Lys Ile Phe Val Leu Thr Gln Tyr Asn Ser Ala
                85                  90                  95

Pro Leu Asn Arg His Ile Ala Arg Thr Tyr Phe Gly Asn Gly Val Ser
                100                 105                 110

Phe Gly Asp Gly Phe Val Glu Val Leu Ala Ala Thr Gln Thr Pro Gly
                115                 120                 125

Glu Ala Gly Lys Lys Trp Phe Gln Gly Thr Ala Asp Ala Val Arg Lys
                130                 135                 140

Phe Ile Trp Val Phe Glu Asp Ala Lys Asn Lys Asn Ile Glu Asn Ile
145                 150                 155                 160

Val Val Leu Ser Gly Asp His Leu Tyr Arg Met Asp Tyr Met Glu Leu
                165                 170                 175

Val Gln Asn His Ile Asp Arg Asn Ala Asp Ile Thr Leu Ser Cys Ala
                180                 185                 190

Pro Ala Glu Asp Ser Arg Ala Ser Asp Phe Gly Leu Val Lys Ile Asp
                195                 200                 205

Ser Arg Gly Arg Val Val Gln Phe Ala Glu Lys Pro Lys Gly Phe Asp
210                 215                 220

Leu Lys Ala Met Gln Val Asp Thr Thr Leu Val Gly Leu Ser Pro Gln
225                 230                 235                 240

Asp Ala Lys Lys Ser Pro Tyr Ile Ala Ser Met Gly Val Tyr Val Phe
                245                 250                 255

Lys Thr Asp Val Leu Leu Lys Leu Leu Lys Trp Ser Tyr Pro Thr Ser
                260                 265                 270

Asn Asp Phe Gly Ser Glu Ile Ile Pro Ala Ala Ile Asp Asp Tyr Asn
                275                 280                 285

Val Gln Ala Tyr Ile Phe Lys Asp Tyr Trp Glu Asp Ile Gly Thr Ile
                290                 295                 300

Lys Ser Phe Tyr Asn Ala Ser Leu Ala Leu Thr Gln Glu Phe Pro Glu
305                 310                 315                 320

Phe Gln Phe Tyr Asp Pro Lys Thr Pro Phe Tyr Thr Ser Pro Arg Phe
                325                 330                 335

Leu Pro Pro Thr Lys Ile Asp Asn Cys Lys Ile Lys Asp Ala Ile Ile
                340                 345                 350

Ser His Gly Cys Phe Leu Arg Asp Cys Ser Val Glu His Ser Ile Val
                355                 360                 365

Gly Glu Arg Ser Arg Leu Asp Cys Gly Val Glu Leu Lys Asp Thr Phe

-continued

```
              370                 375                 380
Met Met Gly Ala Asp Tyr Tyr Gln Thr Glu Ser Glu Ile Ala Ser Leu
385                 390                 395                 400

Leu Ala Glu Gly Lys Val Pro Ile Gly Ile Gly Glu Asn Thr Lys Ile
                405                 410                 415

Arg Lys Cys Ile Ile Asp Lys Asn Ala Lys Ile Gly Lys Asn Val Ser
                420                 425                 430

Ile Ile Asn Lys Asp Gly Val Gln Glu Ala Asp Arg Pro Glu Glu Gly
            435                 440                 445

Phe Tyr Ile Arg Ser Gly Ile Ile Ile Ile Leu Glu Lys Ala Thr Ile
        450                 455                 460

Arg Asp Gly Thr Val Ile
465                 470
```

METHODS AND MATERIALS FOR INCREASING STARCH BIOSYNTHESIS IN PLANTS

GOVERNMENT SUPPORT

The subject matter of this application has been supported by a research grant from the National Science Foundation under grant numbers IOS-0444031 and IOS-0815104. Accordingly, the government has certain rights in this invention.

BACKGROUND OF THE INVENTION

AGPase catalyzes the first committed step in starch (plants) and glycogen (bacteria) synthesis. It involves the conversion of glucose-1-P (G-1-P) and ATP to ADP-glucose and pyrophosphate (PPi). AGPase is a heterotetramer in plants consisting of two identical small and two identical large subunits. The large and the small subunits are encoded by shrunken-2 (Sh2) and brittle-2 (Bt2) respectively in maize endosperm. AGPase is allosterically regulated by small effector molecules that are indicative of the energy status of the cell. AGPase is activated by 3-PGA, the first carbon assimilatory product, and inhibited/deactivated by inorganic phosphate (Pi) in cyanobacteria, green algae and angiosperms.

The importance of maize endosperm AGPase in starch synthesis has been shown by the kernel phenotype of mutants in either subunit of the enzyme. Indeed, such mutants result in shrunken kernels and a large reduction in endosperm starch content (Tsai and Nelson, 1966; Hannah and Nelson, 1976). There is also evidence that AGPase catalyses a rate-limiting step in starch synthesis (Stark et al. 1992; Giroux et al. 1996; Greene et al 1998b; Sakulsingharoja et al. 2004; Obana et al. 2006; Wang et al. 2007).

Greene and Hannah (1998a) isolated a mutant form of maize AGPase with a single amino acid change in the large subunit termed HS33. They showed that the altered enzyme was more heat-stable and that stability was due to stronger subunit-subunit interactions. When wheat and rice were transformed with a Sh2 variant that contains the HS33 change along with a change that affects the allosteric properties of AGPase (Rev6)(Giroux et al., 1996), yield was increased by 38% and 23% respectively (Smidansky et al., 2002; 2003). Remarkably, the increase was due to an increase in seed number rather than individual seed weight.

Transformation of maize with the Sh2 variant containing the Rev6 and HS33 changes also gives rise to enhanced seed number. Seed yield/ear can be increased up to 68% in maize. Enhanced seed number cannot be explained by Rev6 since, when expressed alone in maize, it increases only seed weight (Hannah, unpublished). The above studies show the importance of AGPase heat stability in cereal yield.

Cross et al. (2004) generated a mosaic small subunit (MP) consisting of the first 200 amino acids of BT2 and the last 275 amino acids of the potato tuber small subunit. MP in a complex with SH2 had several features that could lead to agronomic gain (Cross et al., 2004; Boehlein et al., 2005). Some of those features were increased activity in the absence of the activator 3-PGA, increased affinity for 3-PGA and elevated heat stability compared to wildtype maize endosperm AGPase (BT2/SH2). Preliminary data show that maize plants with transgenic MP containing AGPase variant expressed in maize endosperm provides for a starch yield increase (Hannah, unpublished data).

BRIEF SUMMARY OF THE INVENTION

The subject invention concerns materials and methods for providing plants or plant tissue with increased starch biosynthesis. Increased starch biosynthesis provides for increased yield. One aspect of the invention concerns polynucleotides that encode a mutant plant large subunit of AGPase. In one embodiment, a polynucleotide of the invention encodes a plant AGPase large subunit having an amino acid mutation wherein the cysteine amino acid corresponding to amino acid position 424 of wild type maize AGPase large subunit is substituted with an amino acid that results in increased AGPase activity when provided in an AGPase enzyme. In a specific embodiment, the cysteine corresponding to amino acid position 424 of wild type maize AGPase large subunit is substituted with a valine amino acid. The subject invention also comprises a mutant plant large subunit of AGPase encoded by a polynucleotide of the invention. Characterization of kinetic and allosteric properties indicates increased starch yield is provided when the polynucleotides of the invention are expressed in plants such as monocot endosperms.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows an amino acid alignment between maize endosperm (SH2) and potato tuber large subunit. Red boxes indicate sites that make direct contact with the small subunit as determined by Tuncel et al. (2008). Blue and red arrows indicate type-II and positively selected sites respectively.

FIG. 5A shows areas that participate in tail-to-tail interactions. FIG. 5B shows areas that participate in head-to-head interactions.

Figure 7:
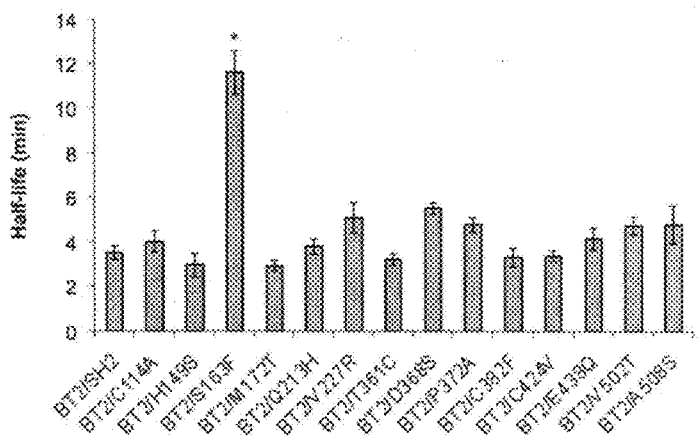

FIG. 7 shows heat stability of SH2 wild type and variants in a complex with BT2. * indicates significant difference compared to wild type BT2/SH2 at p=0.05 (Student t-test) (N=6).

Figure 8:
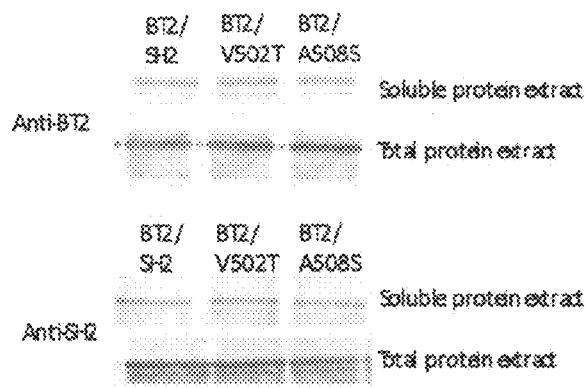

FIG. 8 shows Western blot of protein extracts from *E. coli* cells expressing SH2, V502T, and A508S along with BT2.

Figure 9:
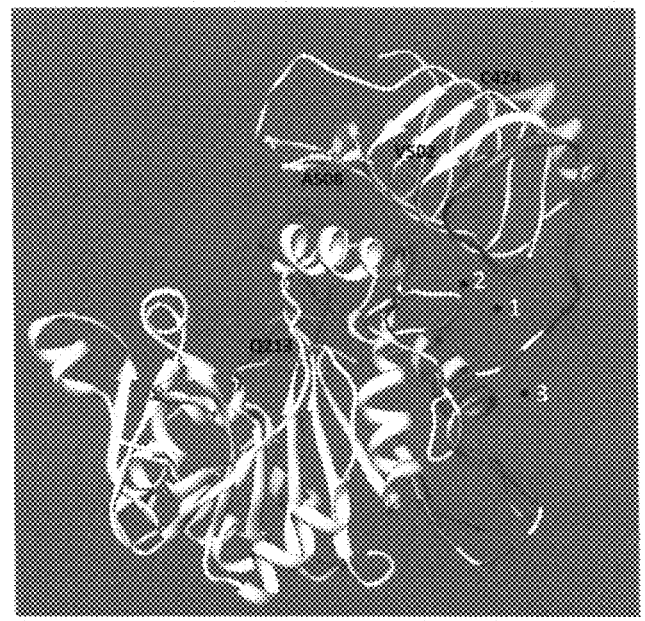

FIG. 9 shows placement of SH2 sites 213, 424, 502 and 508 on the modeled SH2 structure. SH2 modeled structure (magenta) was superimposed on potato tuber large subunit modeled structure (white). Red areas indicate sites in the potato tuber large subunit that are proposed to make direct contact with the small subunit (Tuncel et al., 2008). Red circles indicate the candidate Pi binding sites.

BRIEF DESCRIPTION OF THE SEQUENCES

SEQ ID NO:1 is a polynucleotide sequence comprising a nucleotide sequence encoding a mutant plant large subunit AGPase polypeptide of the invention.

SEQ ID NO:2 is an amino acid sequence of a mutant polypeptide of the invention encoded by SEQ ID NO:1.

SEQ ID NOs:3, 4, and 5 are polynucleotide sequences encoding a mutant plant AGPase small subunit that can be used according to the present invention.

SEQ ID NOs:6, 7, and 8 are amino acid sequences of a mutant plant AGPase small subunit that can be used according to the present invention and that is encoded by SEQ ID NOs: 3, 4, and 5, respectively.

SEQ ID NO:9 is a polynucleotide sequence encoding a mutant plant AGPase small subunit that can be used according to the present invention.

SEQ ID NO:10 is an amino acid sequence of a mutant plant AGPase small subunit that can be used according to the present invention.

SEQ ID NO:11 is an amino acid sequence of a mutant plant AGPase small subunit that can be used according to the present invention.

SEQ ID NO:12 is a polynucleotide sequence encoding a mutant plant AGPase small subunit that can be used according to the present invention.

SEQ ID NO:13 is an amino acid sequence of a mutant plant AGPase small subunit that can be used according to the present invention and that is encoded by SEQ ID NO:12.

SEQ ID NO:14 is an amino acid sequence of a mutant plant AGPase large subunit polypeptide of the invention.

SEQ ID NO:15 is an amino acid sequence of a mutant plant AGPase large subunit polypeptide of the invention.

SEQ ID NO:16 is an amino acid sequence of a mutant plant AGPase large subunit polypeptide of the invention.

SEQ ID NO:17 is a polynucleotide sequence comprising a nucleotide sequence encoding a mutant plant large subunit AGPase polypeptide of the invention.

SEQ ID NO:18 is an amino acid sequence of a mutant plant AGPase large subunit polypeptide of the invention encoded by SEQ ID NO:17.

SEQ ID NOs:19-46 are oligonucleotides that can be used according to the present invention.

SEQ ID NO:47 is a polynucleotide sequence comprising a nucleotide sequence encoding the mutant plant large subunit AGPase polypeptide of the invention.

SEQ ID NO:48 is a polynucleotide sequence comprising a nucleotide sequence encoding a wild type plant large subunit AGPase polypeptide.

SEQ ID NO:49 is an amino acid sequence of a wild type maize endosperm large subunit AGPase polypeptide.

SEQ ID NO:50 is an amino acid sequence of a wild type potato tuber large subunit AGPase polypeptide.

DETAILED DESCRIPTION OF THE INVENTION

The subject invention concerns materials and methods for providing plants with increased starch production. One aspect of the invention concerns polynucleotides that encode a mutant plant large subunit of AGPase. In one embodiment, a polynucleotide of the invention encodes a plant AGPase large subunit having an amino acid mutation wherein the cysteine amino acid corresponding to amino acid position 424 of wild type maize endosperm AGPase large subunit is substituted with an amino acid that results in increased AGPase activity when provided in an AGPase enzyme. In a specific embodiment, the amino acid substituted for the cysteine is a valine. In an exemplified embodiment, the mutant plant AGPase large subunit encoded by the polynucleotide comprises the amino acid sequence shown in SEQ ID NO:2, or a fragment or variant thereof that exhibits substantially the same activity as a full-length amino acid sequence. In a specific embodiment, the polynucleotide comprises the nucleotide sequence shown in SEQ ID NO:1, or a fragment or variant thereof.

Polynucleotides of the invention encoding a mutant plant large subunit of AGPase can also optionally comprise any one of the mutations described in any of U.S. Pat. Nos. 5,589,618; 5,650,557; 5,872,216; 6,069,300; 6,184,438; 6,403,863; 6,809,235; 7,173,165; 7,312,378; and 6,969,783. In one embodiment, a mutant large subunit of the invention comprises a Rev6 mutation as described in U.S. Pat. Nos. 5,872,216; 5,650,557; and 5,589,618, and International published application number WO 98/10082, and/or one or more heat stable (HS) mutations as described in U.S. Pat. Nos. 7,312,378; 6,809,235; 6,403,863; 6,069,300; and 6,969,783, and International published application numbers WO 99/58698; WO 2003/0070901; WO 98/22601; and WO 02/072784, such as the HS33 mutation. In a specific embodiment, the polynucleotide encodes a mutant plant AGPase large subunit having the amino acid sequence shown in SEQ ID NO: 14 (Rev6+c424v), SEQ ID NO:15 (HS33+c424v); or SEQ ID NO:16 (Rev6+HS33+c424v).

In another embodiment, a composition of the invention or a polynucleotide of the invention encoding a mutant plant large AGPase subunit can also comprise a polynucleotide that encodes a mutant plant AGPase small subunit that can comprise an amino acid mutation as described in published International patent application WO 2005/019425 (Hannah and Linebarger). In one embodiment, the mutant AGPase small subunit encoded by the polynucleotide comprises an amino acid mutation wherein the tyrosine corresponding to amino acid position 36 of wild type small subunit maize endosperm AGPase is substituted with a cysteine. The mutant AGPase small subunit can also optionally comprise an amino acid inserted between the serine and threonine amino acids corresponding to amino acid positions 34 and 35 of wild type maize endosperm AGPase, respectively. In specific embodiments, the amino acid inserted between amino acids at position 34 and 35 of the AGPase small subunit is a glutamic acid or glutamine. In exemplified embodiments, the mutant plant AGPase small subunit comprises the amino acid sequence shown in SEQ ID NO:6, SEQ ID NO:7, or SEQ ID NO:8, or a fragment or variant thereof. In specific embodiments, the polynucleotide comprises the nucleotide sequences shown in SEQ ID NO:3, SEQ ID NO:4, or SEQ ID NO:5, or a fragment or variant thereof.

In another embodiment, a composition of the invention or a polynucleotide of the invention encoding a mutant large subunit AGPase can also comprise a polynucleotide that encodes a chimeric plant AGPase small subunit comprising sequences from two different plants (as described in U.S. Pat. No. 7,173,165) and/or a polynucleotide that encodes a plant AGPase small subunit that comprises an amino acid mutation wherein the threonine amino acid corresponding to amino acid position 462 of wild type maize endosperm AGPase small subunit is substituted with an amino acid that confers increased heat stability. In a specific embodiment of the latter, the amino acid substituted for threonine is an isoleucine. In one embodiment, the mutant plant AGPase small subunit comprises the amino acid sequence shown in SEQ ID NO:13, or a fragment or variant thereof. In a specific embodiment, the polynucleotide comprises the nucleotide sequence shown in SEQ ID NO:12, or a fragment or variant thereof.

A chimeric AGPase small subunit that can be used in the present invention can comprise a C-terminal portion from one plant and an N-terminal portion from another plant. In one embodiment, a chimeric AGPase small subunit of the present invention comprises an N-terminus sequence having approximately the first 150 to 250 amino acids of the N-terminus of a first plant AGPase small subunit and a C-terminus sequence comprising approximately the terminal 300 residues or less of the C-terminus of a second plant AGPase small subunit. Thus, the C-terminus of the chimeric small subunit can comprise the terminal 300, or 299, or 298, or 297, or 296, or 295, and so forth, residues of the C-terminus of the second plant. The small subunit sequences can be from an AGPase of a monocot or dicot plant, or both a monocot and a dicot. Monocotyledonous plants, such as, for example, rice, wheat, barley, oats, sorghum, maize, lilies, and millet are included within the scope of the invention. Dicot plants can include, for example, tobacco, soybean, potato, sweet potato, radish, cabbage, rape, apple tree, and lettuce. In one embodiment, the first 200 or so amino acids of the N-terminus of the chimeric AGPase small subunit are from the N-terminus of maize endosperm AGPase small subunit and the C-terminus amino acids are from the C-terminus of potato tuber AGPase small subunit plus the mutation corresponding to amino acid position 462 of the present invention. In a specific embodiment, the C-terminus region of a chimeric AGPase small subunit of the present invention comprises the terminal 276 amino acids of the AGPase small subunit of potato tuber. In an exemplified embodiment, the chimeric AGPase small subunit comprises a portion of the small subunit of maize endosperm AGPase and a portion of the small subunit of potato tuber AGPase. In a specific embodiment, the chimeric AGPase small subunit contains a) the first 199 amino acids (i.e., amino acids 1 through 199) from the small subunit of maize endosperm AGPase and the carboxyl terminal end of the small subunit of potato tuber AGPase, starting at amino acid 246 (i.e., amino acids 246 through 521) using the amino acid sequence shown for the protein deposited as Genbank accession number X61186 (or, alternatively, starting at amino acid 175 using the numbering system for the potato AGPase subunit as in Hannah et al., 2001) and b) the mutation wherein the threonine amino acid corresponding to amino acid position 462 of wild type maize endosperm AGPase small subunit is substituted with an amino acid that confers increased heat stability, such as an isoleucine. In an exemplified embodiment, the plant chimeric AGPase small subunit comprises the amino acid sequence shown in SEQ ID NO:10 or SEQ ID NO:11, or a fragment or variant thereof. In a specific embodiment, the polynucleotide comprises the nucleotide sequence shown in SEQ ID NO:9, or a fragment or variant thereof.

The subject invention concerns materials and methods for providing plants with increased resistance to heat conditions. Increased resistance of a plant to heat conditions provides for decreasing the yield losses that are generally observed at elevated temperatures. In one embodiment, a polynucleotide of the invention encodes a plant AGPase large subunit having an amino acid mutation wherein the serine amino acid corresponding to amino acid position 163 of wild type maize endosperm AGPase large subunit is substituted with an amino acid that results in increased heat stability of AGPase activity when provided in an AGPase enzyme. In a specific embodiment, the amino acid substituted for the serine is a phenylalanine. In an exemplified embodiment, the mutant plant AGPase large subunit comprises the amino acid sequence shown in SEQ ID NO:18, or a fragment or variant thereof that exhibits substantially the same activity as a full-length amino acid sequence. In a specific embodiment, the polynucleotide comprises the nucleotide sequence shown in SEQ IDNO: 17, or a fragment or variant thereof. In addition to comprising a mutation providing increased resistance to heat conditions, the mutant plant AGPase large subunit can also comprise a mutation of the invention providing for increased starch production. In one embodiment, the mutant plant AGPase large subunit comprises the amino acid sequence shown in SEQ ID NO:47, or a fragment or variant thereof that exhibits substantially the same activity as a full-length amino acid sequence. In a specific embodiment, the polynucleotide comprises the nucleotide sequence shown in SEQ ID NO:47, or a fragment or variant thereof.

The subject invention also comprises methods for increasing starch biosynthesis and/or resistance to heat conditions and increasing crop yield of a plant or plant tissue. In one embodiment, a method of the invention comprises introducing one or more polynucleotides of the present invention into a plant. In an exemplified embodiment, the mutant plant AGPase large subunit encoded by the polynucleotide comprises the amino acid sequence shown in SEQ ID NO:2, SEQ ID NO:18, or SEQ ID NO:47, or a fragment or variant thereof that exhibits substantially the same activity as a full-length amino acid sequence. In a specific embodiment, the polynucleotide comprises the nucleotide sequence shown in SEQ ID NO:1, SEQ ID NO:17, or SEQ ID NO:47, or a fragment or variant thereof. In one embodiment, the polynucleotide is stably incorporated into the genome of the plant or plant tissue. The polynucleotide can comprise regulatory elements, such as a promoter and/or enhancer sequences, that provide for increased expression of the polynucleotide and/or the polypeptide encoded thereby. In a specific embodiment, the promoter sequence is one that provides for constitutive or tissue-specific (e.g., endosperm) expression. Plants or plant tissues containing the polynucleotide, or progeny of the plants, optionally can be screened for increased expression of a polynucleotide or polypeptide of the invention. In one embodiment, multiple copies of one or more polynucleotides of the invention are introduced into a plant or plant tissue and stably incorporated into the genome of the plant. In one embodiment, a polynucleotide of the invention is provided in an expression construct as described herein.

The subject invention also comprises mutant large subunit AGPase polypeptides encoded by the polynucleotides of the invention. In one embodiment, the polypeptide comprises the amino acid sequence shown in SEQ ID NO:2, SEQ ID NO:18, or SEQ ID NO:47, or a fragment or variant thereof that exhibits substantially the same activity as a full-length amino acid sequence.

The subject invention also concerns mutant plant AGPase enzymes comprising one or more mutant polypeptides of the invention. In specific embodiments, a mutant plant AGPase enzyme comprises one or more mutant polypeptides any of which can comprise the amino acid sequence of SEQ ID NO:2, SEQ ID NO:6, SEQ ID NO:7, SEQ ID NO:8, SEQ ID NO:10, SEQ ID NO:11, SEQ ID NO:13, SEQ ID NO:14, SEQ ID NO:15, SEQ ID NO:16, SEQ ID NO:18, or SEQ ID NO:47, or a fragment or variant of any such sequence, wherein the mutant AGPase enzyme exhibits increased enzymatic activity relative to a wild type AGPase enzyme. In one embodiment, the mutant plant enzyme comprises two mutant AGPase large subunits of the invention, wherein the mutant polypeptides can have the same mutation(s) or can have different mutation(s). The subject invention also concerns mutant plant AGPase enzymes comprising one or more mutant large subunit polypeptides of the invention and one or more mutant small subunit polypeptides. In one embodiment, the mutant large subunit polypeptide can also comprise any of the mutations described in any of U.S. Pat. Nos. 5,589,618; 5,650,557; 5,872,216; 6,069,300; 6,184,438; 6,403,863; 6,809,235; 7,173,165; 7,312,378; and 6,969,783. In one embodiment, a mutant large subunit polypeptide of the invention comprises a Rev6 mutation. In another embodiment, a mutant large subunit AGPase polypeptide of the invention also comprises one or more heat stable (HS) mutations as described in U.S. Pat. Nos. 6,069,300; 6,403,863; 6,809,235; 7,312,378; and 6,969,783, and published International patent application nos. WO 99/58698; WO 2003/0070901; WO 98/22601; and WO 02/072784, such as, for example, the HS33 mutation. In one embodiment, the mutant plant AGPase enzyme comprises two mutant small subunit polypeptides, wherein the mutant small subunit polypeptides can have the same mutation(s) or can have different mutation(s), as described herein. In another embodiment, the mutant plant AGPase enzyme comprises two mutant large subunit AGPase polypeptides wherein the mutant polypeptides can have the same mutation(s) or can have different mutation(s), as described herein. In a further embodiment, the mutant plant AGPase enzyme comprises two mutant small subunit AGPase polypeptides and two mutant large subunit AGPase polypeptides, wherein the mutant small subunit polypeptides and the mutant large subunit polypeptides can have the same mutation(s) or can have different mutation(s), as described herein.

The subject invention also concerns methods for providing for a mutant plant AGPase enzyme having increased enzymatic activity relative to wild type plant AGPase. In one embodiment, the method comprises incorporating or providing one or more mutant AGPase large subunit polypeptides of the present invention with wild type or mutant AGPase small subunits in an AGPase enzyme. In one embodiment, the AGPase enzyme comprises a tetramer of polypeptide subunits, wherein one, two, or more of the subunits is a mutant large subunit polypeptide of the present invention. In one embodiment, the AGPase enzyme comprises a mutant large subunit of the invention which also comprises additional mutations, for example, as described in any of U.S. Pat. Nos. 5,589,618; 5,650,557; 5,872,216; 6,069,300; 6,184,438; 6,403,863; 6,809,235; 7,173,165; 7,312,378; and 6,969,783, such as the Rev6 mutation and/or a heat stability mutation, such as HS33. In one embodiment, the AGPase enzyme also comprises a further mutant large subunit polypeptide subunit, such as a large subunit comprising a Rev6 mutation (as described in U.S. Pat. Nos. 5,872,216; 5,650,557; and 5,589,618, and International published application number WO 98/10082) and/or a heat stability mutation (as described in U.S. Pat. Nos. 7,312,378; 6,809,235; 6,403,863; 6,069,300; and 6,969,783, and International published application numbers WO 99/58698; WO 2003/0070901; WO 98/22601; and WO 02/072784), such as HS33. In one embodiment, a mutant plant AGPase enzyme of the invention also comprises one or more mutant AGPase small subunits as described herein (see, for example, U.S. Pat. No. 7,173,165 and International published application number WO 2003/047527).

The subject invention also concerns plants, plant tissue, and plant cells that comprise a polynucleotide or the protein encoded by the polynucleotide of the invention, or that express a mutant polypeptide of the invention, or a fragment or variant thereof, or that comprise or express a mutant plant AGP enzyme of the present invention. In an exemplified embodiment, the mutant plant AGPase large subunit encoded by the polynucleotide comprises the amino acid sequence shown in SEQ ID NO:2, SEQ ID NO:18, or SEQ ID NO:47, or a fragment or variant thereof that exhibits substantially the same activity as a full-length amino acid sequence. In a specific embodiment, the polynucleotide comprises the nucleotide sequence shown in SEQ ID NO:1, SEQ ID NO:17, or SEQ ID NO:47, or a fragment or variant thereof. Plant tissue includes, but is not limited to, seed, scion, and rootstock. Plants within the scope of the present invention include monocotyledonous plants, such as, for example, rice, wheat, barley, oats, rye, sorghum, maize, sugarcane, pineapple, onion, bananas, coconut, lilies, turfgrasses, and millet. Plants within the scope of the present invention also include dicotyledonous plants, such as, for example, tomato, cucumber, squash, peas, alfalfa, melon, chickpea, chicory, clover, kale, lentil, soybean, beans, tobacco, potato, sweet potato, yams, cassava, radish, broccoli, spinach, cabbage, rape, apple trees, citrus (including oranges, mandarins, grapefruit, lemons, limes and the like), grape, cotton, sunflower, strawberry, and lettuce. Herb plants containing a polynucleotide of the invention are also contemplated within the scope of the invention. Herb plants include parsley, sage, rosemary, thyme, and the like. In one embodiment, the plant, plant tissue, or plant cell is *Zea mays*. In one embodiment, a plant, plant tissue, or plant cell of the invention is a transgenic plant, plant tissue, or plant cell. In another embodiment, a plant, plant tissue, or plant cell of the invention is one that has been obtained through a breeding program.

Polynucleotides useful in the present invention can be provided in an expression construct. Expression constructs of the invention generally include regulatory elements that are functional in the intended host cell in which the expression construct is to be expressed. Thus, a person of ordinary skill in the art can select regulatory elements for use in bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

An expression construct of the invention can comprise a promoter sequence operably linked to a polynucleotide sequence encoding a mutant polypeptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

If the expression construct is to be provided in or introduced into a plant cell, then plant viral promoters, such as, for example, a cauliflower mosaic virus (CaMV) 35S (including the enhanced CaMV 35S promoter (see, for example U.S. Pat. No. 5,106,739)) or a CaMV 19S promoter or a cassava vein mosaic can be used. Other promoters that can be used for expression constructs in plants include, for example, prolifera promoter, Ap3 promoter, heat shock promoters, T-DNA 1'- or 2'-promoter of A. tumefaciens, polygalacturonase promoter, chalcone synthase A (CHS-A) promoter from petunia, tobacco PR-la promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Tissue-specific promoters, for example fruit-specific promoters, such as the E8 promoter of tomato (accession number: AF515784; Good et al. (1994)) can be used. Fruit-specific promoters such as flower organ-specific promoters can be used with an expression construct of the present invention for expressing a polynucleotide of the invention in the flower organ of a plant. Examples of flower organ-specific promoters include any of the promoter sequences described in U.S. Pat. Nos. 6,462,185; 5,639,948; and 5,589,610. Seed-specific promoters such as the promoter from a β-phaseolin gene (for example, of kidney bean) or a glycinin gene (for example, of soybean), and others, can also be used. Endosperm-specific promoters include, but are not limited to, MEGI (EPO application No. EP1528104) and those described by Wu et al. (1998), Furtado et al. (2001), and Hwang et al. (2002). Root-specific promoters, such as any of the promoter sequences described in U.S. Pat. No. 6,455,760 or U.S. Pat. No. 6,696, 623, or in published U.S. patent application Nos. 20040078841; 20040067506; 20040019934; 20030177536; 20030084486; or 20040123349, can be used with an expression construct of the invention. Constitutive promoters (such as the CaMV, ubiquitin, actin, or NOS promoter), developmentally-regulated promoters, and inducible promoters (such as those promoters than can be induced by heat, light, hormones, or chemicals) are also contemplated for use with polynucleotide expression constructs of the invention.

Expression constructs of the invention may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the invention. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements must be present within the transcribed region and are orientation dependent. Examples include the maize shrunken-1 enhancer element (Clancy and Hannah, 2002).

DNA sequences which direct polyadenylation of mRNA transcribed from the expression construct can also be included in the expression construct, and include, but are not limited to, an octopine synthase or nopaline synthase signal. The expression constructs of the invention can also include a polynucleotide sequence that directs transposition of other genes, i.e., a transposon.

Polynucleotides of the present invention can be composed of either RNA or DNA. Preferably, the polynucleotides are composed of DNA. The subject invention also encompasses those polynucleotides that are complementary in sequence to the polynucleotides disclosed herein. Polynucleotides and polypeptides of the invention can be provided in purified or isolated form.

Because of the degeneracy of the genetic code, a variety of different polynucleotide sequences can encode mutant polypeptides of the present invention. A table showing all possible triplet codons (and where U also stands for T) and the amino acid encoded by each codon is described in Lewin (1985). In addition, it is well within the skill of a person trained in the art to create alternative polynucleotide sequences encoding the same, or essentially the same, mutant polypeptides of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by the polynucleotides of the present invention. Allelic variants of the nucleotide sequences encoding a large subunit AGPase of the invention are also encompassed within the scope of the invention.

Substitution of amino acids other than those specifically exemplified or naturally present in a mutant polypeptide of the invention are also contemplated within the scope of the present invention. For example, non-natural amino acids can be substituted for the amino acids of a mutant large subunit AGPase polypeptide, so long as the mutant polypeptide having the substituted amino acids retains substantially the same functional activity as the mutant polypeptide in which amino acids have not been substituted. Examples of non-natural amino acids include, but are not limited to, omithine, citrulline, hydroxyproline, homoserine, phenylglycine, taurine, iodotyrosine, 2,4-diaminobutyric acid, a-amino isobutyric acid, 4-aminobutyric acid, 2-amino butyric acid, γ-amino butyric acid, e-amino hexanoic acid, 6-amino hexanoic acid, 2-amino isobutyric acid, 3-amino propionic acid, norleucine, norvaline, sarcosine, homocitrulline, cysteic acid, t-butylglycine, t-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form. Allelic variants of a protein sequence of a mutant large subunit and/or small subunit AGPase polypeptide of the present invention are also encompassed within the scope of the invention.

Amino acids can be generally categorized in the following classes: non-polar, uncharged polar, basic, and acidic. Conservative substitutions whereby a mutant polypeptide enzyme of the present invention having an amino acid of one class is replaced with another amino acid of the same class fall within the scope of the subject invention so long as the mutant polypeptide having the substitution still retains substantially the same functional activity (e.g., increased enzymatic and/or increased heat stability of an AGPase enzyme) as the mutant polypeptide that does not have the substitution. Polynucleotides encoding a mutant polypeptide having one or more amino acid substitutions in the sequence are contemplated within the scope of the present invention. Table 1 below provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

The subject invention also concerns variants of the polynucleotides of the present invention that encode functional mutant large or small subunit AGPase polypeptides of the invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Fragments and variants of a mutant polypeptide of the present invention can be generated as described herein and tested for the presence of enzymatic and heat stable function using standard techniques known in the art. Thus, an ordinarily skilled artisan can readily prepare and test fragments and variants of a mutant polypeptide of the invention and determine whether the fragment or variant retains functional activity relative to full-length or a non-variant mutant polypeptide.

Polynucleotides and polypeptides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983):

$Tm=81.5\ C+16.6\ Log[Na+]+0.41\ (\%\ G+C)-0.61\ (\%\ formamide)-600/length\ of\ duplex\ in\ base\ pairs.$ Washes are typically carried out as follows:
(1) Twice at room temperature for 15 minutes in 1×SSPE, 0.1% SDS (low stringency wash).
(2) Once at Tm-20 C for 15 minutes in 0.2×SSPE, 0.1% SDS (moderate stringency wash).

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. Allelic variations of the exemplified sequences also fall within the scope of the subject invention. The polynucleotide sequence includes both the sense and antisense strands either as individual strands or in the duplex.

Techniques for transforming plant cells with a gene are known in the art and include, for example, *Agrobacterium* infection, biolistic methods, electroporation, calcium chloride treatment, PEG-mediated transformation, etc. U.S. Pat. No. 5,661,017 teaches methods and materials for transforming an algal cell with a heterologous polynucleotide. Transformed cells can be selected, redifferentiated, and grown into plants that contain and express a polynucleotide of the invention using standard methods known in the art. The seeds and other plant tissue and progeny of any transformed or transgenic plant cells or plants of the invention are also included within the scope of the present invention.

The subject invention also concerns methods for producing a plant that exhibits increased starch production and/or increased resistance to heat conditions relative to a wild type plant, wherein a polynucleotide encoding a mutant large subunit AGPase polypeptide of the present invention is introduced into a plant cell and the polypeptide(s) encoded by the polynucleotide(s) is expressed. In an exemplified embodiment, the mutant plant AGPase large subunit encoded by the polynucleotide comprises the amino acid sequence shown in SEQ ID NO:2, SEQ ID NO:18, or SEQ ID NO:47, or a fragment or variant thereof that exhibits substantially the same activity as a full-length amino acid sequence. In a specific embodiment, the polynucleotide comprises the nucleotide sequence shown in SEQ ID NO:1, SEQ ID NO:17, or SEQ ID NO:47, or a fragment or variant thereof. In one embodiment, the plant cell comprises non-mutant genes encoding wild type small subunit AGPase polypeptide. In another embodiment, the plant cell comprises at least one polynucleotide encoding a mutant small subunit AGPase polypeptide, such as one of the mutant small subunits described herein. In a further embodiment, a polynucleotide encoding a mutant small subunit AGPase polypeptide is also introduced into a plant cell along with the polynucleotide encoding a mutant large subunit polypeptide. In one embodiment, the polynucleotide or polynucleotides is incorporated into the genome of the plant cell and a plant is grown from the plant cell. In a preferred embodiment, the plant grown from the plant cell stably expresses the incorporated polynucleotide or polynucleotides.

The subject invention also concerns oligonucleotide probes and primers, such as polymerase chain reaction (PCR) primers, that can hybridize to a coding or non-coding sequence of a polynucleotide of the present invention. Oligonucleotide probes of the invention can be used in methods for detecting and quantitating nucleic acid sequences encoding a mutant large subunit polypeptide of the invention. Oligonucleotide primers of the invention can be used in PCR methods and other methods involving nucleic acid amplification. In a preferred embodiment, a probe or primer of the invention can hybridize to a polynucleotide of the invention under stringent conditions. Probes and primers of the invention can optionally comprise a detectable label or reporter molecule, such as fluorescent molecules, enzymes, radioactive moiety (e.g., $^3$H, $^{35}$S, $^{125}$I, etc.), and the like. Probes and primers of the invention can be of any suitable length for the method or assay in which they are being employed. Typically, probes and primers of the invention will be 10 to 500 or more nucleotides in length. Probes and primers that are 10 to 20, 21 to 30, 31 to 40, 41 to 50, 51 to 60, 61 to 70, 71 to 80, 81 to 90, 91 to 100 or more nucleotides in length are contemplated within the scope of the invention. Probes and primers of the invention can have complete (100%) nucleotide sequence identity with the polynucleotide sequence, or the sequence identity can be less than 100%. For example, sequence identity between a probe or primer and a sequence can be 99%, 98%, 97%, 96%, 95%, 90%, 85%, 80%, 75%, 70% or any other percentage sequence identity so long as the probe or primer can hybridize under stringent conditions to a nucleotide sequence of a polynucleotide of the invention. In one embodiment, a probe or primer of the invention has 70% or greater, 75% or greater, 80% or greater, 85% or greater, 90% or greater, or 95% to 100% sequence identity with a nucleotide sequence of SEQ ID NO:1, SEQ ID NO:17, or SEQ ID NO:47, or the complement thereof.

The subject invention also concerns isolated mutant large subunit AGPase polypeptides. In one embodiment, the mutant polypeptide is a polypeptide of *Zea mays*. In a specific embodiment, a large subunit AGPase polypeptide of the invention has an amino acid sequence as shown in SEQ ID NO:2, SEQ ID NO:18, or SEQ ID NO:47, or functional fragment or variant thereof that exhibits substantially the same activity as a full-length amino acid sequence. A mutant large subunit polypeptide of the invention can be purified using standard techniques known in the art. In one embodiment, a polynucleotide of the invention encoding a mutant large subunit polypeptide is incorporated into a microorganism, such as *E. coli*, and the mutant large subunit polypeptide expressed in the microorganism and then isolated therefrom. The subject invention also concerns a mutant plant AGPase enzyme comprising one or more mutant plant AGPase subunits of the invention. In one embodiment, the mutant enzyme comprises one or more polypeptides having an amino acid sequence shown in SEQ ID NOs:2, 6, 7, 8, 10, 11, 13, 14, 15, 16, 18, or 47.

Polypeptides of the invention, and functional peptide fragments thereof, can be used to generate antibodies that bind specifically to a polypeptide of the invention, and such antibodies are contemplated within the scope of the invention. The antibodies of the invention can be polyclonal or monoclonal and can be produced and isolated using standard methods known in the art.

Polypeptide fragments according to the subject invention typically comprise a contiguous span of about or at least 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, or 515 amino acids of SEQ ID NO:2 or SEQ ID NO:18.

Polypeptide fragments of the subject invention can be any integer in length from at least about 25 consecutive amino acids to 1 amino acid less than the sequence shown in SEQ ID NO:2, SEQ ID NO:18, or SEQ ID NO:47. Thus, for SEQ ID NO:2, SEQ ID NO:18, or SEQ ID NO:47, a polypeptide fragment can be any integer of consecutive amino acids from about 25 to 475 amino acids. The term "integer" is used herein in its mathematical sense and thus representative integers include: 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, and/or 515.

Each polypeptide fragment of the subject invention can also be described in terms of its N-terminal and C-terminal positions. For example, combinations of N-terminal to C-terminal fragments of about 25 contiguous amino acids to 1 amino acid less than the full length polypeptide of SEQ ID NO:2, SEQ ID NO:18, or SEQ ID NO:47 are included in the present invention. Thus, using SEQ ID NO:2, SEQ ID NO:18, or SEQ ID NO:47 as an example, a 25 consecutive amino acid fragment could correspond to amino acids of SEQ ID NO:2, SEQ ID NO:18, or SEQ ID NO:47, selected from the group consisting of 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, 26-50, 27-51, 28-52, 29-53, 30-54, 31-55, 32-56, 33-57, 34-58, 35-59, 36-60, 37-61, 38-62, 39-63, 40-64, 41-65, 42-66, 43-67, 44-68, 45-69, 46-70, 47-71, 48-72, 49-73, 50-74, 51-75, 52-76, 53-77, 54-78, 55-79, 56-80, 57-81, 58-82, 59-83, 60-84, 61-85, 62-86, 63-87, 64-88, 65-89, 66-90, 67-91, 68-92, 69-93, 70-94, 71-95, 72-96, 73-97, 74-98, 75-99, 76-100, 77-101, 78-102, 79-103, 80-104, 81-105, 82-106, 83-107, 84-108, 85-109, 86-110, 87-111, 88-112, 89-113, 90-114, 91-115, 92-116, 93-117, 94-118, 95-119, 96-120, 97-121, 98-122, 99-123, 100-124, 101-125, 102-126, 103-127, 104-128, 105-129, 106-130, 107-131, 108-132, 109-133, 110-134, 111-135, 112-136, 113-137, 114-138, 115-139, 116-140, 117-141, 118-142, 119-143, 120-144, 121-145, 122-146, 123-147, 124-148, 125-149, 126-150, 127-151, 128-152, 129-153, 130-154, 131-155, 132-156, 133-157, 134-158, 135-159, 136-160, 137-161, 138-162, 139-163, 140-164, 141-165, 142-166, 143-167, 144-168, 145-169, 146-170, 147-171, 148-172, 149-173, 150-174, 151-175, 152-176, 153-177, 154-178, 155-179, 156-180, 157-181, 158-182, 159-183, 160-184, 161-185, 162-186, 163-187, 164-188, 165-189, 166-190, 167-191, 168-192, 169-193, 170-194, 171-195, 172-196, 173-197, 174-198, 175-199, 176-200, 177-201, 178-202, 179-203, 180-204, 181-205, 182-206, 183-207, 184-208, 185-209, 186-210, 187-211, 188-212, 189-213, 190-214, 191-215, 192-216, 193-217, 194-218, 195-219, 196-220, 197-221, 198-222, 199-223, 200-224, 201-225, 202-226, 203-227, 204-228, 205-229, 206-230, 207-231, 208-232, 209-233, 210-234, 211-235, 212-236, 213-237, 214-238, 215-239, 216-240, 217-241, 218-242, 219-243, 220-244, 221-245, 222-246, 223-247, 224-248, 225-249, 226-250, 227-251, 228-252, 229-253, 230-254, 231-255, 232-256, 233-257, 234-258, 235-259, 236-260, 237-261, 238-262, 239-263, 240-264, 241-265, 242-266, 243-267, 244-268, 245-269, 246-270, 247-271, 248-272, 249-273, 250-274, 251-275, 252-276, 253-277, 254-278, 255-279, 256-280, 257-281, 258-282, 259-283, 260-284, 261-285, 262-286, 263-287, 264-288, 265-289, 266-290, 267-291, 268-292, 269-293, 270-294, 271-295, 272-296, 273-297, 274-298, 275-299, 276-300, 277-301, 278-302, 279-303, 280-304, 281-305, 282-306, 283-307, 284-308, 285-309, 286-310, 287-311, 288-312, 289-313, 290-314, 291-315, 292-316, 293-317, 294-318, 295-319, 296-320, 297-321, 298-322, 299-323, 300-324, 301-325, 302-326, 303-327, 304-328, 305-329, 306-330, 307-331, 308-332, 309-333, 310-334, 311-335, 312-336, 313-337, 314-338, 315-339, 316-340, 317-341, 318-342, 319-343, 320-344, 321-345, 322-346, 323-347, 324-348, 325-349, 326-350, 327-351, 328-352, 329-353, 330-354, 331-355, 332-356, 333-357, 334-358, 335-359, 336-360, 337-361, 338-362, 339-363, 340-364, 341-365, 342-366, 343-367, 344-368, 345-369, 346-370, 347-371, 348-372, 349-373, 350-374, 351-375, 352-376, 353-377, 354-378, 355-379, 356-380, 357-381, 358-382, 359-383, 360-384, 361-385, 362-386, 363-387, 364-388, 365-389, 366-390, 367-391, 368-392, 369-393, 370-394, 371-395, 372-396, 373-397, 374-398, 375-399, 376-400, 377-401, 378-402, 379-403, 380-404, 381-405, 382-406, 383-407, 384-408, 385-409, 386-410, 387-411, 388-412, 389-413, 390-414, 391-415, 392-416, 393-417, 394-418, 395-419, 396-420, 397-421, 398-422, 399-423, 400-424, 401-425, 402-426, 403-427, 404-428, 405-429, 406-430, 407-431, 408-432, 409-433, 410-434, 411-435, 412-436, 413-437, 414-438, 415-439, 416-440, 417-441, 418-442, 419-443, 420-444, 421-445, 422-446, 423-447, 424-448, 425-449, 426-450, 427-451, 428-452, 429-453, 430-454, 431-455, 432-456, 433-457, 434-458, 435-459, 436-460, 437-461, 438-462, 439-463, 440-464, 441-465, 442-466, 443-467, 444-468, 445-469, 446-470, 447-471, 448-472, 449-473, 450-474, 451-475, 452-476, 453-477, 454-478, 455-479, 456-480, 457-481, 458-482, 459-483, 460-484, 461-485, 462-486, 463-487, 464-488, 465-489, 466-490, 467-491, 468-492, 469-493, 470-494, 471-495, 472-496, 473-497, 474-498, 475-499, 476-500, 477-501, 478-502, 479-503, 480-504, 481-505, 482-506, 483-507, 484-508, 485-509, 486-510, 487-511, 488-512, 489-513, 490-514, and/or 491-515. Similarly, the amino acids corresponding to all other fragments of sizes between 26 consecutive amino acids and 474 (or 475) consecutive amino acids of SEQ ID NO:2, SEQ ID NO:18, or SEQ ID NO:47, are included in the present invention and can also be immediately envisaged based on these examples. Therefore, additional examples, illustrating various fragments of the polypeptides of SEQ ID NO:2, SEQ ID NO:18, or SEQ ID NO:47, are not individually listed herein in order to avoid unnecessarily lengthening the specification.

Polypeptide fragments comprising: 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515 consecutive amino acids of SEQ ID NO:2, SEQ ID NO:18, or SEQ ID NO:47 may alternatively be described by the formula "n to c" (inclusive), where "n" equals the N-terminal amino acid position and "c" equals the C-terminal amino acid position of the polypeptide. In this embodiment of the invention, "n" is an integer having a lower limit of 1 and an upper limit of the total number of amino acids of the full length polypeptide minus 24 (e.g., 516−24=492 for SEQ ID NO:2). "c" is an integer between 25 and the number of amino acids of the full length polypeptide sequence (516 for SEQ ID NO:2) and "n" is an integer smaller than "c" by at least 24. Therefore, for SEQ ID NO:2, SEQ ID NO:18, or SEQ ID NO:47, "n" is any integer selected from the list consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491; and "c" is any integer selected from the group consisting of: 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, and 515 provided that "n" is a value less than "c" by at least 24. Every combination of "n" and "c" positions are included as specific embodiments of polypeptide fragments of the invention. All ranges used to describe any polypeptide fragment embodiment of the present invention are inclusive unless specifically set forth otherwise.

Fragments of a mutant large or small subunit AGPase polypeptide of the invention, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Polypeptide fragments can also be prepared by chemical synthesis or using host cells transformed with an expression vector comprising a polynucleotide encoding a fragment of a mutant large or small subunit AGPase polypeptide of the invention, for example, a mutant polypeptide that is a fragment of the amino acid sequence shown in SEQ ID NO:2, SEQ ID NO:18, or SEQ ID NO:47. Fragments of a mutant large or small subunit AGPase polypeptide of the invention also contemplated herein include fragments of the polypeptides wherein all or a part of a transit or signal sequence of the polypeptide is removed. In a specific embodiment, the present invention includes those polypeptides of SEQ ID NO:2, SEQ ID NO:14, SEQ ID NO:15, SEQ ID NO:16, SEQ ID NO:18, or SEQ ID NO:47 wherein amino acids 1 to 45 of the amino terminus are deleted.

The subject invention also concerns cells transformed with a polynucleotide of the present invention encoding a mutant large subunit AGPase polypeptide of the invention. In one embodiment, the cell is transformed with a polynucleotide sequence comprising a sequence encoding the amino acid sequence shown in SEQ ID NO:2, SEQ ID NO:18, or SEQ ID NO:47, and/or optionally a polynucleotide comprising a sequence encoding the amino acid sequence shown in SEQ ID NO:2, SEQ ID NO:6, SEQ ID NO:7, SEQ ID NO:8, SEQ ID NO:10, SEQ ID NO:11, SEQ ID NO:13, SEQ ID NO:14, SEQ ID NO:15, SEQ ID NO:16, SEQ ID NO:18, or SEQ ID NO:47, or a functional fragment or variant thereof. In a specific embodiment, the cell is transformed with a polynucleotide sequence shown in SEQ ID NO:1, SEQ ID NO:17, and/or SEQ ID NO:47, or a sequence encoding a functional fragment or variant of SEQ ID NO:2, SEQ ID NO:18, and/or SEQ ID NO:47. In one embodiment, a cell is also transformed with a polynucleotide encoding a mutant small subunit AGPase polypeptide as described herein, such as SEQ ID NO:3, 4, 5, 9, or 12. In one embodiment, the polynucleotide sequence is provided in an expression construct of the invention. The transformed cell can be a prokaryotic cell, for example, a bacterial cell such as E. coli or B. subtilis, or the transformed cell can be a eukaryotic cell, for example, a plant cell, including protoplasts, or an animal cell. Plant cells include, but are not limited to, dicotyledonous, monocotyledonous, and conifer cells. In one embodiment, the plant cell is a cell from a Zea mays plant. Animal cells include human cells, mammalian cells, avian cells, and insect cells. Mammalian cells include, but are not limited to, COS, 3T3, and CHO cells.

The subject invention also concerns methods for increasing starch synthesis in a plant or plant tissue (such as a plant seed or endosperm tissue). In one embodiment, a method of the invention comprises introducing one or more polynucleotides of the present invention into a plant. In one embodiment, the polynucleotide is stably incorporated into the genome of the plant or plant tissue. The polynucleotide can comprise regulatory elements, such as a promoter and/or enhancer sequences, that provide for increased expression of the polynucleotide and/or the polypeptide encoded thereby. In a specific embodiment, the promoter sequence is one that provides for constitutive or tissue-specific (e.g., endosperm) expression. Plants or plant tissues containing the polynucleotide, or progeny of the plants, optionally can be screened for increased expression of a polynucleotide or polypeptide of the invention. In one embodiment, multiple copies of one or more polynucleotides of the invention are introduced into a plant or plant tissue and stably incorporated into the genome of the plant. In one embodiment, a polynucleotide of the invention is provided in an expression construct as described herein.

The subject invention also concerns a method for preparing a plant having an AGPase enzyme that exhibits increased enzymatic activity relative to a wild type AGPase enzyme, said method comprising introducing a polynucleotide into a plant cell and growing a plant from said plant cell, wherein said polynucleotide encodes a mutant plant AGPase large subunit protein, or a functional fragment of said protein, said protein comprising an amino acid mutation wherein the amino acid corresponding to the cysteine amino acid at position 424 of wild type maize endosperm AGPase large subunit protein is replaced by an amino acid that confers increased enzymatic activity when said mutant AGPase large subunit is expressed to form an AGPase enzyme.

Single letter amino acid abbreviations are defined in Table 2.

TABLE 2

| Letter Symbol | Amino Acid |
|---|---|
| A | Alanine |
| B | Asparagine or aspartic acid |
| C | Cysteine |
| D | Aspartic Acid |
| E | Glutamic Acid |
| F | Phenylalanine |
| G | Glycine |
| H | Histidine |
| I | Isoleucine |
| K | Lysine |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |
| Z | Glutamine or glutamic acid |

Materials and Methods

Protein alignment and amino acid numbering. SH2 (Accession #: P55241), and potato tuber large subunit (Accession #: CAA43490) protein sequence alignment were obtained using the MEGA software (Kumar et al, 2004) with BLOSUM matrix followed by manual inspection. The large subunit amino acid numbers used throughout the report correspond to SH2.

Structure modeling. BT2, SH2, and the potato tuber large subunit monomer structures were modeled after the potato small subunit in the recently published 3D structure of the potato tuber homotetrameric AGPase (RCSB Protein Data Bank #: 1YP2c). SWISS MODEL was used for performing homology modeling (Schwede et al., 2003; Arnold et al., 2006). The potato tuber large subunit and SH2 were modeled from amino acid #34 and #94 to the end respectively due to poor alignment of the N' termini. WHATCHECK (Vriend, 1990) and VERIFY3D (Luthy et al., 1992) were used to structurally evaluate the models. The corresponding WHATCHECK values (z-values for Ramachandran plot, backbone conformation, chi-1/chi-2 angle correlation, bond lengths, and bond angles) were within acceptable range. The high quality of the models was verified by the positive values assigned by VERIFY3D throughout all the structures. Visualization and superimposition of models and structures was done with Chimera (Pettersen et al., 2004).

Site-directed mutagenesis. The PCR reactions for site-directed mutagenesis were done with high fidelity Vent polymerase (New England Biolabs) by using pMONcSh2 as a template. The following pairs of primers were used for generating C114A, H149S, S163F, M172T, Q213H, V227R, T361C, D368S, P372A, C382F, C424V, E438Q, V502T and A508S respectively:

```
                                            (SEQ ID NO: 19)
(5'-cctgttggaggagcatacaggcttattg-3', (SEQ ID NO: 20)
5'-caataagcctgtatgctcctccaacagg-3',)

(SEQ ID NO: 21)
(5'-cttaaccgccatatttctcgtacataccttg-3', (SEQ ID NO: 22)
5'-caaggtatgtacgagaaatatggcggttaag-3',)

(SEQ ID NO: 23)
(5'-caactttgctgatggatttgtacaggtattagc-3', (SEQ ID NO: 24)
5'-gctaatacctgtacaaatccatcagcaaagttg-3',)

(SEQ ID NO: 25)
(5'-gcggctacacaaacgcctgaagagccag-3', (SEQ ID NO: 26)
5'-ctggctcttcaggcgtttgtgtagccgc-3',)

(SEQ ID NO: 27)
(5'-cttgagtggcgatcatctttatcggatg-3', (SEQ ID NO: 28)
5'-catccgataaagatgatcgccactcaag-3',)

(SEQ ID NO: 29)
(5'-cttgtgcagaaacatcgagaggacgatgctg-3', (SEQ ID NO: 30)
5'-cagcatcgtcctctcgatgtttctgcacaag-3',)

(SEQ ID NO: 31)
(5'-gcaaacttggccctctgtgagcagccttcc-3', (SEQ ID NO: 32)
5'-ggaaggctgctcacagagggccaagtttgc-3',)

(SEQ ID NO: 33)
(5'-gcagccttccaagttttcattttacgatccaaaaacacc-3', (SEQ ID NO: 34)
5'-ggtgtttttggatcgtaaaatgaaaacttggaaggctgc-3',)

(SEQ ID NO: 35)
(5'-gtttgatttttacgatgcgaaaacacctttcttc-3'

(SEQ ID NO: 36)
5'-gaagaaaggtgttttcgcatcgtaaaaatcaaa-3')

(SEQ ID NO: 37)
(5'-cttcactgcaccccgattcttgcctccgacgc-3', (SEQ ID NO: 38)
5'-gcgtcggaggcaagaatcggggtgcagtgaag-3',)

(SEQ ID NO: 39)
(5'-cgtgtcagctctggagttgaactcaaggactc-3', (SEQ ID NO: 40)
5'-gagtccttgagttcaactccagagctgacacg-3',)

(SEQ ID NO: 41)
(5'-gcggacatctatcaaactgaagaagaag-3', (SEQ ID NO: 42)
5'-cttcttcttcagtttgatagatgtccgc-3')

(SEQ ID NO: 43)
(5'-ggtctggaatcacggtgatcctgaag-3', (SEQ ID NO: 44)
5'-cttcaggatcaccgtgattccagacc-3',)

(SEQ ID NO: 45)
(5'-gatcctgaagaattcaaccatcaacgatg-3', (SEQ ID NO: 46)
5'-catcgttgatggttgaattcttcaggatc-3')
```

Glycogen quantitation. Glycogen quantitation was performed by phenol reaction (Hanson and Phillips, 1981) as described by Georgelis and Hannah (2008).

Enzyme expression and purification. The SH2 wild type and variants were expressed along with wild type BT2 in bacterial cells AC70R1-504 cells (Iglesias et al., 1993) and the resulting enzymes were purified as described by Georgelis and Hannah (2008).

Enzyme kinetics. The forward direction of the reaction was used (G-1-P+ATP→ADP-glucose+PPi) for estimating $K_{cat}$, $K_m$ for ATP and G-1-P, and affinities for 3-PGA (Ka) and Pi (Ki). More specifically, 0.04-0.12 µg of purified enzyme was assayed, at 37° C. for 10 minutes, in the presence of 50 mM HEPES pH 7.4, 15 mM $MgCl_2$, 2.5 mM ATP, and 2.0 mM G-1-P and varying amounts of 3-PGA to determine Ka. Ki was determined in the presence of 15 mM 3-PGA. Kms for G-1-P and ATP were estimating by varying the amount of G-1-P and ATP respectively in the presence of 15 mM 3-PGA. The reaction was terminated by boiling for 2 minutes and PPi was coupled to a reduction in NADH concentration using a coupling reagent as described by Georgelis and Hannah (2008). The kinetic constants were calculated by using Prism 4.0 (Graph Pad, San Diego, Calif.). The Hill coefficients were calculated as described by Cross et al. (2004). The specific activity was linear with time and amount of AGPase for all AGPase variants under all conditions.

Heat stability. Heat stability of the SH2 wild type and variants expressed with wild type BT2 was determined as described by Georgelis and Hannah (2008). However, the enzyme was heated at 39° C., instead of 42 or 53° C., due to the high heat lability of the variants.

Western detection of SH2 and BT2. A Western blot detection of both BT2 and SH2 in BT2/SH2, BT2/V502T and BT2/A508S variants was performed as described by Georgelis and Hannah (2008). The only modification was that a polyclonal antibody against SH2 (1:2000 (v/v)) was used in addition to a polyclonal antibody against BT2 to detect both SH2 and BT2.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Figure 1:
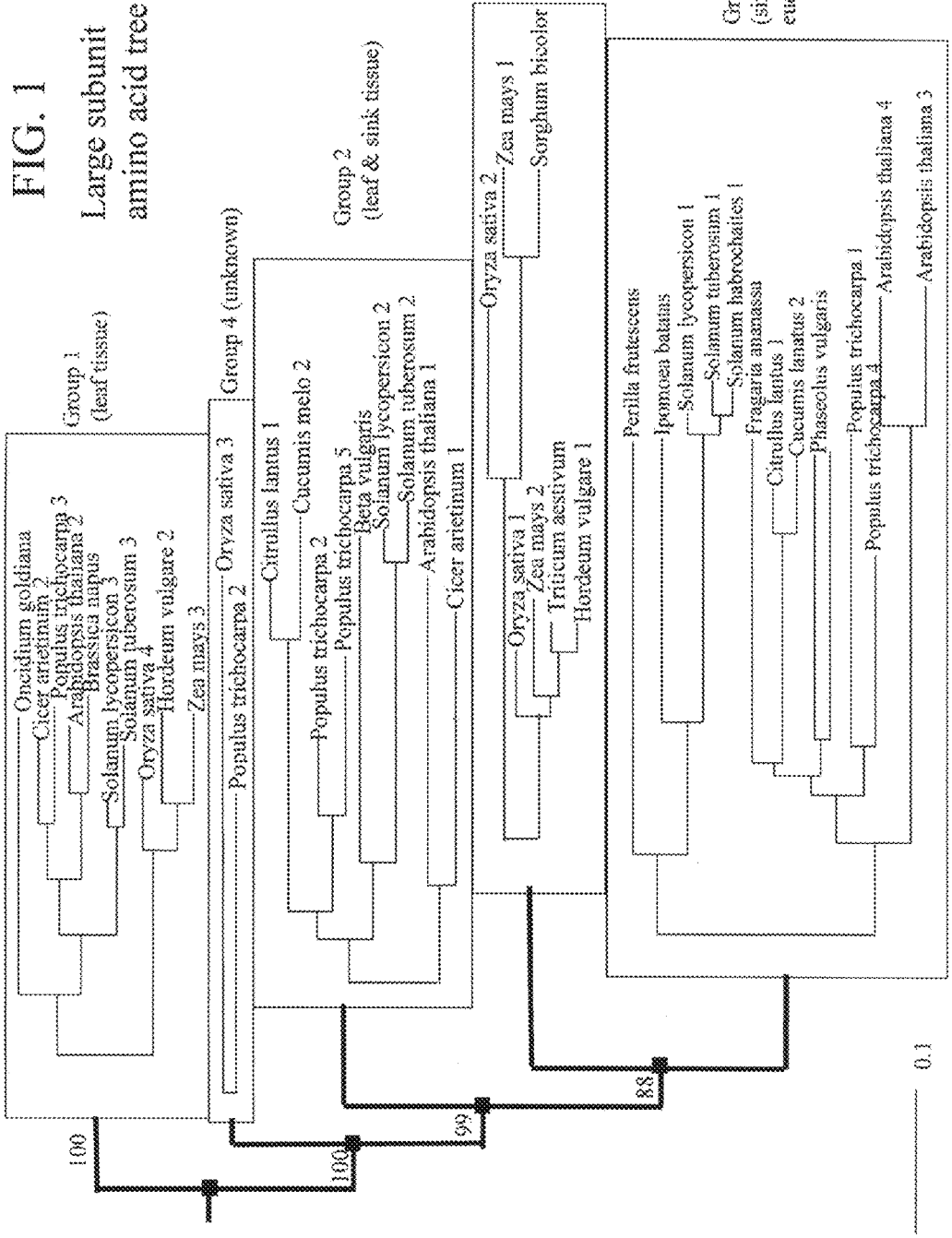
FIG. 1 shows an amino acid tree of AGPase large subunits in angiosperms. The tree was constructed by Georgelis et al. (2008). Boxes indicate duplication events. Positively selected amino acid sites detected in thick branches (Georgelis et al., 2008) were utilized as candidate sites for functional divergence. Bootstrap values >50% of the branches leading to the large subunit groups are shown.
Figure 2:
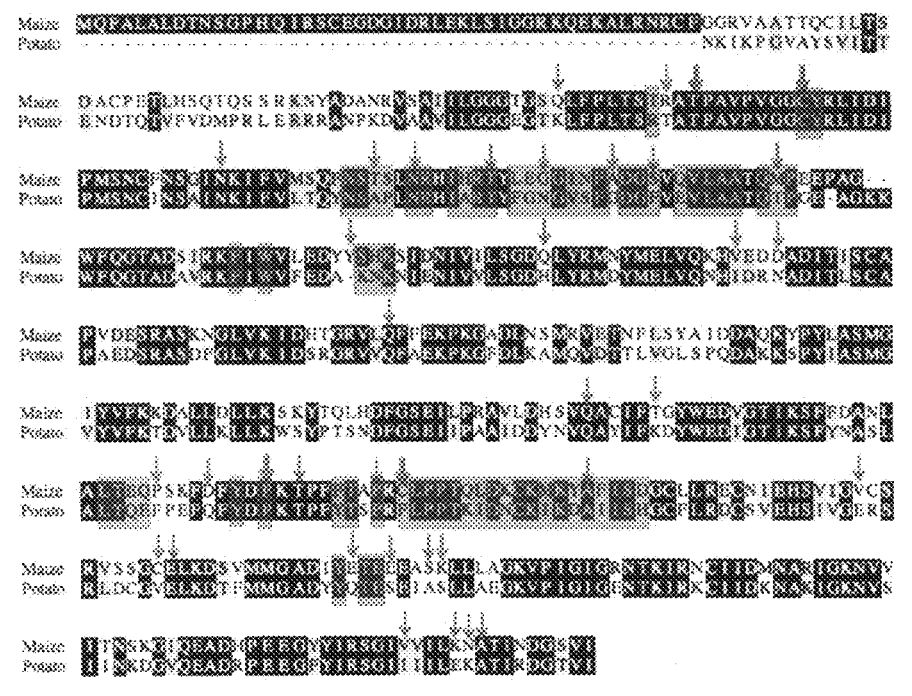

Previous Phylogenetic Analysis and Structural Mapping of Type-II and Positively Selected Sites The large subunit of AGPase can be classified into five groups depending on sequence similarity and tissue of expression (FIG. 1) (Georgelis et al., 2007; 2008). Group 4 includes only two sequences whose role has not been studied. Accordingly, we had restricted further evolutionary analysis to only the remaining four groups. We had identified 21 type-II sites (Table 3, FIG. 2) by doing an analysis of all the pairwise comparisons between the different large subunit groups shown in FIG. 1 (Georgelis et al., 2008). These amino acid sites have the potential to contribute to the functional divergence among AGPase large subunits. Type-II sites 96 and 106 have been shown to play an important role in enzyme catalysis (Ballicora et al., 2005), while site 506 has been implicated in the allosteric properties of AGPase by work conducted with potato tuber AGPase (Ballicora et al., 1998). We also had detected 18 amino acid sites upon which potential positive selection may have taken place in the tree branches following the gene duplications that led to the creation of the different large subunit groups (Table 3, FIG. 2) (Georgelis et al., 2008). These sites could also be important in large subunit specialization since functional diversification among different large subunits could have been beneficial for the fitness of the plant. Positively selected sites 104, 230, 441 and 445 are implicated in the allosteric properties of AGPase (Kavakli et al., 2001a; Ballicora et al., 2005; Jin et al., 2005). Finally, we had identified 91 type-I sites. These sites are apparently important for AGPase function in one group but not in another group and they could contribute towards subfunctionalization or specialization or both among large subunit groups. However, the usefulness of type-I sites in detecting functional divergence has been disputed (Philippe et al., 2003). More specifically, it has been argued that type-I divergence between orthologous and paralogous groups is indistinguishable in some instances (Gribaldo et al., 2003). It would be expected that paralogous sequences have functionally diverged more than orthologous sequences. Hence, a much higher type-I divergence in paralogous than in orthologous sequences would be expected. Therefore, there maybe a considerable number of false-positive sites of type-I divergence that do not necessarily represent functional divergence.

TABLE 3

Type-II and positively selected sites in the large subunit of AGPase (Georgelis et al., 2008). Highlights indicate sites that are already known to have a role in kinetic or allosteric properties of AGPase.

| Type II sites | Positively selected sites |
| --- | --- |
| 96 | 104 |
| 106 | 106 |
| 114 | 114 |
| 151 | 131 |
| 163 | 142 |
| 172 | 155 |
| 213 | 160 |
| 336 | 198 |
| 372 | 227 |
| 374 | 230 |
| 380 | 261 |
| 382 | 341 |
| 396 | 364 |

TABLE 3-continued

Type-II and positively selected sites in the large subunit of AGPase (Georgelis et al., 2008). Highlights indicate sites that are already known to have a role in kinetic or allosteric properties of AGPase.

| Type II sites | Positively selected sites |
| --- | --- |
| 416 | 368 |
| 425 | 382 |
| 438 | 424 |
| 444 | 441 |
| 502 | 445 |
| 506 | |
| 507 | |
| 508 | |

The fact that several type-II and positively selected sites have already been shown to be important for the kinetic and allosteric properties of AGPase strongly suggests that the remaining type-II and positively selected sites may also be important for enzyme function. To gain insight into the potential role of these sites, we placed them on the modeled structure of the SH2. The type-I sites were excluded from this initial analysis since a potential inclusion of a high number of false-positives could confound the results.

Figures 3A, 3B:
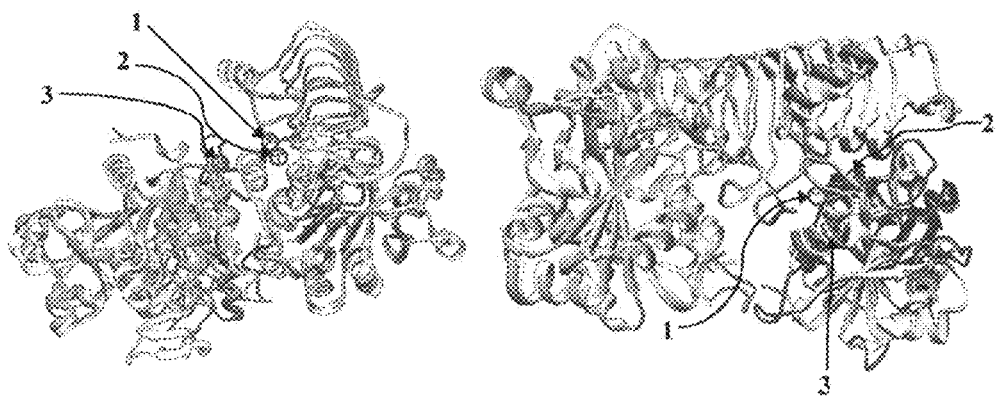
FIGS. 3A and 3B show AGPase subunit interactions. The white structures correspond to the resolved structure of potato tuber small subunit homodimers (PDB #: 1yp2). Cyan and magenta modeled structures of the small (BT2) and the large subunit (SH2) of maize endosperm, respectively, are superimposed on the structure of potato tuber small subunit homodimers. Red circles indicate the candidate Pi binding sites. Head-to-head (FIG. 3A) and Tail-to-tail (FIG. 3B) subunit interactions.
Figure 4:
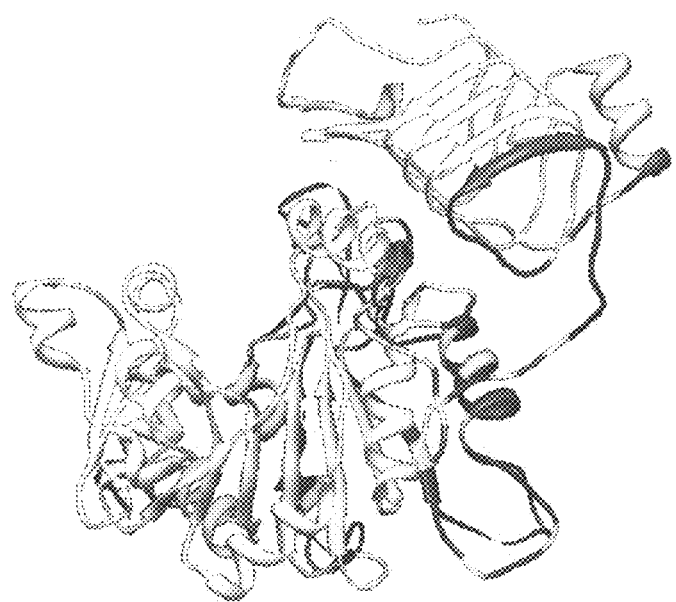
FIG. 4 shows superimposition of maize endosperm large subunit (SH2) modeled structure (magenta) on the potato tuber large subunit modeled structure (white). Red areas indicate sites in the potato tuber large subunit that are proposed to make direct contact with the small subunit (Tuncel et al., 2008).
Figure 5A:
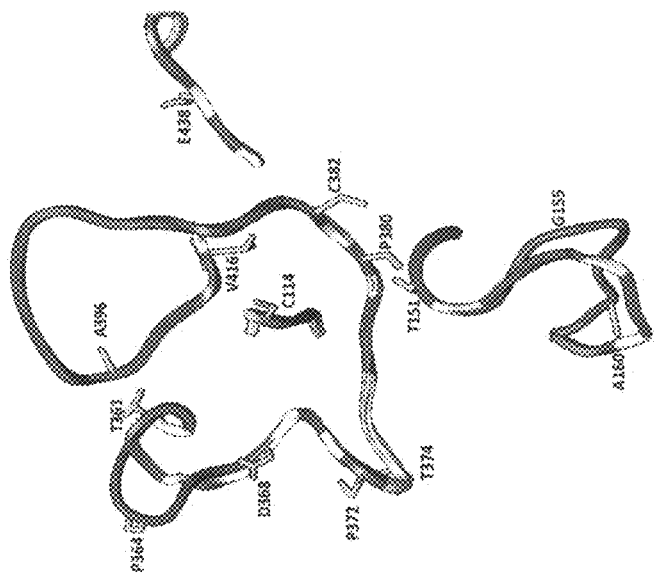
FIGS. 5A and 5B show placement of all type-II and positively selected sites on the subunit interfaces of maize endosperm large subunit (SH2). Type-I sites 149 and 361, that were changed by site-directed mutagenesis, are also placed on the structure of SH2. SH2 modeled structure (green) was superimposed on potato tuber large subunit modeled structure (white). Red areas indicate sites in the potato tuber large subunit that are proposed to make direct contact with the small subunit (Tuncel et al., 2008). Type-I, type-II and positively selected sites detected by Georgelis et al. (2008) are shown in yellow.
Figure 5B:
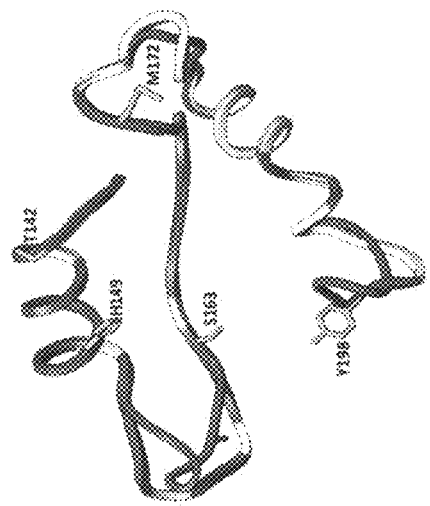

Although the only crystal structure available is a potato tuber small subunit homotetramer (Jin et al., 2005), the high degree of identity (40-45%) and similarity (55-65%) between the small and the large subunits strongly suggests that the structure of the physiologically relevant AGPase heterotetramer will be very similar or identical to the resolved homotetramer structure. Superimposition of SH2 and BT2 on the known structure agrees with this conjecture (FIGS. 3A and 3B). Additionally, the potato tuber AGPase heterotetramer was modeled after the homotetrameric structure and a molecular dynamics study was conducted to determine the most thermodynamically favorable interactions between the large and the small subunit (FIG. 2) (Tuncel et al., 2008). Superimposition of the potato tuber large subunit on SH2 indicates that the two structures are virtually identical (FIG. 4). This enables us to use the potato tuber large subunit modeled structure in order to determine the areas of SH2 that interact with BT2. According to the modeled potato tuber heterotetramer (Tuncel et al., 2008), a SH2 molecule makes direct contacts with one molecule of maize endosperm small subunit (BT2) through its C-terminal domain (tail-to-tail interaction) and another molecule of BT2 through its N-terminal catalytic domain (head-to-head interaction) as shown in FIGS. 3A and 3B. We observed that 17 out of 29 amino acid sites (type-II and positively selected) were at or near the subunit interfaces (FIGS. 5A and 5B). The areas of SH2 that participate in subunit interactions do not constitute more than 30% of the SH2 monomer structure. This means that almost 60% of the residues that were selected through evolutionary analysis were located in less than 30% of the SH2 monomer. This preferential localization of the residues at subunit interfaces raises the possibility that subunit interfaces are important for the functional specialization of the AGPase large subunit.

Example 2

Site-Directed Mutagenesis

To determine the role, if any, of type-II and positively selected amino acid sites, and particularly the ones found at the subunit interfaces, in AGPase function and gain insight into their potential roles in large subunit specialization, we performed site-directed mutagenesis in 12 sites in SH2. We mutagenized 7 SH2 sites (4 type-II, 1 positively selected, and 2 both type-II and positively selected) located at the subunit interfaces and 5 sites (3 type-II, 2 positively selected) located at the rest of the SH2 monomer. In all cases, the residue of SH2, which belongs to group 3b (FIG. 1), was changed to a residue found in other groups. To gain more information about the subunit interfaces, we scanned type-I sites for the ones that are located in the subunit interfaces. We selected type-I site 149 as a target because SH2-containing group 3b, contains a His while other groups contain the physicochemically different Ala or Ser. His was changed to a Ser. We also selected type-I site 361, which is also located in subunit interfaces. This site is invariant in Group 2 but variable in Group 3b. Group 3b can be subdivided in two subgroups, one that contains only endosperm specific large subunits including SH2 and one that includes mostly embryo large subunits. SH2 along with the other members of the former subgroup contain a Thr at site 361 while the latter subgroup contains a Cys. The Thr of SH2 was changed to a Cys, which has different physicochemical properties.

fore, the SH2 variants and wild type SH2 were expressed in *E. coli* along with wild type BT2 and the resulting heterotetramers were purified (Materials and Methods). The affinity of the SH2/BT2 complexes for the allosteric activator 3-PGA ($K_a$) was determined in the forward direction (G-1-P+ ATP4→ADP-glucose+PPi). Interestingly, 7 out of 14 SH2 variants in a complex with BT2 had a higher Ka compared to wild type SH2/BT2 (Table 4). The overwhelming majority of them (6/7) had an amino acid change in a site at the subunit interfaces. Two changes were in the head-to-head interaction areas (H149S, S163F) while four (T361C, D368S, P372A, C382F) were in the tail-to-tail interaction areas (FIG. 5). One change (Q213H) was in the N-terminal catalytic domain far from the subunit interfaces (FIG. 9). The affinity for the deactivator Pi ($K_i$) was also determined in the presence of 15 mM of 3-PGA by use of Dixon plots. Higher $K_a$ in the variants described above was accompanied by a lower $K_i$ (Table 4). It has been proposed that 3-PGA and Pi are competing for binding to AGPase and they may even bind to the same site (Boehlein et al., 2008a). Therefore, the lower affinity for 3-PGA may maximize the efficiency of the Pi effect.

TABLE 4

Kinetic and allosteric properties of wild type and variant SH2 in a complex with BT2. The Hill coefficient for Ka and Kms varies from 0.9 to 1.3.

|  | $K_m$ G-1-P (mM) | $K_{cat}$ (S$^{-1}$) | $K_m$ ATP (mM) | $K_a$ 3-PGA (mM) | (15 mM 3-PGA) $K_i$ Pi (mM) |
|---|---|---|---|---|---|
| BT2/SH2 | 0.07 (±0.01) | 39.17 (±1.23) | 0.12 (±0.02) | 0.31 (±0.06) | 16.80 (±3.84) |
| BT2/C114A | 0.07 (±0.01) | 37.21 (±1.78) | 0.14 (±0.01) | 0.39 (±0.07) | 13.23 (±3.57) |
| BT2/H149S | 0.07 (±0.01) | 35.21 (±1.50) | 0.19 (±0.03) | 2.11 (±0.13) | 3.96 (±1.50) |
| BT2/S163F | 0.09 (±0.01) | 34.65 (±2.07) | 0.42 (±0.09) | 3.29 (±0.81) | 1.83 (±0.96) |
| BT2/M172T | 0.06 (±0.01) | 38.58 (±1.98) | 0.09 (±0.01) | 0.29 (±0.08) | 17.61 (±3.78) |
| BT2/Q213H | 0.07 (±0.01) | 29.36 (±1.72) | 0.21 (±0.03) | 3.01 (±0.52) | 3.21 (±1.13) |
| BT2/V227R | 0.06 (±0.01) | 16.17 (±1.06) | 0.14 (±0.01) | 0.25 (±0.06) | 14.5 (±4.01) |
| BT2/T361C | 0.06 (±0.01) | 38.12 (±1.62) | 0.13 (±0.01) | 0.71 (±0.05) | 5.34 (±1.30) |
| BT2/D368S | 0.07 (±0.01) | 23.34 (±1.10) | 0.11 (±0.01) | 1.11 (±0.11) | 4.26 (±1.67) |
| BT2/P372A | 0.05 (±0.01) | 42.32 (±1.55) | 0.19 (±0.04) | 1.83 (±0.15) | 3.72 (±1.26) |
| BT2/C382F | 0.08 (±0.01) | 40.75 (±1.56) | 0.15 (±0.03) | 1.01 (±0.12) | 2.28 (±1.12) |
| BT2/C424V | 0.09 (±0.01) | 59.86 (±3.45) | 0.14 (±0.01) | 0.37 (±0.03) | 18.36 (±4.43) |
| BT2/E438Q | 0.05 (±0.01) | 32.87 (±2.24) | 0.13 (±0.01) | 0.35 (±0.07) | 15.22 (±3.34) |
| BT2/V502T | 0.06 (±0.01) | 41.91 (±3.13) | 0.15 (±0.02) | 0.27 (±0.03) | 17.93 (±2.93) |
| BT2/A508S | 0.06 (±0.01) | 35.77 (±1.80) | 0.09 (±0.01) | 0.30 (±0.05) | 20.43 (±4.25) |

Example 3

Glycogen Production

Figure 6:
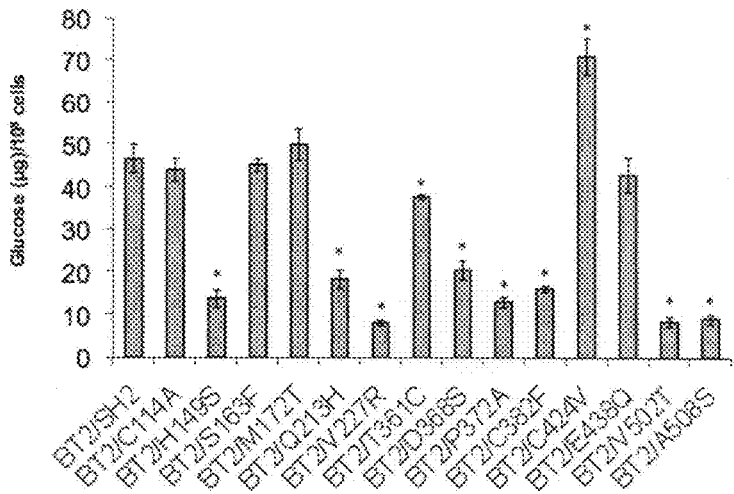
FIG. 6 shows glycogen quantitation produced by SH2 wild type and variants expressed in E. coli along with BT2. * indicates significant difference compared to wild type BT2/SH2 at p=0.05 (Student t-test) (N=4).

The wild type SH2 as well as the 14 SH2 variants created by site-directed mutagenesis were expressed with wild type BT2 in *E. coli* strain AC70R1-504 (Materials and Methods). Resulting glycogen production of cells expressing the SH2 variants and wild type SH2 was quantified. The majority of the SH2 variants (10/14) resulted in different amounts of glycogen compared to wild type SH2 (FIG. 6). This strongly suggests that the majority of the mutations introduced in SH2 were not neutral, at least when expressed in *E. coli*, despite the fact that the substituted amino acid residues are present in other large subunit groups.

Example 4

Characterization of Kinetic and Allosteric Properties of SH2 Variants

Glycogen quantitation suggests that some of the mutants created may alter function at the protein/enzyme level. There- The $K_m$ for G-1-P and ATP was determined for all variants at 15 mM 3-PGA. Except for a 4-fold lower affinity of BT2/S 163F for ATP all the other variants were indistinguishable from wild type BT2/SH2 in terms of Kms for substrates. Similarly, the majority of $K_{cat}$s was close to wild type BT2/SH2 except for BT2/C424V (~150%), BT2/V227R (~40%), and BT2/D368S (~60%). This indicates that the changes in the allosteric variants affected the affinity for effectors to a much greater extent than the effect or the mechanism of activation.

Example 5

Heat Stability

The structures of the large and the small subunit are almost identical. It has been shown that the loop connecting the C-terminal β-helix to the N-terminal catalytic domain in the small subunit is implicated in the heat stability of AGPase (Boehlein et al. 2008b). This loop makes contact with the homologous loop in the large subunit suggesting that the respective loop in the large subunit is also important for heat stability. Since 9 out of 14 substitutions in SH2 were in sites located at the subunit interfaces, including the loop described above (from amino acid number 362 to 399), the heat stability of the resulting variants was determined. The variants and wild type BT2/SH2 were heated for various amounts of time at 39° C. and remaining activity was determined by assaying in the forward direction using 20 mM 3-PGA and saturating amounts of substrates. With the exception of BT2/S163F that showed a 3-fold increase in heat stability all the other variants were similar to wild type BT2/SH2 (FIG. 7). These results indicate that the majority of the mutagenized sites at the subunit interfaces have a specific role in the allosteric properties of AGPase.

Example 6

Correlation of Kinetic and Heat Stability Data with Glycogen Production

In general, the amount of glycogen produced by the variants in *E. coli* was consistent with the kinetics data. Six out seven allosteric variants produced lower amounts of glycogen compared to wild type BT2/SH2. In the case of BT2/S163F, $K_a$ was increased and decreased glycogen production might have been expected. However, the higher heat stability of BT2/S163F may counteract the increase in $K_a$. As a result BT2/S163F produces wild type amounts of glycogen. BT2/M172T, BT2/C114A, and BT2/E438Q had wild type kinetic properties and heat stability. Not surprisingly they produced wild type amounts of glycogen. BT2/V227R and BT2/C424V had lower and higher $K_{cat}$ and glycogen production compared to wild type respectively. BT2/V502T and BT2/A508S showed identical kinetic properties and heat stability to wild type. However, their glycogen production was markedly reduced compared to wild type. One possibility could be that these variants have reduced solubility and/or increased susceptibility to proteases in *E. coli*. An alternative could be reduced transcription and translation. In all these cases, a reduced amount of SH2 and/or BT2 protein in *E. coli* cells would be expected. To investigate these possibilities, a Western blot analysis was conducted on total and soluble protein extracts from *E. coli* expressing wild type BT2/SH2, BT2/V502T and BT2/A508S by using polyclonal anti-SH2 and -BT2. The amount of SH2 and BT2 in both total and soluble protein extracts is indistinguishable between wild type and the two variants (FIG. 8). Therefore, the possible explanations discussed above for the reduced glycogen produced by BT2N502T and BT2/A508S should be excluded. The underlying reason for reduced glycogen production in these variants remains unresolved.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 5,034,322
U.S. Pat. No. 5,106,739
U.S. Pat. No. 5,589,610
U.S. Pat. No. 5,589,618
U.S. Pat. No. 5,625,136
U.S. Pat. No. 5,639,948
U.S. Pat. No. 5,650,557
U.S. Pat. No. 5,661,017
U.S. Pat. No. 5,872,216
U.S. Pat. No. 6,069,300
U.S. Pat. No. 6,184,438
U.S. Pat. No. 6,403,863
U.S. Pat. No. 6,455,760
U.S. Pat. No. 6,462,185
U.S. Pat. No. 6,696,623
U.S. Pat. No. 6,809,235
U.S. Pat. No. 6,969,783
U.S. Pat. No. 7,173,165
U.S. Pat. No. 7,312,378
U.S. Published Application No. 20030084486
U.S. Published Application No. 20030177536
U.S. Published Application No. 20040019934
U.S. Published Application No. 20040067506
U.S. Published Application No. 20040078841
U.S. Published Application No. 20040123349
International Published Application WO 2005/019425
EPO Patent Published Application No. EP 1528104
Altschul, S. F. et al. (1997) "Gapped BLAST and PSI-BLAST: A New Generation of Protein Database Search Programs" *Nucl. Acids Res.* 25:3389-3402.
Beltz, G. A., Jacobs, K. A., Eickbush, T. H., Cherbas, P. T., Kafatos, F. C. (1983) "Isolation of multigene families and determination of homologies by filter hybridization methods" *Methods of Enzymology*, R. Wu, L. Grossman and K. Moldave [eds.] Academic Press, New York 100:266-285.
Boehlein, S. K., Sewell, A. K., Cross, J., Stewart, J. D., and Hannah, L. C. (2005) "Purification and characterization of adenosine diphosphate glucose pyrophosphorylase from maize/potato mosaics" *Plant Physiol.* 138: 1552-1562.
Clancy, M. and Hannah, L. C. (2002) "Splicing of the maize Sh1 first intron is essential for enhancement of gene expression, and a T-rich motif increases expression without affecting splicing" *Plant Physiol.* 130(2):918-29.
Cross, J. M., Clancy, M., Shaw, J., Greene, T. W., Schmidt, R. R. Okita, T. W. and Hannah, L. C. (2004) "Both subunits of ADP-glucose pyrophosphorylase are regulatory" *Plant Physiol.* 135: 137-140.
Furtado, A. et al. (2002) "Tools for Use in the Genetic Engineering of Barley" *Proceedings of the 10th Australian Barley technical Symposium, Canberra*, ACT, Australia.
Giroux, M. J., Shaw, J., Barry, G., Cobb, B. G., Greene, T. W., Okita, T. W., and Hannah, L. C. (1996) "A single mutation that increases maize seed weight" *Proc. Natl. Acad. Sci. USA* 93: 5824-5829.
Good, X. et al. (1994) "Reduced ethylene synthesis by transgenic tomatoes expressing S-adenosylmethionine hydrolase" *Plant Molec. Biol.* 26:781-790.
Greene, T. W., and Hannah, L. C. (1998a) "Enhanced stability of maize endosperm ADP-glucose pyrophosphorylase is gained through mutants that alter subunit interactions" *Proc. Natl. Acad. Sci. USA* 95: 13342-13347.
Greene, T. W., Kavakli, I. H., Kahn, M., and Okita, T. W. (1998b) "Generation of up-regulated allosteric variants of potato ADP-glucose pyrophosphorylase by reversion genetics" *Proc. Natl. Acad. Sci. USA* 95: 10322-10327.
Hannah L. C., Shaw, J. R., Giroux, M., Reyss, A., Prioul, J.-L., Bae, J.-M. and Lee, J.-Y. (2001) "Maize Genes Encoding the Small Subunit of ADP-Glucose Pyrophosphorylase" *Plant Physiol.* 127:173-183.

Hannah, L. C., and Nelson, O. E., Jr. (1976) "Characterization of ADP-glucose pyrophosphorylase from shrunken-2 and brittle-2 mutants of maize" *Biochem. Genet.* 14: 547-560.

Hwang, Y-S. et al. (2002) "Analysis of the Rice Endosperm-Specific Globulin Promoter in Transformed Rice Cells" *Plant Cell Rep.* 20:842-847.

Karlin S. and Altschul, S. F. (1990) "Methods for Assessing the Statistical Significance of Molecular Sequence Features by Using General Scoring Schemes" *Proc. Natl. Acad. Sci. USA* 87:2264-2268.

Karlin S. and Altschul, S. F. (1993) "Applications and Statistics for Multiple High-Scoring Segments in Molecular Sequences" *Proc. Natl. Acad. Sci. USA* 90:5873-5877.

Lewin, B. (1985) *Genes II*, John Wiley & Sons, Inc., p. 96.

Maniatis, T., E. F. Fritsch, J. Sambrook (1982) "Nuclease Bal31" *Molecular Cloning: A Laboratory Manual*, Cold Spring Harbor Laboratory, Cold Spring Harbor, N.Y.

Obana, Y., Omoto, D., Kato, C., Matsumoto, K., Nagai, Y., Kavakli, I. H., Hamada, S., Edwards, G. E., Okita, T. W., Matsui, H., and Ito, H. (2006) "Enhanced turnover of transitory starch by expression of up-regulated ADP-glucose pyrophosphorylase in *Arabidopsis thaliana*" *Plant Sci.* 170: 1-11.

Sakulsingharoja, C., Choi, S. B., Hwang, S. K., Edwards, G. E., Bork, J., Meyer, C. R., Preiss, J., and Okita, T. W. (2004) "Engineering starch biosynthesis for increasing rice seed weight: the role of the cytoplasmic ADP-glucose pyrophosphorylase" *Plant Sci.* 167: 1323-1333.

Smidansky, E. D., Clancy, M., Meyer, F. D., Lanning, S. P., Blake, N. K., Talbert, L. E., and Giroux, M. J. (2002) "Enhanced ADP-glucose pyrophosphorylase activity in wheat endosperm increases seed yield" *Proc. Natl. Acad. Sci.* 99: 1724-1729.

Smidansky, E. D., Martin, J. M., Hannah, L. C., Fischer, A. M., and Giroux, M. J. (2003) "Seed yield and plant biomass increases in rice are conferred by deregulation of endosperm ADP-glucose pyrophosphorylase" *Planta* 216: 656-664.

Stark, D. M., Timmerman, K. P., Barry, G., Preiss, J., and Kishore, G. M. (1992) "Regulation of the amount of starch in plant tissues by ADP-glucose pyrophosphorylase" *Science* 258: 287-292.

Tsai, C. Y., and Nelson, O. E. (1966) "Starch deficient maize mutants lacking adenosine diphosphate glucose pyrophosphorylase activity" *Science* 151: 341-343.

Wang, Z., Chen, X., Wang, J., Liu, T., Liu, Y., Zhao, L., and Wang, G. (2007) "Increasing maize seed weight by enhancing the cytoplasmic ADP-glucose pyrophosphorylase activity in transgenic plants" *Plant Cell Tiss. Organ Cult.* 88: 83-92.

Wu, C-L. et al. (1998) "Promoters of Rice Seed Storage Protein Genes Direct Endosperm-Specific Gene Expression in Transgenic Rice" *Plant and Cell Physiology*, 39(8): 885-889.

Xu, D., McElroy, D., Thornburg, R. W., Wu, R. et al. (1993) "Systemic induction of a potato pin2 promoter by wounding, methyl jasmonate, and abscisic acid in transgenic rice plants" *Plant Molecular Biology* 22:573-588.

Akihiro T, Mizuno K, Fujimura T (2005) Gene expression of ADP-glucose pyrophosphorylase and starch contents in rice cultured cells are cooperatively regulated by sucrose and ABA. Plant Cell Physiol 46: 937-946

Arnold K, Bordoli L, Kopp J, Schwede T (2006) The SWISS-MODEL Workspace: a web-based environment for protein structure homology modeling, Bioinformatics 22: 195-201

Ballicora M A, Dubay J R, Devillers C H, Preiss J (2005) Resurrecting the ancestral enzymatic role of a modulatory subunit. J Biol Chem 280: 10189-10195

Ballicora M A, Erben E D, Yazaki T, Bertolo A L, Demonte A M, Schmidt J R, Aleanzi M, Bejar C M, Figueroa C M, Fusari C M, Iglesias A A, Preiss J (2008) Identification of regions critically affecting kinetics and allosteric regulation of the *Escherichia coli* ADP-glucose pyrophosphorylase by modeling and pentapeptide-scanning mutagenesis. J Bacteriol 189: 5325-5333

Ballicora M A, Fu Y, Nesbitt N M, Preiss J (1998) ADP-Glc pyrophosphorylase from potato tubers. Site-directed mutagenesis studies of the regulatory sites. Plant Physiol 118: 265-274

Bejar C M, Jin X, Ballicora M A, Preiss J (2006) Molecular architecture of the glucose 1-phosphate site in ADP-glucose pyrophosphorylases. J Biol Chem 281: 40473-40484

Bishop J G (2005) Directed mutagenesis confirms the functional importance of positively selected sites in polygalacturonase inhibitor protein. Mol Biol Evol 22: 1531-1534

Boehlein S K, Shaw J R, Stewart J D, Hannah L C (2008a) Heat stability and allosteric properties of the maize endosperm ADP-glucose pyrophosphorylase are intimately intertwined. Plant Physiol 146: 289-299

Boehlein S K, Shaw J R, Stewart J D, Hannah L C. (2008b) Characterization of an autonomously activated plant adenosine diphosphate glucose pyrophosphorylase. Plant Physiol. doi: 10.1104/pp. 108.126862

Burger B T, Cross J, Shaw J R, Caren J, Greene T W, Okita T W, Hannah L C (2003) Relative turnover numbers of maize endosperm and potato tuber ADP-glucose pyrophosphorylases in the absence and presence of 3-PGA. Planta 217: 449-456

Cavatorta J R, Savage A E, Yeam I, Gray S M, Jahn M M (2008) Positive Darwinian selection at single amino acid sites conferring plant virus resistance. J Mol Evol 67: 551-557

Courville P, Urbankova E, Rensing C, Chaloupka R, Quick M, Cellier M F (2008) Solute carrier 11 cation symport requires distinct residues in transmembrane helices 1 and 6. J Biol Chem 283: 9651-9658

Crevillen P, Ballicora M A, Merida A, Preiss J, Romero J M (2003) The different large subunit isoforms of *Arabidopsis thaliana* ADP-glucose pyrophosphorylase confer distinct kinetic and regulatory properties to the heterotetrameric enzyme. J Biol Chem 278: 28508-28515

Crevillen P, Ventriglia T, Pinto F, Orea A, Merida A, Romero J M (2005). Differential pattern of expression and sugar regulation of *Arabidopsis thaliana* ADP-glucose pyrophosphorylase-encoding genes. J Biol Chem 280: 8143-8149

Cross J M, Clancy M, Shaw J, Boehlein S, Greene T, Schmidt R, Okita T, Hannah L C (2005) A polymorphic motif in the small subunit of ADP-glucose pyrophosphorylase modulates interactions between the small and large subunits. Plant J 41: 501-511

Frueauf J B, Ballicora M A, Preiss J (2001) Aspartate residue 142 is important for catalysis by ADP-Glc pyrophosphorylase from *Escherichia coli*. J Biol Chem 276: 46319-46325

Frueauf J B, Ballicora M A, Preiss J (2003) ADP-Glc pyrophosphorylase from potato tuber: site-directed mutagenesis of homologous aspartic acid residues in the small and large subunits. Plant J 33: 503-511

Fu Y, Ballicora M A, Preiss J (1998) Mutagenesis of the Glc-1-phosphate-binding site of potato tuber ADP-Glc pyrophosphorylase. Plant Physiol 117: 989-996

Georgelis N, Braun E L, Hannah L C (2008) Duplications and functional divergence of ADP-glucose pyrophosphorylase genes in plants. BMC Evol Biol 8: 232

Georgelis N, Braun E L, Shaw J R, Hannah L C (2007) The two AGPase subunits evolve at different rates in angiosperms, yet they are equally sensitive to activity-altering amino acid changes when expressed in bacteria. Plant Cell 19: 1458-1472

Georgelis N, Hannah L C (2008) Isolation of a heat-stable maize endosperm ADP-glucose pyrophosphorylase variant. Plant Sci 175: 247-254

Greene T W, Chantler S E, Kahn M L, Barry G F, Preiss J, Okita T W (1996a) Mutagenesis of the potato ADPglucose pyrophosphorylase and characterization of an allosteric mutant defective in 3-phosphoglycerate activation. Proc Natl Acad Sci USA 93: 1509-1513

Greene T W, Woodbury R L, Okita T W (1996b) Aspartic acid 413 is important for the normal allosteric functioning of ADP-glucose pyrophosphorylase. Plant Physiol 112: 1315-1320

Gribaldo S, Casane D, Lopez P, Philippe H (2003) Functional divergence prediction from evolutionary analysis: a case study of vertebrate hemoglobin. Mol Biol Evol 20: 1754-1759

Gu X (1999) Statistical methods for testing functional divergence after gene duplication. Mol Biol Evol 16: 1664-1674

Gu X (2006) A simple statistical method for estimating type-II (cluster-specific) functional divergence of protein sequences. Mol Biol Evol 23: 1937-1945

Hannah L C (2005) Starch synthesis in the maize endosperm. Maydica 50: 497-506

Hanson R S, Phillips J A (1981) Chemical composition. In Manual of Methods for General Bacteriology, P. Gerhandt, R. G. E. Murray, R. N. Costilow, E. W. Nester, W. A. Wood, N. R. Krieg, and G. B. Phillips, eds (Washington D.C.: American Society for Microbiology), pp. 328-364

Hwang S K, Hamada S, Okita T W (2006) ATP binding site in the plant ADP-glucose pyrophosphorylase large subunit. FEBS Lett 580: 6741-6748

Hwang S K, Hamada S, Okita T W (2007) Catalytic implications of the higher plant ADP-glucose pyrophosphorylase large subunit. Phytochemistry 68: 464-477

Hwang S K, Nagai Y, Kim D, Okita T W (2008) Direct appraisal of the potato tuber ADP-glucose pyrophosphorylase large subunit in enzyme function by study of a novel mutant form. J Biol Chem 283: 6640-6647

Hwang S K, Salamone P R, Okita T W (2005) Allosteric regulation of the higher plant ADP-glucose pyrophosphorylase is a product of synergy between the two subunits. FEBS Lett 579: 983-990

Iglesias A, Barry G F, Meyer C, Bloksberg L, Nakata P, Greene T, Laughlin M J, Okita T W, Kishore G M, Preiss J (1993) Expression of the potato tuber ADP-glucose pyrophosphorylase in *Escherichia coli*. J Biol Chem 268: 1081-1086

Jin X, Ballicora M A, Preiss J, Geiger J H (2005) Crystal structure of potato tuber ADP-Glc pyrophosphorylase. EMBO J 24: 694-704

Kavakli I H, Greene T W, Salamone P R, Choi S B, Okita T W (2001b) Investigation of subunit function in ADP-glucose pyrophosphorylase. Biochem Biophys Res Commun 281: 783-787

Kavakli I H, Park J S, Slattery C J, Salamone P R, Frohlick J, Okita T W (2001a) Analysis of allosteric effector binding sites of potato ADP-glucose pyrophosphorylase through reverse genetics. J Biol Chem 276: 40834-40840

Kim D, Hwang S K, Okita T W (2007) Subunit interactions specify the allosteric regulatory properties of the potato tuber ADP-glucose pyrophosphorylase. Biochem Biophys Res Commun 362: 301-306

Kumar S, Tamura K, Nei M (2004) MEGA3: Integrated software for Molecular Evolutionary Genetics Analysis and sequence alignment. Brief Bioinform 5: 150-163

Laughlin M J, Payne J W, Okita T W (1998) Substrate binding mutants of the higher plant ADP-glucose pyrophosphorylase. Phytochemistry 47: 621-629

Luthy R, Bowie J U, Eisenberg D (1992) Assessment of protein models with 3-dimensional profiles, Nature 356: 83-85

Norrgard M A, Ivarsson Y, Tars T, Mannervik B (2006) Alternative mutations of a positively selected residue elicit gain or loss of functionalities in enzyme evolution. Proc Natl Acad Sci USA 103: 4876-4881

Ohdan T, Francisco P B Jr, Sawada T, Hirose T, Terao T, Satoh H, Nakamura Y (2005) Expression profiling of genes involved in starch synthesis in sink and source organs of rice. J Exp Bot 56: 3229-3244

Pettersen E F, Goddard T D, Huang C C, Couch G S, Greenblatt D M, Meng E C, Ferrin T E (2004) UCSF Chimera—A Visualization System for Exploratory Research and Analysis. J Comput Chem 25:1605-1612

Philippe H, Casane D, Gribaldo S, Lopez P, Meunier J (2003) Heterotachy and functional shift in protein evolution. IUBMB Life 55: 257-265

Schwede T, Kopp J, Guex N, Peitsch M C (2003) SWISS-MODEL: an automated protein homology-modeling server, Nucleic Acids Res 31: 3381-3385

Tuncel A, Kavakli I H, Keskin O (2008) Insights into subunit interactions in the heterotetrameric structure of potato ADP-glucose pyrophosphorylase. Biophys J 95: 3628-3639

Ventriglia T, Kuhn M L, Ruiz M T, Ribeiro-Pedro M, Valverde F, Ballicora M A, Preiss J, Romero J M (2008) Two Arabidopsis ADP-Glucose Pyrophosphorylase Large Subunits (APL1 and APL2) Are Catalytic. Plant Physiol 148: 65-76

Vriend G (1990) What If—a molecular modeling and drug design program. J Mol Graph 8: 52-56

We claim:

1. A polynucleotide encoding a mutant maize endosperm AGPase large subunit protein, or a functional fragment of said protein that exhibits the same activity as the full-length AGPase large subunit protein, wherein said protein comprises an amino acid mutation of the cysteine at position 424 of the wild type maize endosperm AGPase large subunit protein, wherein said cysteine is replaced by an amino acid that confers increased enzymatic activity when said mutant AGPase large subunit protein is expressed to form an AGPase enzyme, or wherein said protein comprises an amino acid mutation of the serine amino acid at position 163 of the wild type maize endosperm AGPase large subunit protein, wherein said serine is replaced by an amino acid that confers increased heat stability of AGPase activity when said mutant AGPase large subunit protein is expressed to form an AGPase enzyme; or said protein comprises both of said amino acid mutations; and wherein said functional fragment comprises one or both of said amino acid mutations.

2. The polynucleotide according to claim 1, wherein said replacement amino acid that confers increased enzymatic activity is a valine or said replacement amino acid that confers increase heat stability is a phenylalanine.

3. The polynucleotide according to claim 1, wherein said mutant maize endosperm AGPase large subunit protein encoded by said polynucleotide comprises the amino acid sequence shown in SEQ ID NO: 2, SEQ ID NO: 18, or SEQ ID NO: 47, or a functional fragment thereof that exhibits the same activity as the full-length AGPase large subunit protein.

4. The polynucleotide according to claim 1, wherein said polynucleotide comprises the nucleotide sequence shown in SEQ ID NO: 1, SEQ ID NO: 17, or SEQ ID NO: 47, or a fragment thereof that encodes a functional fragment of said protein that exhibits the same activity as the full-length AGPase large subunit protein.

5. The polynucleotide according to claim 1, wherein said polynucleotide is provided in an expression construct.

6. A transgenic plant or plant tissue comprising a polynucleotide encoding a mutant maize endosperm AGPase large subunit protein, or a functional fragment of said protein that exhibits the same activity as the full-length AGPase large subunit protein, wherein said protein comprises an amino acid mutation of the cysteine at position 424 of the wild type maize endosperm AGPase large subunit protein, wherein said cysteine is replaced by an amino acid that confers increased enzymatic activity when said mutant AGPase large subunit protein is expressed to form an AGPase enzyme, or wherein said protein comprises an amino acid mutation of the serine amino acid at position 163 of the wild type maize endosperm AGPase large subunit protein, wherein said serine is replaced by an amino acid that confers increased heat stability of AGPase activity when said mutant AGPase large subunit protein is expressed to form an AGPase enzyme; or said protein comprises both of said amino acid mutations; and wherein said functional fragment comprises one or both of said amino acid mutations.

7. The plant or plant tissue according to claim 6, wherein the plant also expresses a small subunit protein of AGPase.

8. The plant or plant tissue according to claim 6, wherein said mutant maize endosperm AGPase large subunit protein comprises a second mutation that confers increased heat stability and/or said mutant maize endosperm AGPase large subunit protein further comprises a mutation that confers increased seed weight.

9. The plant or plant tissue according to claim 6, wherein said plant or plant tissue is monocotyledonous.

10. The plant or plant tissue according to claim 9, wherein said monocotyledonous plant or plant tissue is selected from the group consisting of rice, wheat, barley, oat, sorghum, maize, lily, and millet.

11. The plant or plant tissue according to claim 6, wherein said plant is Zea mays or said plant tissue is from Zea mays.

12. The plant or plant tissue according to claim 6, wherein said plant tissue is a seed.

13. The plant or plant tissue according to claim 6, wherein said replacement amino acid that confers increased enzymatic activity is a valine or said replacement amino acid that confers increased heat stability is a phenylalanine.

14. The plant or plant tissue according to claim 6, wherein said mutant maize endosperm AGPase large subunit protein encoded by said polynucleotide comprises the amino acid sequence shown in SEQ ID NO: 2, SEQ ID NO: 18, or SEQ ID NO: 47, or a functional fragment thereof that exhibits the same activity as the full-length AGPase large subunit protein.

15. The plant or plant tissue according to claim 6, wherein said polynucleotide comprises the nucleotide sequence shown in SEQ ID NO: 1, SEQ ID NO: 17, or SEQ ID NO: 47, or a fragment thereof that encodes a functional fragment of said protein that exhibits the same activity as the full-length AGPase large subunit protein.

16. A method of increasing starch biosynthesis and/or heat resistance of a plant, said method comprising incorporating a polynucleotide into the genome of a plant and expressing the protein encoded by said polynucleotide, wherein said polynucleotide encodes a mutant maize endosperm AGPase large subunit protein, or a functional fragment of said protein that exhibits the same activity as the full-length AGPase large subunit protein, wherein said protein comprises an amino acid mutation of the cysteine at position 424 of the wild type maize endosperm AGPase large subunit protein, wherein said cysteine is replaced by an amino acid that confers increased enzymatic activity when said mutant AGPase large subunit protein is expressed to form an AGPase enzyme, or wherein said protein comprises an amino acid mutation of the serine amino acid at position 163 of the wild type maize endosperm AGPase large subunit protein, wherein said serine is replaced by an amino acid that confers increased heat stability of AGPase activity when said mutant AGPase large subunit protein is expressed to form an AGPase enzyme; or said mutant plant AGPase large subunit protein comprises both of said amino acid mutations; and wherein said functional fragment comprises one or both of said amino acid mutations.

17. The method according to claim 16, wherein said replacement amino acid that confers increased enzymatic activity is a valine or said replacement amino acid that confers increased heat stability is a phenylalanine.

18. The method according to claim 16, wherein said mutant plant maize endosperm AGPase large subunit protein encoded by said polynucleotide comprises the amino acid sequence shown in SEQ ID NO: 2, SEQ ID NO: 18, or SEQ ID NO: 47, or a functional fragment thereof that exhibits the same activity as the full-length AGPase large subunit protein.

19. The method according to claim 16, wherein said polynucleotide comprises the nucleotide sequence shown in SEQ ID NO: 1, SEQ ID NO: 17, or SEQ ID NO: 47, or a fragment thereof that encodes a functional fragment of said protein that exhibits the same activity as the full-length AGPase large subunit protein.

20. The method according to claim 16, wherein said mutant maize endosperm AGPase large subunit protein comprises a second mutation that confers increased heat stability and/or said mutant maize endosperm AGPase large subunit protein further comprises a mutation that confers increased seed weight.

21. The plant or plant tissue according to claim 6, wherein said plant or plant tissue is dicotyledonous.

22. The plant or plant tissue according to claim 21, wherein said dicotyledonous plant or plant tissue is selected from the group consisting of pea, alfalfa, chickpea, chicory, clover, kale, lentil, soybean, tobacco, potato, sweet potato, radish, cabbage, rape, apple tree, and lettuce.

23. The polynucleotide according to claim 1, wherein said mutant maize endosperm AGPase large subunit protein comprises a second mutation that confers increased heat stability and/or said mutant maize endosperm AGPase large subunit protein further comprises a mutation that confers increased seed weight.

* * * * *

UNITED STATES PATENT AND TRADEMARK OFFICE
CERTIFICATE OF CORRECTION

PATENT NO.        : 8,362,321 B2
APPLICATION NO.   : 12/322467
DATED             : January 29, 2013
INVENTOR(S)       : L. Curtis Hannah et al.

Page 1 of 1

It is certified that error appears in the above-identified patent and that said Letters Patent is hereby corrected as shown below:

In the Specification:

Column 10,
Line 48, "omithine" should read --ornithine--.

Column 26,
Line 46, "Kms" should read --$K_m$s--.

Column 27,
Line 46, "BT2N502T" should read --BT2/V502T--.

Column 99,
Lines 23-24, "mutant plant maize" should read --mutant maize--.

Signed and Sealed this
Twenty-third Day of April, 2013

Teresa Stanek Rea
*Acting Director of the United States Patent and Trademark Office*